(12) United States Patent
Flyer et al.

(10) Patent No.: US 12,209,144 B2
(45) Date of Patent: Jan. 28, 2025

(54) CYCLIC PEPTIDES AS PROPROTEIN CONVERTASE SUBTILISIN/KEXIN TYPE 9 (PCSK9) INHIBITORS FOR THE TREATMENT OF METABOLIC DISORDERS

(71) Applicant: Novartis AG, Basel (CH)

(72) Inventors: Alec Nathanson Flyer, Boston, MA (US); Andrei Alexandrovich Golosov, Cambridge, MA (US); Philipp Grosche, Inzlingen (DE); Ian Lewis, Riehen (CH); Eugene Yuejin Liu, Lexington, MA (US); Andreas Marzinzik, Weil am Rhein (DE); Lauren Gilchrist Monovich, Belmont, MA (US); Johannes Ottl, Lörrach (DE); Tajesh Jayprakash Patel, Westford, MA (US); Patrick Crawford Reid, Tokyo (JP); Mohindra Seepersaud, Acton, MA (US)

(73) Assignee: Novartis AG, Basel (CH)

( * ) Notice: Subject to any disclaimer, the term of this patent is extended or adjusted under 35 U.S.C. 154(b) by 379 days.

(21) Appl. No.: 17/296,679

(22) PCT Filed: Nov. 26, 2019

(86) PCT No.: PCT/IB2019/060203
§ 371 (c)(1),
(2) Date: May 25, 2021

(87) PCT Pub. No.: WO2020/110011
PCT Pub. Date: Jun. 4, 2020

(65) Prior Publication Data
US 2022/0024981 A1  Jan. 27, 2022

Related U.S. Application Data

(60) Provisional application No. 62/772,033, filed on Nov. 27, 2018.

(51) Int. Cl.
*C07K 7/64* (2006.01)
*A61K 38/12* (2006.01)
*A61K 45/06* (2006.01)
*A61K 38/00* (2006.01)

(52) U.S. Cl.
CPC ............... *C07K 7/64* (2013.01); *A61K 38/12* (2013.01); *A61K 45/06* (2013.01); *A61K 38/00* (2013.01)

(58) Field of Classification Search
None
See application file for complete search history.

(56) References Cited

U.S. PATENT DOCUMENTS

| 5,114,946 A | 5/1992 | Lawter et al. |
| 6,780,968 B1 | 8/2004 | Giorgi et al. |
| 7,015,196 B1 | 3/2006 | Perrotta et al. |
| 8,492,517 B2 | 7/2013 | Yang et al. |
| 8,877,890 B2 | 11/2014 | Yang et al. |
| 2009/0186891 A1 | 7/2009 | Kwak et al. |
| 2011/0262963 A1 | 10/2011 | Geierstanger et al. |
| 2012/0252796 A1 | 10/2012 | Pingali et al. |

FOREIGN PATENT DOCUMENTS

| CN | 108239073 A | 7/2018 |
| EP | 1297826 A1 | 4/2003 |
| WO | 9834949 A2 | 8/1998 |
| WO | 2000008046 A1 | 2/2000 |
| WO | 2001029066 A2 | 4/2001 |
| WO | 2010046900 A2 | 4/2010 |
| WO | 2011063366 A1 | 5/2011 |
| WO | 2014150395 A1 | 9/2014 |

OTHER PUBLICATIONS

Xu et al. Small molecules as inhibitors of PCSK9: Current status and future challenges. Eur J Med Chem. Jan. 2019. Epub Nov. 11, 2018. (Year: 2019).*
Altamura, et al., New monocyclic and acyclic hNK-2 antagonists retaining the beta-turn feature. X-ray and molecular modelling studies, Acta Crystallographica Section B: Structural Science, Feb. 28, 2006, 889-896, B62.
Bergeron, et al., Proprotein Convertase Subtilisin/Kexin Type 9 Inhibition: A New Therapeutic Mechanism for Reducing Cardiovascular Disease Risk, Circulation, Oct. 27, 2015, 1648-1666, 132(17).
Fedi, et al., Insertion of an Aspartic Acid Moiety into Cyclic Pseudopeptides: Synthesis and Biological Characterization of Potent Antagonists for the Human Tachykinin NK-2 Receptor, J. Med. Chem., 2004, 6935-6947, 47(27).
(Continued)

*Primary Examiner* — Aradhana Sasan
*Assistant Examiner* — Jia-Hai Lee
(74) *Attorney, Agent, or Firm* — Timothy P. O'Dea

(57) ABSTRACT

The disclosure relates to inhibitors of PCSK9 useful in the treatment of lipid metabolism, and other diseases in which PCSK9 plays a role, having the Formula (I):

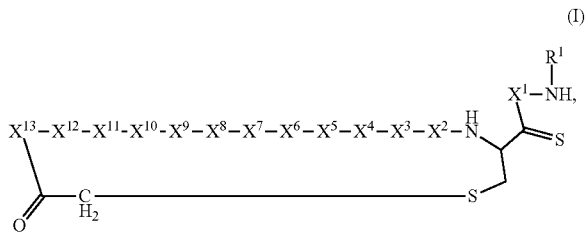

or a pharmaceutically acceptable salt, hydrate, solvate, stereoisomer, or tautomer thereof, wherein $R^1$, $X^1$, $X^2$, $X^3$, $X^4$, $X^5$, $X^6$, $X^7$, $X^8$, $X^9$, $X^{10}$, $X^{11}$, $X^{12}$, and $X^{13}$ are described herein.

1 Claim, No Drawings

Specification includes a Sequence Listing.

(56) References Cited

OTHER PUBLICATIONS

Giannotti, et al., Discovery of Potent Cyclic Pseudopeptide Human Tachykinin NK-2 Receptor Antagonists, Journal of Medicinal Chemistry, Nov. 2, 2000, 4041-4044, 43(22).

Giolitti, et al., Monocyclic Human Tachykinin NK-2 Receptor Antagonists as Evolution of a Patent Bicyclic Antagonist: QSAR and Site-Directed Mutagenesis Studies, Journal of Medicinal Chemistry, 2002, 3418-3429, 45(16).

Paoli, et al., Solid State Investigation and Characterization of a Nepadutant Precursor: Polymorphic and Pseudopolymorphic Forms of MEN11282, Crystal Growth and Design, Aug. 15, 2016, 5294-5304., 16.

Taechalertpaisarn, et al., Small Molecule Inhibitors of the PCSK9-LDLR Interaction, Journal of the American Chemical Society, 2018, 1541-1545, 140(9).

Valenza, et al., Regio- and Stereoselective Cycloadditions of Cyclic Nitrones to Maleic Diamide Forced in a Peptide: Synthesis of Potent Ligands of Human NK-2 Receptor, J. Org. Chem, 2000, 4003-4008, 65(13).

Xu, et al., Small molecules as inhibitors of PCSK9: Current status and future challenges, European Journal of Medicinal Chemistry, 162, 212-233, 2019.

Yang, et al., Substitution of Gly with Ala enhanced the melanoma uptake f technetium-99m-labeled Arg-Ala-Asp-conjugated alpha-melancyte stimulating hormone peptide, Bioorganic & Medicinal Chemistry Letters, 22(4), 1541-1545, Jan. 10, 2012.

\* cited by examiner

CYCLIC PEPTIDES AS PROPROTEIN CONVERTASE SUBTILISIN/KEXIN TYPE 9 (PCSK9) INHIBITORS FOR THE TREATMENT OF METABOLIC DISORDERS

RELATED APPLICATIONS

This application is a U.S. National Phase filing of International Application Serial No. PCT/IB2019/060203, filed Nov. 26, 2019, and claims the benefit of and priority to U.S. Provisional Application No. 62/772,033, filed Nov. 27, 2018, the entire contents of which are incorporated herein by reference in its entirety.

FIELD OF DISCLOSURE

The disclosure is directed to modulators of proprotein convertase subtilisin/kexin type 9 (PCSK9) useful in the treatment of diseases or disorders associated with PCSK9 protease. Specifically, the disclosure is concerned with peptides and compositions, which inhibit PCSK9, methods of treating diseases or disorders associated with PCSK9, and methods of synthesis of these peptides.

BACKGROUND OF THE DISCLOSURE

Proprotein convertase subtilisin/kexin type 9 (PCSK9) is a member of the secretory subtilase, subtilisin serine protease family, and is expressed in many tissues and cell types. The PCSK9 protein contains a signal sequence, a prodomain, a catalytic domain containing a conserved triad of residues (D186, H226 and S386), and a C-terminal domain and is synthesized as a soluble 74-kDa precursor that undergoes autocatalytic cleavage in the endoplasmic reticulum. The autocatalytic activity has been shown to be required for secretion.

PCSK9 has pronounced effects on plasma low density lipoprotein cholesterol (LDL-C) levels via its modulation of hepatic low density lipoprotein receptors (LDLR), the main route by which cholesterol is removed from the circulation. PCSK9 binds the LDLR and directs it to lysosomal degradation, thereby increasing plasma LDL-C levels and, in turn, coronary heart disease (CHD) risk. (Maxwell K. N., Proc. Natl. Acad. Sci., 101, 2004, 7100-7105; Park, S. W., J. Biol. Chem. 279, 2004, 50630-50638; Lagace T. A., et. al. J. Clin. Invest. 2006, 116(11):2995-3005). Overexpression of mouse or human PCSK9 in mice has been shown to elevate total and LDL-C levels and dramatically reduce hepatic LDLR protein, without an observed effect on the levels of mRNA, SREBP, or SREBP protein nuclear to cytoplasmic ratio. (Maxwell K. N., Proc. Natl. Acad. Sci. 101, 2004, 7100-7105). Moreover, mutations in PCSK9 that cause loss of PCSK9 function in mouse models have also been shown to lower total and LDL-C levels. (Cohen, J. C., et al., N. Engl. J. Med., 354, 2006, 1264-1272). Thus, the results indicate that modulation of PCSK9 results in a reduction of LDLR protein levels.

Gene deletion of PCSK9 has also been conducted in mice. PCSK9 knockout mice show an approximate 50% reduction in plasma cholesterol levels and enhanced sensitivity to statins in reducing plasma cholesterol (Rashid, S., et al., Proc. Natl. Acad. Sci., 2005, 102:5374-5379). Human genetic data strongly support the role of PCSK9 in LDL homeostasis. The link between PCSK9 and plasma LDL-C levels was first established by the discovery of PCSK9 missense mutations in patients with an autosomal dominant form of familial hypercholesterolemia (Abifadel, M., et al., Nature, 2003, 34:154-6). Patients carrying PCSK9 gain-of-function alleles have increased plasma LDL-C levels and premature CHD, whereas those with PCSK9 loss-of-function alleles have markedly reduced plasma LDL-C and are protected from CHD.

PCSK9 also plays a role in Lipoprotein (a) (Lp(a)) metabolism. Lp(a) is a proatherogenic lipoprotein comprised of an LDL particle covalently linked to apoLp(a). Human genetic studies indicate that Lp(a) is causally associated with CHD risk. PCSK9 therapeutic antibodies have been shown to significantly reduce Lp(a) levels in patients with hypercholesterolemia. (Desai, N. R., et. al., Circulation. 2013, 128(9):962-969; Lambert, G., et. al., Clin. Sci., 2017, 131, 261-268). Patients receiving statin therapy treated with a monoclonal antibody against PCSK9 have shown up to 32% reduction in Lp(a) levels compared to placebo. (Desai N. R., et. al., Circulation. 2013, 128(9):962-969).

In addition to having cardiovascular effects, PCSK9 plays an important role in sepsis, a life-threatening condition caused by a body's response to infection. Overexpression of PSCK9 in septic mice has been shown to aggravate sepsis by increasing inflammation, while inhibition of PCSK9 has been shown to reduce mortality. (Dwivedi, D. J., et al., Shock, 2016, 46(6), 672-680). Moreover, flow cytometry studies in human HepG2 cells have shown that PCSK9 negatively regulates gram-negative lipopolysaccharide (LPS) uptake by hepatocytes through the regulation of the LDLR-mediated bacterial lipid uptake of lipoteichoic acid (LTA) and LPS through an LDL-dependent mechanism. (Grin, P. M., et al., Nature, 2018, 8(1):10496) Thus, inhibition of PCSK9 has the potential to treat sepsis by reducing the body's immune response to an infection.

Currently, there are no known small molecule inhibitors of PCSK9. The only known marketed inhibitors of PCSK9 are anti-PCSK9 antibodies. Inhibition of PCSK9 with a small molecule inhibitor therefore has the potential to be a treatment for a range of diseases, including hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, triglyceride-rich lipoproteins (TRL), elevated triglycerides, sepsis, xanthoma and other disorders. For these reasons, there remains a need for novel and potent small molecule PCSK9 inhibitors.

SUMMARY OF THE DISCLOSURE

A first aspect of the disclosure relates to cyclic polypeptides of Formula (I) (SEQ ID No.: 39):

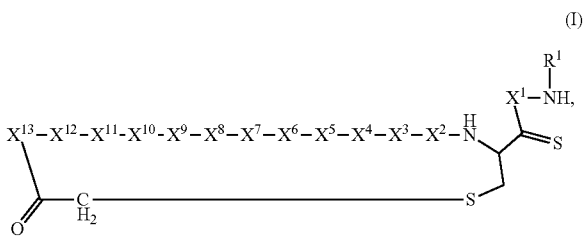

wherein:

$R^1$ is H or $(C_1-C_4)$alkyl;

$X^1$ is absent, Gly, Gly-L-Lys*, or Gly-D-Lys*, wherein * denotes the point of attachment to $NHR^1$;

$X^2$ is L-Pro or D-Pro;
$X^3$ is L-Arg, D-Arg, L-Ser, D-Ser, L-His, D-His, L-Ala, or D-Ala;
$X^4$ is L-Asp, D-Asp, L-Asn, D-Asn, L-Glu, D-Glu, L-Lys, D-Lys, L-Gln, D-Gln, L-Pro, D-Pro, L-Ala, D-Ala, L-(N-Me)Glu, or D-(N-Me)Glu;
$X^5$ is L-(N-Me)Ala, D-(N-Me)Ala, L-(N-Me)Glu, or D-(N-Me)Glu;
$X^6$ is L-Bip, D-Bip, L-(4-CF$_3$)Phe, D-(4-CF$_3$)Phe, L-(3,4-diCl)Phe, D-(3,4-diCl)Phe, L-(3-F)Phe, D-(3-F)Phe, L-(4-Cl)Phe, or D-(4-Cl)Phe;
$X^7$ is L-(N-Me)Ala, D-(N-Me)Ala, L-(N-Me)Phe, or D-(N-Me)Phe;
$X^8$ is L-Bip, D-Bip, L-Ser, D-Ser, L-Tyr, D-Tyr, L-(4-CF$_3$)Phe, D-(4-CF$_3$)Phe, L-Ala, D-Ala, L-Phe, D-Phe, L-Val, or D-Val;
$X^9$ is L-Thr or D-Thr;
$X^{10}$ is L-Thr, D-Thr, L-Ser, or D-Ser;
$X^{11}$ is L-Ser, D-Ser, L-Asp, D-Asp, L-Asn, D-Asn, L-Pro, D-Pro, L-Ala, D-Ala, L-Hse, or D-Hse;
$X^{12}$ is L-Val, D-Val, L-Glu or D-Glu; and
$X^{13}$ is L-Phe or D-Phe;
wherein:
Bip is 4-phenyl-phenylalanine;
Hse is homoserine;
(4-CF$_3$)Phe is 4-trifluoromethyl-phenylalanine;
(3,4-diCl)Phe is 3,4-dichloro-phenylalanine;
(3-F)Phe is 3-fluoro-phenylalanine; and
(4-Cl)Phe is 4-chloro-phenylalanine;
or pharmaceutically acceptable salts, hydrates, solvates, stereoisomers, or tautomers thereof.'

In one embodiment, the present disclosure relates to polypeptides of Formula (I) (SEQ ID No.: 40), wherein:
$R^1$ is H or (C$_1$-C$_4$)alkyl;
$X^1$ is absent or Gly;
$X^2$ is L-Pro or D-Pro;
$X^3$ is L-Arg, D-Arg, L-Ser, D-Ser, L-His, D-His, L-Ala, or D-Ala;
$X^4$ is L-Asp, D-Asp, L-Asn, D-Asn, L-Glu, D-Glu, L-Lys, D-Lys, L-Gln, D-Gln, L-Pro, D-Pro, L-Ala, D-Ala, L-(N-Me)Glu, or D-(N-Me)Glu;
$X^5$ is L-(N-Me)Ala, D-(N-Me)Ala, L-(N-Me)Glu, or D-(N-Me)Glu;
$X^6$ is L-Bip, D-Bip, L-(4-CF$_3$)Phe, D-(4-CF$_3$)Phe, L-(3,4-diCl)Phe, D-(3,4-diCl)Phe, L-(3-F)Phe, D-(3-F)Phe, L-(4-Cl)Phe, or D-(4-Cl)Phe;
$X^7$ is L-(N-Me)Ala, D-(N-Me)Ala, L-(N-Me)Phe, or D-(N-Me)Phe;
$X^8$ is L-Bip, D-Bip, L-Ser, D-Ser, L-Tyr, D-Tyr, L-(4-CF$_3$)Phe, D-(4-CF$_3$)Phe, L-Ala, D-Ala, L-Phe, D-Phe, L-Val, or D-Val;
$X^9$ is L-Thr or D-Thr;
$X^{10}$ is L-Thr, D-Thr, L-Ser, or D-Ser;
$X^{11}$ is L-Ser, D-Ser, L-Asp, D-Asp, L-Asn, D-Asn, L-Pro, D-Pro, L-Ala, D-Ala, L-Hse, or D-Hse;
$X^{12}$ is L-Val, D-Val, L-Glu or D-Glu; and
$X^{13}$ is L-Phe or D-Phe;
wherein:
Bip is 4-phenyl-phenylalanine;
Hse is homoserine;
(4-CF$_3$)Phe is 4-trifluoromethyl-phenylalanine;
(3,4-diCl)Phe is 3,4-dichloro-phenylalanine;
(3-F)Phe is 3-fluoro-phenylalanine; and
(4-Cl)Phe is 4-chloro-phenylalanine;
or pharmaceutically acceptable salts, hydrates, solvates, stereoisomers, or tautomers thereof.

Another aspect of the disclosure relates to a cyclic polypeptide of Formula (I), or a pharmaceutically acceptable salt thereof, for use in the treatment, prevention, amelioration or delay of progression of a PCSK9-mediated disease or disorder or for use in the treatment, prevention, amelioration or delay of progression of a disease or disorder requiring inhibition of PCSK9 or of PCSK9 activity In another aspect, the disclosure relates to the use of a cyclic polypeptide of Formula (I), or a pharmaceutically acceptable salt thereof, for the treatment, prevention, amelioration or delay of progression of a PCSK9-mediated disease or disorder or for the treatment, prevention, amelioration or delay of progression of a disease or disorder requiring inhibition of PCSK9 or of PCSK9 activity.

Another aspect of the disclosure relates to the use of a cyclic polypeptide of Formula (I), or a pharmaceutically acceptable salt thereof, in the manufacture of a medicament for the treatment, prevention, amelioration or delay of progression of a PCSK9-mediated disease or disorder or for the treatment, prevention, amelioration or delay of progression of a disease or disorder requiring inhibition of PCSK9 or of PCSK9 activity.

In another aspect, the disclosure relates a method for treating, preventing, ameliorating or delaying the progression of a PCSK9-mediated disease or disorder comprising the step of administering to a patient in need thereof a therapeutically effective amount of a cyclic polypeptide of Formula (I), or a pharmaceutically acceptable salt thereof, according to the disclosure, or a pharmaceutically acceptable salt thereof.

Another aspect of the disclosure relates to a method for treating, preventing, ameliorating or delaying the progression of a PCSK9-mediated disease or a disorder or of disease or disorder requiring inhibition of PCSK9 or of PCSK9 activity comprising the step of administering to a patient in need thereof a therapeutically effective amount of a cyclic polypeptide of Formula (I), or a pharmaceutically acceptable salt thereof, according to the disclosure, or a pharmaceutically acceptable salt thereof.

In another aspect, the disclosure relates a method of treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides comprising the step of administering to a patient in need thereof a therapeutically effective amount of a cyclic polypeptide of Formula (I), or a pharmaceutically acceptable salt thereof.

Another aspect of the disclosure relates to a method of (i) reducing Lp(a), (ii) reducing Lp(a) plasma levels, (iii) reducing Lp(a) serum levels, (iv) reducing serum TRL or LDL levels, (v) reducing serum triglyceride levels, (vi) reducing LDL-C, (vii) reducing total plasma apoB concentrations, (viii) reducing LDL apoB, (ix) reducing TRL apoB, or (x) reducing non HDL-C comprising the step of administering to a patient in need thereof a therapeutically effective amount of a cyclic polypeptide of Formula (I), or a pharmaceutically acceptable salt thereof.

In another aspect, the disclosure also relates to a method of (i) reducing LDL-C, (ii) reducing total apolipoprotein B (apoB) concentrations, (iii) reducing LDL apoB, (iv) reducing TRL apoB, or (v) reducing non HDL-C and combinations thereof, in a patient in need thereof, wherein the method comprising administering a therapeutically effective amount of a cyclic polypeptide of Formula (I), or a pharmaceutically acceptable salt thereof, to the patient.

Another aspect of the disclosure relates to a method of reducing the total plasma concentration of a marker selected from (i) LDL-C, (ii) apoB, (iii) LDL apoB, (iv) TRL apoB and (v) non HDL-C and combinations thereof, in a patient in need thereof, wherein the method comprising administering a therapeutically effective amount of a cyclic polypeptide of Formula (I), or a pharmaceutically acceptable salt thereof, to the patient.

In another aspect, the disclosure relates to a pharmaceutical composition comprising (e.g., a therapeutically effective amount of) a cyclic polypeptide of Formula (I), or a pharmaceutically acceptable salt thereof, and one or more pharmaceutically acceptable carriers or excipients.

Another aspect of the disclosure relates to a pharmaceutical composition comprising (e.g., a therapeutically effective amount of) a cyclic polypeptide of Formula (I), or a pharmaceutically acceptable salt thereof, and one or more pharmaceutically acceptable carriers or excipients for use in the treatment of a PCSK9-mediated disease or disorder.

In another aspect, the disclosure relates to a method of modulating PCSK9 comprising administering to a patient in need thereof a cyclic polypeptide of Formula (I), or a pharmaceutically acceptable salt thereof.

Another aspect of the disclosure relates to a method of inhibiting PCSK9 comprising administering to a patient in need thereof a cyclic polypeptide of Formula (I), or a pharmaceutically acceptable salt thereof. In another aspect, the disclosure relates to a method of inhibiting PCSK9 activity comprising administering to a patient in need thereof a cyclic polypeptide of Formula (I), or a pharmaceutically acceptable salt thereof.

In another aspect, the disclosure relates to a method for treating a PCSK9-mediated disease or disorder comprising the step of administering to a patient in need thereof a therapeutically effective amount of a cyclic polypeptide of Formula (I), or a pharmaceutically acceptable salt thereof.

Another aspect of the disclosure relates to a method of reducing LDL-C in a patient in need thereof, the method comprising administering a therapeutically effective amount of a cyclic polypeptide of Formula (I), or a pharmaceutically acceptable salt thereof to the patient, thereby reducing LDL-C in the patient.

In another aspect, the disclosure relates to a cyclic polypeptide of Formula (I), or a pharmaceutically acceptable salt thereof, for use in the treatment of a PCSK9-mediated disease or disorder.

Another aspect of the disclosure relates to a cyclic polypeptide of Formula (I), or a pharmaceutically acceptable salt thereof, for use in the treatment of a PCSK9-mediated disease or disorder which is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

In another aspect, the disclosure relates to the use of a cyclic polypeptide of Formula (I), or a pharmaceutically acceptable salt thereof, or a pharmaceutically acceptable salt thereof, in the manufacture of a medicament for treating a PCSK9-mediated disease or disorder.

Another aspect of the disclosure relates to a cyclic polypeptide of Formula (I), or a pharmaceutically acceptable salt thereof, for use in the manufacture of a medicament for treating a disease associated with inhibiting PCSK9 activity.

In another aspect, the disclosure relates to the use of a cyclic polypeptide of Formula (I), or a pharmaceutically acceptable salt thereof, in the treatment of a disease associated with the inhibition of PCSK9 activity.

In certain aspects, the PCSK9 modulating or inhibiting cyclic polypeptides of the disclosure may be administered alone or in combination with other compounds, including other PCSK9 modulating or inhibiting agents, or other therapeutic agents.

Accordingly, in another aspect, the disclosure relates to a combination, comprising (e.g. a therapeutically effective amount of) a cyclic polypeptide of formula (I), or a pharmaceutically acceptable salt thereof, and one or more therapeutically active agents.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar to or equivalent to those described herein can be used in the practice and testing of the disclosure, suitable methods and materials are described below. All publications, patent applications, patents, and other references mentioned herein are incorporated by reference. The references cited herein are not admitted to be prior art to the claimed disclosure. In the case of conflict, the present specification, including definitions, will control. In addition, the materials, methods, and examples are illustrative only and not intended to be limiting.

Other features and advantages of the disclosure will be apparent from the following detailed description and claims.

DETAILED DESCRIPTION OF THE DISCLOSURE

The disclosure relates to peptides and compositions that are capable of modulating the activity of PCSK9. The disclosure features methods of treating, preventing or ameliorating a disease or disorder in which PCSK9 plays a role by administering to a patient in need thereof a therapeutically effective amount of a cyclic polypeptide of Formula (I), or a pharmaceutically acceptable salt, hydrate, solvate, stereoisomer, or tautomer thereof. The methods of the disclosure can be used in the treatment of a variety of PCSK9 dependent diseases and disorders by modulating or inhibiting PCSK9. Inhibition or modulation of PCSK9 provides a novel approach to the treatment, prevention, or amelioration of diseases including, but not limited to, hypercholesterolemia, hyperlipidemia, hypertriglyceridemia, sitosterolemia, atherosclerosis, arteriosclerosis, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, and xanthoma.

The cyclic polypeptides of the disclosure, by inhibiting PCSK9, have utility in the treatment of hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL (e.g., elevated VLDL and/or chylomicrons), elevated triglycerides, sepsis, and xanthoma.

For example, the cyclic polypeptides of formula (I) of the disclosure bind to PCSK9 and thereby inhibit PCSK9 and/or PCSK9 activity, since PCSK9 cannot any longer bind to the low density lipoprotein receptors (LDLR) or any other target receptors. For example, if PCSK9 is blocked, more LDLRs are recycled and are present on the surface of cells to remove LDL-particles from the extracellular fluid. Therefore, blocking PCSK9 can lower blood LDL-particle concentrations.

Accordingly, polypeptides of the disclosure may therefore be potentially useful in the treatment, prevention, amelioration or delay of progression of a PCSK9-mediated disease or disorder, or a disease or disorder in which PCSK9 plays a role, as well as conditions, diseases and disorders benefitting from modulating PCSK9 or PCSK9 activity.

In addition, cyclic polypeptides of the disclosure may therefore be potentially useful in the treatment, prevention, amelioration or delay of progression of a disease or disorder requiring inhibition of PCSK9 or of PCSK9 activity.

Such diseases and disorders include diseases or disorders selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL (e.g., elevated VLDL and/or chylomicrons), elevated triglycerides, sepsis, and xanthoma.

Various embodiments of the disclosure are described herein. It will be recognized that features specified in each embodiment may be combined with other specified features of other embodiments to provide further embodiments.

In a first aspect of the disclosure, the cyclic polypeptides of Formula (I) are described:

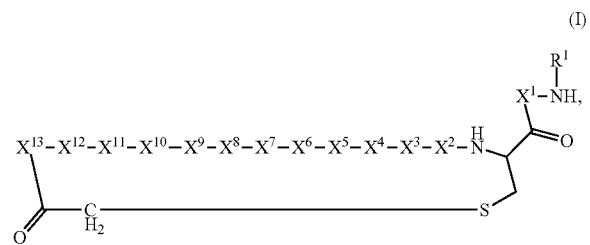

(I)

and pharmaceutically acceptable salts, hydrates, solvates, stereoisomers, and tautomers thereof, wherein $R^1$, $X^1$, $X^2$, $X^3$, $X^4$, $X^5$, $X^6$, $X^7$, $X^8$, $X^9$, $X^{10}$, $X^{11}$, $X^{12}$, and $X^{13}$ are as described herein above.

The details of the disclosure are set forth in the accompanying description below. Although methods and materials similar or equivalent to those described herein can be used in the practice or testing of the disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

Chemical Nomenclature, Terms, and Conventions

Unless otherwise specified, conventional definitions of terms control and conventional stable atom valences are presumed and achieved in all formulas and groups.

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

"Alkyl" means a straight or branched chain saturated hydrocarbon containing 1-12 carbon atoms. Examples of a ($C_1$-$C_6$)alkyl group include, but are not limited to, methyl, ethyl, propyl, butyl, pentyl, hexyl, isopropyl, isobutyl, sec-butyl, tert-butyl, isopentyl, neopentyl, and isohexyl.

As used herein, the terms "polypeptide" and "peptide" are used interchangeably to refer to two or more amino acids linked together. Except for the abbreviations for the uncommon or unnatural amino acids set forth in Table 1 below, the art-recognized three letter or one letter abbreviations are used to represent amino acid residues that constitute the peptides and polypeptides of the disclosure. When preceded with "D," the amino acid is an D-amino acid. When preceded with "L," the amino acid is an L-amino acid. When the one letter abbreviation is a capital letter, it refers to the L-amino acid. When the one letter abbreviation is a lower case letter, it refers to the D-amino acid. Groups or strings of amino acid abbreviations are used to represent peptides. Peptides are indicated with the N-terminus on the left and the sequence is written from the N-terminus to the C-terminus.

Any of the above-listed amino acid residues of Formula (I), or its related formulae described herein, e.g., Formulae (I), (II), (III), (IV), (V), and (VI), may be substituted in a conservative fashion, provided the peptide or polypeptide of the disclosure still retains functional activity and structural properties (e.g., half-life extension, protection from degradation, conformational constraint). Principle and examples of permissible conservative amino acid substitutions are further explained herein.

Peptides of the disclosure contain non-natural amino acids (i.e., compounds that do not occur in nature) and other amino acid analogs as are known in the art may alternatively be employed.

One of ordinary skill in the art will appreciate that various amino acid substitutions, e.g., conservative amino acid substitutions, may be made in the sequence of any of the cyclic polypeptides described herein, without necessarily decreasing its activity. As used herein, "amino acid commonly used as a substitute thereof" includes conservative substitutions (i.e., substitutions with amino acids of comparable chemical characteristics). For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-natural amino acids having an amino containing side chain, or substituting an alanine for norvaline or the like.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" refers to materials which are found in nature and are not manipulated by man. Similarly, "non-naturally occurring," "un-natural," and the like, as used herein, refers to a material that is not found in nature or that has been structurally modified or synthesized by man. When used in connection with amino acids, the term "naturally occurring" refers to the 20 conventional amino acids (i.e., alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp), and tyrosine (Y or Tyr)).

The terms "non-natural amino acid" and "unnatural amino acid," as used herein, are interchangeably intended to represent amino acid structures that cannot be generated biosynthetically in any organism using unmodified or modified genes from any organism, whether the same or different. These include, but are not limited to, modified amino acids and/or amino acid analogues that are not one of the 20 naturally occurring amino acids, selenocysteine, pyrrolysine (Pyl), or pyrroline-carboxy-lysine (Pcl, e.g., as described in PCT patent publication WO2010/48582).

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentyglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

Peptides are defined herein as organic compounds comprising two or more amino acids covalently joined by peptide bonds. Peptides may be referred to with respect to the number of constituent amino acids, i.e., a dipeptide or dimer contains two amino acid residues, a tripeptide or trimer contains three, etc. Peptides containing ten or fewer amino acids may be referred to as oligopeptides, while those with more than ten amino acid residues are polypeptides.

The term "peptide" as used herein means two or more amino acids that are linked together via a peptide bond.

TABLE 1

Examples of un-natural or non-natural Amino Acids as described in the disclosure:

| Symbol | Chemical Name | Structure |
|---|---|---|
| (p-Cl)F or (4-Cl)F or (4-Cl)Phe | 2-amino-3-(4-chlorophenyl)propanoic acid or 4-chloro-phenylalanine | 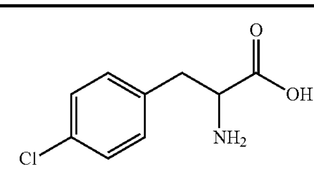 |
| (p-F)F or (3-F)F or (3-F)Phe | 2-amino-3-(3-fluorophenyl)propanoic acid or 3-fluoro-phenylalanine | 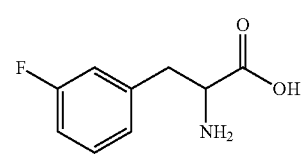 [SMILES: NC(Cc1cccc(F)c1)C(=O)O] |
| (p-CF$_3$)F or (4-CF$_3$)F or (4-CF$_3$)Phe | 2-amino-3-(4-(trifluoromethyl)phenyl)propanoic acid or 4-trifluoromethyl-phenylalanine | 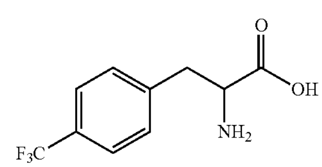 [SMILES: NC(Cc1ccc(C(F)(F)F)cc1)C(=O)O] |
| (3,4-diCl)F or (3,4-diCl)Phe | 2-amino-3-(3,4-dichlorophenyl)propanoic acid or 3,4-dichloro-phenylalanine | 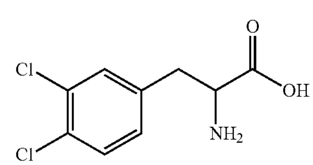 [SMILES: NC(Cc1ccc(Cl)c(Cl)c1)C(=O)O] |

TABLE 1-continued

Examples of un-natural or non-natural Amino Acids as described in the disclosure:

| Symbol | Chemical Name | Structure |
|---|---|---|
| B or Bip | 3-([1,1'-biphenyl]-4-yl)-2-aminopropanoic acid or 4-phenyl-phenylalanine | 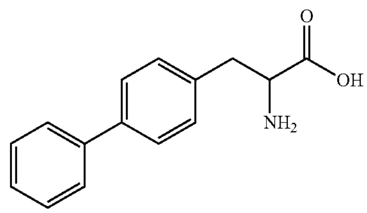 [SMILES: NC(Cc1ccc(-c2ccccc2)cc1)C(=O)O] |
| (N-Me)A | N-methylalanine | 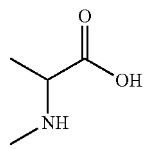 |
| (N-Me)E | N-Methylglutamic acid | 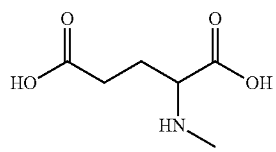 |
| (N-Me)F | N-methylphenylalanine | 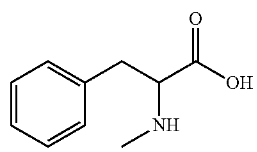 |
| HomoSer or Hse | homoserine | 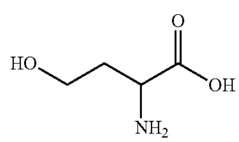 |

TABLE 2

Examples of Protected Amino Acids as described in the disclosure:

| Symbol | Name | Structure |
|---|---|---|
| T(tBu) | O-(tert-butyl)threonine | 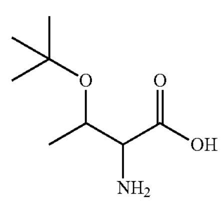 |
| E(tBu) | 2-amino-5-(tert-butoxy)-5-oxopentanoic acid | 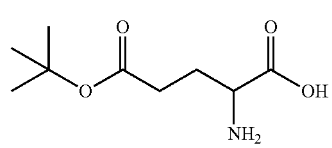 |

TABLE 2-continued

Examples of Protected Amino Acids as described in the disclosure:

| Symbol | Name | Structure |
|---|---|---|
| S(tBu) | O-(tert-butyl)serine | 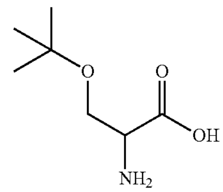 |
| D(tBu) | 2-amino-4-(tert-butoxy)-4-oxobutanoic acid | 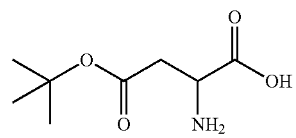 |
| C(Trt) | Trityl-cysteine | 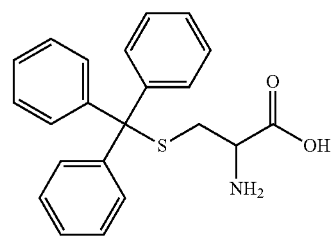 [SMILES: NC(CSC(c1ccccc1)(c1ccccc1)c1ccccc1)C(=O)O] |
| (N-Me)E(tBu) | 5-(tert-butoxy)-2-(N-methylamino)-5-oxopentanoic acid | 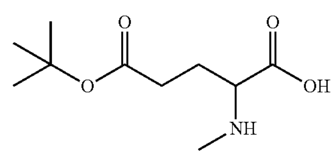 |
| K(Boc) | $N^6$-(tert-butoxycarbonyl)lysine | 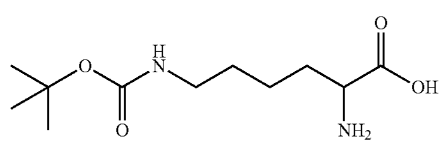 [SMILES: CC(C)(C)OC(=O)NCCCCC(N)C(=O)O] |
| R(Pbf) | $N^\omega$-((2,2,4,6,7-pentamethyl-2,3-dihydrobenzofuran-5-yl)sulfonyl)arginine | 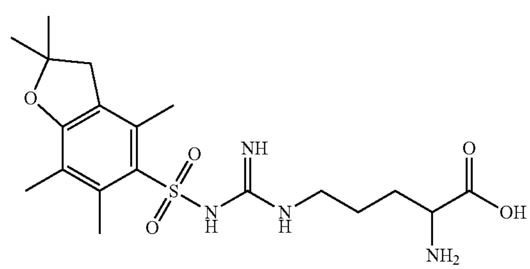 [SMILES: Cc1c(C)c(S(=O)(=O)NC(=N)NCCCC(N)C(=O)O)c(C)c2c1OC(C)(C)C2] |

Salt, Prodrug, Derivative, and Solvate Terms and Conventions

"Prodrug" or "prodrug derivative" mean a covalently-bonded derivative or carrier of the parent polypeptide or active drug substance which undergoes at least some biotransformation prior to exhibiting its pharmacological effect(s). In general, such prodrugs have metabolically cleavable groups and are rapidly transformed in vivo to yield the parent polypeptide, for example, by hydrolysis in blood, and generally include esters and amide analogs of the parent polypeptides. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent polypeptides using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

"Pharmaceutically acceptable prodrug" as used herein means a prodrug of a polypeptide of the disclosure which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

"Salt" means an ionic form of the parent polypeptide or the product of the reaction between the parent polypeptide with a suitable acid or base to make the acid salt or base salt of the parent polypeptide. Salts of the polypeptides of the disclosure can be synthesized from the parent polypeptides which contain a basic or acidic moiety by conventional chemical methods. Generally, the salts are prepared by reacting the free base or acid parent polypeptide with stoichiometric amounts or with an excess of the desired salt-forming inorganic or organic acid or base in a suitable solvent or various combinations of solvents.

"Pharmaceutically acceptable salt" means a salt of a polypeptide of the disclosure which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the polypeptides of the disclosure are useful in both free base and salt form, in practice, the use of the salt form amounts to use of the base form. Lists of suitable salts are found in, e.g., S. M. Birge, et. al., J. Pharm. Sci., 1977, 66, pp. 1-19, which is hereby incorporated by reference in its entirety.

"Pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

"Pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

"Solvate" means a complex of variable stoichiometry formed by a solute, for example, a polypeptide of Formula (I) and solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, such solvents selected for the purpose of the disclosure do not interfere with the biological activity of the solute. Solvates encompasses both solution-phase and isolatable solvates. Representative solvates include hydrates, ethanolates, methanolates, and the like.

"Hydrate" means a solvate wherein the solvent molecule(s) is/are water.

The polypeptides of the disclosure as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

Isomer Terms and Conventions

"Isomers" means compounds or polypeptides having the same number and kind of atoms, and hence the same molecular weight, but differing with respect to the arrangement or configuration of the atoms in space. The term includes stereoisomers and geometric isomers.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the polypeptides of the disclosure which may give rise to stereoisomerism, the disclosure contemplates stereoisomers and mixtures thereof. The polypeptides of the disclosure and their salts include asymmetric carbon atoms and may therefore exist as single stereoisomers, racemates, and as mixtures of enantiomers and diastereomers. Typically, such compounds or polypeptides will be prepared as a racemic mixture. If desired, however, such compounds or polypeptides can be prepared or isolated as pure stereoisomers, i.e., as individual enantiomers or diastereomers, or as stereoisomer-enriched mixtures. As discussed in more detail below, individual stereoisomers of compounds or polypeptides are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds or amino acids of particular stereochemistry are either commercially available or are made by the methods described below and resolved by techniques well-known in the art.

"Enantiomers" means a pair of stereoisomers that are non-superimposable mirror images of each other.

"Diastereoisomers" or "diastereomers" mean optical isomers which are not mirror images of each other.

"Racemic mixture" or "racemate" mean a mixture containing equal parts of individual enantiomers.

"Non-racemic mixture" means a mixture containing unequal parts of individual enantiomers.

Some of the polypeptides of the disclosure can exist in more than one tautomeric form. As mentioned above, the polypeptides of the disclosure include all such tautomers.

It is well-known in the art that the biological and pharmacological activity of a compound or polypeptide is sensitive to the stereochemistry of the compound or polypeptide. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the polypeptides of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

Pharmaceutical Administration and Treatment Terms and Conventions

A "patient" or "subject" is a mammal, e.g., a human, mouse, rat, guinea pig, dog, cat, horse, cow, pig, or nonhuman primate, such as a monkey, chimpanzee, baboon or, rhesus. In certain embodiments, the subject is a primate. In yet other embodiments, the subject is a human.

The terms "pharmaceutically effective amount" or "therapeutically effective amount" or "effective amount" means an amount of a polypeptide according to the disclosure which, when administered to a patient in need thereof, is sufficient to effect treatment for disease-states, conditions, or disorders for which the polypeptides have utility. Such an amount would be sufficient to elicit the biological or medical response of a tissue, system, or patient that is sought by a researcher or clinician. The amount of a polypeptide of according to the disclosure which constitutes a therapeutically effective amount will vary depending on such factors as the polypeptide and its biological activity, the composition used for administration, the time of administration, the route of administration, the rate of excretion of the polypeptide, the duration of treatment, the type of disease-state or disorder being treated and its severity, drugs used in combination with or coincidentally with the polypeptides of the disclosure, and the age, body weight, general health, sex, and diet of the patient. Such a therapeutically effective amount can be determined routinely by one of ordinary skill in the art having regard to their own knowledge, the prior art, and this disclosure.

As used herein, the term "pharmaceutical composition" refers to a polypeptide of the disclosure, or a pharmaceutically acceptable salt, hydrate, solvate, stereoisomer, or tautomer thereof, together with at least one pharmaceutically acceptable carrier, in a form suitable for oral or parenteral administration.

"Carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

"Combination" refers to either a fixed combination in one dosage unit form, or a combined administration where a cyclic polypeptide of the disclosure and at least one combination partner (e.g. another drug as explained below, also referred to as "therapeutic agent" or "co-agent") may be administered independently at the same time or separately within time intervals, especially where these time intervals allow that the combination partners show a beneficial effect from the co-action of these therapeutic agents. The beneficial effect of the combination includes, but is not limited to, a cooperative, e.g., synergistic, effect and/or a pharmacokinetic or pharmacodynamic co-action, or any combination thereof, resulting from the combination of therapeutic agents. In one embodiment, administration of these therapeutic agents in combination is carried out over a defined time period (e.g., minutes, hours, days or weeks depending upon the combination selected). "

The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a cyclic polypeptide of the disclosure and a combination partner, are both administered to a patient simultaneously in the form of a single entity or dosage. The term "non-fixed combination" means that the therapeutic agents, e.g., a cyclic polypeptide of the disclosure and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agents.

A subject is "in need of" a treatment if such subject would benefit biologically, medically, or in quality of life from such treatment (preferably, a human).

The term "PCSK9" or "proprotein convertase subtilisin/kexin type 9" interchangeably refer to a naturally occurring human proprotein convertase belonging to the proteinase K subfamily of the secretory subtilase family. PCSK9 is synthesized as a soluble zymogen that undergoes autocatalytic intramolecular processing in the endoplasmic reticulum, and is thought to function as a proprotein convertase. PCSK9 plays a role in cholesterol homeostasis and may have a role in the differentiation of cortical neurons. Mutations in the PCSK9 gene are a cause of autosomal dominant familial hypercholesterolemia. (Burnett and Hooper, Clin. Biochem. Rev. (2008) 29(1):11-26)

As used herein, the term "inhibit", "inhibition", or "inhibiting" refers to the reduction or suppression of a given condition, symptom, or disorder, or disease, or a significant decrease in the baseline activity of a biological activity or process.

As used herein, the term "treat", "treating", or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing", or "prevention" of any disease or disorder refers to the prophylactic treatment of the disease or disorder; or delaying the onset or progression of the disease or disorder.

"Pharmaceutically acceptable" means that the substance or composition must be compatible chemically and/or toxicologically, with the other ingredients comprising a formulation, and/or the mammal being treated therewith.

"Disorder" means, and is used interchangeably with, the terms disease, condition, or illness, unless otherwise indicated.

"Administer", "administering", or "administration" means to either directly administering a disclosed polypeptide or pharmaceutically acceptable salt of the disclosed polypeptide or a composition to a subject, or administering a prodrug derivative or analog of the polypeptide or pharmaceutically acceptable salt of the polypeptide or composition to the subject, which can form an equivalent amount of active polypeptide within the subject's body.

"Prodrug" means a polypeptide which is convertible in vivo by metabolic means (e.g., by hydrolysis) to a disclosed polypeptide.

"Polypeptides of the disclosure", "polypeptides of Formula (I)", "polypeptides of the disclosure", "cyclic polypeptides of the disclosure", "cyclic polypeptides of Formula (I)", "cyclic polypeptides of the disclosure", and equivalent expressions (unless specifically identified otherwise) refer to polypeptides of Formula (I), (II), (III), (IV), (V), and (VI) as herein described including the tautomers, the prodrugs, salts particularly the pharmaceutically acceptable salts, and the solvates and hydrates thereof, where the context so permits thereof, as well as all stereoisomers (including diastereoisomers and enantiomers), rotamers, tautomers, and isotopically labelled polypeptides (including deuterium substitutions), as well as inherently formed moieties (e.g., solvate, and/or hydrates). For purposes of this disclosure, solvates and hydrates are generally considered compositions. In general and preferably, the polypeptides of the disclosure and the formulas designating the polypeptides of the disclosure are understood to only include the stable polypeptides thereof and exclude unstable polypeptides, even if an unstable polypeptide might be considered to be literally embraced by the polypeptide formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

"Stable polypeptide" or "stable structure" means a polypeptide that is sufficiently robust to survive isolation to a useful degree of purity from a reaction mixture, and formulation into an efficacious therapeutic or diagnostic agent. For example, a polypeptide which would have a "dangling valency" or is a carbanion is not a polypeptide contemplated by the disclosure.

In a specific embodiment, the term "about" or "approximately" means within 20%, preferably within 10%, and more preferably within 5% of a given value or range.

As used herein, a "modulator of PCSK9" refers to a peptide or polypeptide that is able to modulate PCSK9 biological activity or function, and/or downstream pathway(s) mediated by PCSK9 activity.

As used herein, an "inhibitor of PCSK9" refers to a peptide or polypeptide that is able to inhibit PCSK9 biological activity or function, and/or downstream pathway(s) mediated by PCSK9 signaling. An inhibitor of PCSK9 activity encompasses polypeptides that block, antagonize, suppress or reduce (to any degree including significantly) PCSK9 biological activity, including downstream pathways mediated by PCSK9 activity.

As used herein, "disorders or diseases responsive to the inhibition of PCSK9," "disorders and conditions responsive to the inhibition of PCSK9," "disorders and conditions responsive to the inhibition of PCSK9 activity," "disorders responsive to the inhibition of PCSK9," "disorders responsive to the inhibition of PCSK9 activity," "disorders in which PCSK plays a role," and like terms include hypercholesterolemia, hyperlipidemia, hypertriglyceridemia, sitosterolemia, atherosclerosis, arteriosclerosis, coronary heart disease, peripheral vascular disease (including aortic diseases and cerebrovascular disease), peripheral arterial disease, vascular inflammation, elevated Lp(a), elevated LDL, elevated TRL, elevated triglycerides, sepsis, and xanthoma.

As used herein, "Inhibition of PCSK9 activity," or "inhibition of PCSK9," refers to a decrease in the PCSK9 activity, e.g., by administration of the peptides and polypeptides of the disclosure.

The term "hypercholesterolemia" or "dyslipidemia" includes, e.g., familial and non-familial hypercholesterolemia. Familial hypercholesterolemia (FH) is an autosomal dominant disorder characterized by elevation of serum cholesterol bound to low density lipoprotein (LDL). Familial hypercholesterolemia includes both heterozygous FH and homozygous FH. Hypercholesterolemia (or dyslipidemia) is the presence of high levels of cholesterol in the blood. It is a form of hyperlipidemia (elevated levels of lipids in the blood) and hyperlipoproteinemia (elevated levels of lipoproteins in the blood).

Hyperlipidemia is an elevation of lipids in the bloodstream. These lipids include cholesterol, cholesterol esters, phospholipids and triglycerides. Hyperlipidemia includes for example, type I, IIa, IIb, III, IV and V.

Hypertriglyceridemia denotes high blood levels of triglycerides. Elevated levels of triglycerides are associated with atherosclerosis, even in the absence of hypercholesterolemia, and predispose to cardiovascular disease.

"Sitosterolemia" or "phytosterolemia" is a rare autosomal recessively inherited lipid metabolic disorder characterized by hyperabsorption of sitosterol from the gastrointestinal tract and decreased biliary excretion of dietary sterols (i.e., leading to hypercholesterolemia, tendon and tuberous xanthomas, premature development of atherosclerosis) and altered cholesterol synthesis.

"Atherosclerosis" includes hardening of arteries associated with deposition of fatty substances, cholesterol, cellular waste products, calcium and fibrin in the inner lining of an artery. The buildup that results is called plaque.

"Atherosclerosis" or "arteriosclerotic vascular disease (ASVD)" is a specific form of arteriosclerosis involving thickening, hardening and loss of elasticity of the walls of arteries as a result of invasion and accumulation of white blood cells, containing both living, active white blood cells (producing inflammation) and remnants of dead cells, including cholesterol and triglycerides. Atherosclerosis is therefore a syndrome affecting arterial blood vessels due to a chronic inflammatory response of white blood cells in the walls of arteries.

"Coronary heart disease," also known as atherosclerotic artery disease, atherosclerotic cardiovascular disease, coronary heart disease or ischemic heart disease is the most common type of heart disease and cause of heart attacks. The disease is caused by plaque building up along the inner walls of the arteries of the heart, which narrows the lumen of arteries and reduces blood flow to the heart.

"Xanthoma" is a cutaneous manifestation of lipidosis in which lipids accumulate in large foam cells within the skin. Xanthomas are associated with hyperlipidemias.

The term "elevated Lp(a) concentration", as used herein, refers to a serum Lp(a) concentration above 30 mg/dl (75 nmol/L). "Elevated serum Lp(a)" means a serum Lp(a) level greater than about 14 mg/dL. In certain embodiments, a patient is considered to exhibit elevated serum Lp(a) if the level of serum Lp{a) measured in the patient is greater than about 15 mg/dL, about 20 mg/dL, about 25 mg/dL, about 30 mg/dL, about 35 mg/dL, about 40 mg/dL, about 45 mg/dL, about 50 mg/dL, about 60 mg/dL, about 70 mg/dL, about 80 mg/dL, about 90 mg/dL, about 100 mg/dL, about 20 mg/dL, about 140 mg/dL, about 150 mg dL, about 180 mg/dL, or about 200 mg/dL The serum Lp(a) level can be measured in a patient post-prandial. In some embodiments, the Lp(a) level is measured after a period of time of fasting (e.g., after fasting for 8 hrs, 8 hrs, 10 hrs, 12 hrs or more). Exemplary methods for measuring serum Lp(a) in a patient include, but are not limited to, rate immunonephelometry, ELISA, nephelometry, immunoturbidimetry, and dissociation-enhanced lanthanide fluorescent immunoassay, although any clinically acceptable diagnostic method can be used in the context of the disclosure.

By "elevated triglyceride levels" or "ETL" is meant any degree of triglyceride levels that is determined to be undesirable or is targeted for modulation.

"Sepsis" is a systemic reaction characterized by arterial hypotension, metabolic acidosis, decreased systemic vascular resistance, tachypnea, and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms.

Specific Embodiments of Polypeptides of Formula (I)

The disclosure relates to polypeptides or pharmaceutically acceptable salts, hydrates, solvates, prodrugs, stereoisomers, or tautomers thereof, capable of modulating PCSK9, which are useful for the treatment of diseases and disorders associated with modulation of a PCSK9 protein or enzyme. In another embodiment, the disclosure relates to polypeptides or pharmaceutically acceptable salts, hydrates, solvates, prodrugs, stereoisomers, or tautomers thereof, capable of inhibiting PCSK9, which are useful for the treatment of diseases and disorders associated with inhibition of a PCSK9 protein or enzyme. The disclosure further relates to polypeptides, or pharmaceutically acceptable salts, hydrates, solvates, prodrugs, stereoisomers, or tautomers thereof, which are useful for inhibiting PCSK9.

In one embodiment, the polypeptides of Formula (I) have the structure of Formula (II): Formula (II) (SEQ ID No.: 44):

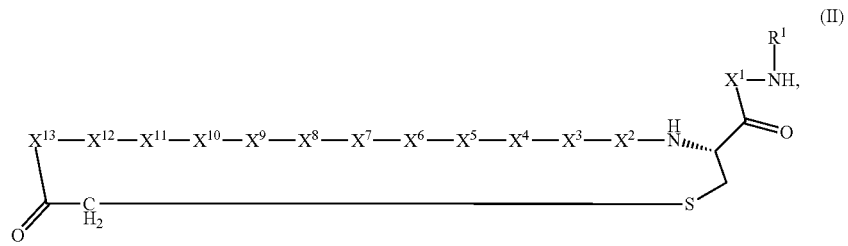

and pharmaceutically acceptable salts, hydrates, solvates, prodrugs, stereoisomers, and tautomers thereof.

In another embodiment, the polypeptides of Formula (I) have the structure of Formula (III) (SEQ ID No.: 45):

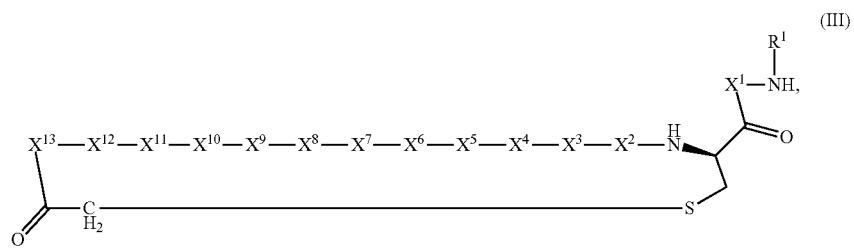

and pharmaceutically acceptable salts, hydrates, solvates, prodrugs, stereoisomers, and tautomers thereof.

In another embodiment, the polypeptides of Formula (I) have the structure of Formula (IV) (SEQ ID No.: 46):

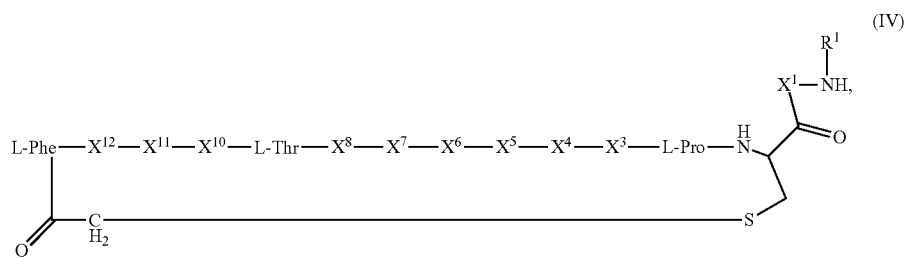

and pharmaceutically acceptable salts, hydrates, solvates, prodrugs, stereoisomers, and tautomers thereof.

In another embodiment, the polypeptides of Formula (I) have the structure of Formula (V) (SEQ ID No.: 47):

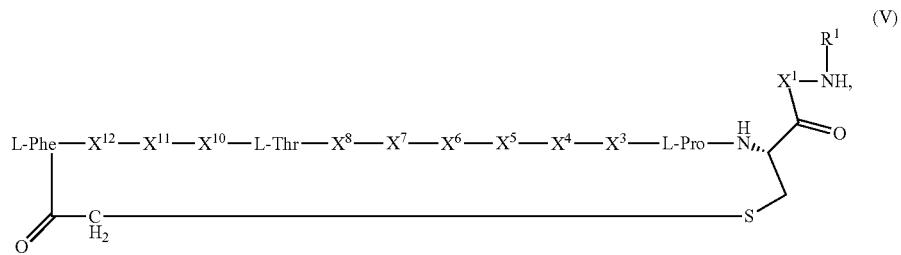

and pharmaceutically acceptable salts, hydrates, solvates, prodrugs, stereoisomers, and tautomers thereof.

In another embodiment, the polypeptides of Formula (I) have the structure of Formula (VI) (SEQ ID No.: 48):

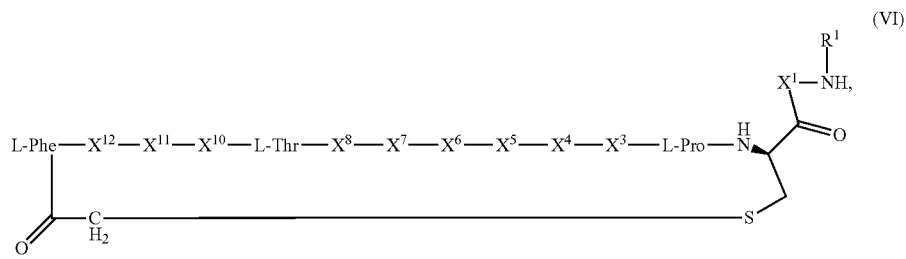

and pharmaceutically acceptable salts, hydrates, solvates, prodrugs, stereoisomers, and tautomers thereof.

In some embodiments of the Formulae above (i.e., Formula (I), Formula (II), Formula (III), Formula (IV), Formula (V), and/or Formula (VI)), $R^1$ is H or $(C_1$-$C_3)$alkyl. In another embodiment, $R^1$ is methyl or ethyl. In another embodiment, $R^1$ is H. In yet another embodiment, $R^1$ is H, methyl, or ethyl.

In some embodiments of the Formulae above, $X^1$ is absent or Gly. In another embodiment, $X^1$ is absent, Gly-L-Lys*, or Gly-D-Lys*. In another embodiment, $X^1$ is absent, Gly, or Gly-L-Lys*. In another embodiment, $X^1$ is absent, Gly, or Gly-D-Lys*. In another embodiment, $X^1$ is Gly-L-Lys* or Gly-D-Lys*. In another embodiment, $X^1$ is Gly. In another embodiment, $X^1$ is absent.

In some embodiments of the Formulae above, $X^2$ is D-Pro. In another embodiment, $X^2$ is L-Pro.

In some embodiments of the Formulae above, $X^3$ is D-Arg, D-Ser, D-His, or D-Ala. In another embodiment, $X^3$ is L-Arg, L-Ser, L-His, or L-Ala. In yet another embodiment, $X^3$ is L-Arg, L-Ser, or L-His. In another embodiment, $X^3$ is L-Arg, L-His, or L-Ala. In yet another embodiment, $X^3$ is L-Ser, L-His, or L-Ala. In another embodiment, $X^3$ is L-His or L-Ala. In yet another embodiment, $X^3$ is L-Arg or L-Ser. In another embodiment, $X^3$ is L-Ser or L-Ala. In yet another embodiment, $X^3$ is L-Arg or L-Ala. In another embodiment, $X^3$ is L-Arg, L-Ser, or L-Ala.

In some embodiments of the Formulae above, $X^4$ is D-Asp, D-Asn, D-Glu, D-Lys, D-Gln, D-Pro, D-Ala, or D-(N-Me)Glu. In another embodiment, $X^4$ is L-Asp, L-Asn, D-Asn, L-Glu, D-Glu, L-Lys, D-Lys, L-Gln, D-Gln, L-Pro, D-Pro, L-Ala, D-Ala, L-(N-Me)Glu, or D-(N-Me)Glu. In yet another embodiment, $X^4$ is L-Asp, D-Asp, L-Asn, L-Glu, D-Glu, L-Lys, D-Lys, L-Gln, D-Gln, L-Pro, D-Pro, L-Ala, D-Ala, L-(N-Me)Glu, or D-(N-Me)Glu. In another embodiment, $X^4$ is L-Asp, D-Asp, L-Asn, D-Asn, L-Glu, L-Lys, D-Lys, L-Gln, D-Gln, L-Pro, D-Pro, L-Ala, D-Ala, L-(N-Me)Glu, or D-(N-Me)Glu. In yet another embodiment, $X^4$ is L-Asp, D-Asp, L-Asn, D-Asn, L-Glu, D-Glu, L-Lys, L-Gln, D-Gln, L-Pro, D-Pro, L-Ala, D-Ala, L-(N-Me)Glu, or D-(N-Me)Glu. In another embodiment, $X^4$ is L-Asp, D-Asp, L-Asn, D-Asn, L-Glu, D-Glu, L-Lys, D-Lys, L-Gln, L-Pro, D-Pro, L-Ala, D-Ala, L-(N-Me)Glu, or D-(N-Me)Glu. In yet another embodiment, $X^4$ is L-Asp, D-Asp, L-Asn, D-Asn, L-Glu, D-Glu, L-Lys, D-Lys, L-Gln, D-Gln, L-Pro, L-Ala, D-Ala, L-(N-Me)Glu, or D-(N-Me)Glu.

In another embodiment, $X^4$ is L-Asp, D-Asp, L-Asn, D-Asn, L-Glu, D-Glu, L-Lys, D-Lys, L-Gln, D-Gln, L-Pro, D-Pro, L-Ala, L-(N-Me)Glu, or D-(N-Me)Glu. In yet another embodiment, $X^4$ is L-Asp, D-Asp, L-Asn, D-Asn, L-Glu, D-Glu, L-Lys, D-Lys, L-Gln, D-Gln, L-Pro, D-Pro, L-Ala, D-Ala, or L-(N-Me)Glu. In another embodiment, $X^4$ is L-Asn, L-Glu, L-Lys, L-Gln, L-Pro, L-Ala, or L-(N-Me)Glu. In yet another embodiment, $X^4$ is L-Asp, L-Glu, L-Lys, L-Gln, L-Pro, L-Ala, or L-(N-Me)Glu. In another embodiment, $X^4$ is L-Asp, L-Asn, L-Lys, L-Gln, L-Pro, L-Ala, or L-(N-Me)Glu. In yet another embodiment, $X^4$ is L-Asp, L-Asn, L-Glu, L-Gln, L-Pro, L-Ala, or L-(N-Me)Glu. In another embodiment, $X^4$ is L-Asp, L-Asn, L-Glu, L-Lys, L-Pro, L-Ala, or L-(N-Me)Glu. In yet another embodiment, $X^4$ is L-Asp, L-Asn, L-Glu, L-Lys, L-Gln, L-Ala, or L-(N-Me)Glu. In another embodiment, $X^4$ is L-Asp, L-Asn, L-Glu, L-Lys, L-Gln, L-Pro, or L-(N-Me)Glu. In yet another embodiment, $X^4$ is L-Asp, L-Asn, L-Glu, L-Lys, L-Gln, L-Pro, or L-Ala. In another embodiment, $X^4$ is L-Asp, L-Asn, L-Glu, L-Lys, L-Gln, L-Pro, L-Ala, or L-(N-Me)Glu.

In some embodiments of the Formulae above, $X^5$ is D-(N-Me)Ala, L-(N-Me)Glu, or D-(N-Me)Glu. In another embodiment, $X^5$ is L-(N-Me)Ala, L-(N-Me)Glu, or D-(N-Me)Glu. In yet another embodiment, $X^5$ is L-(N-Me)Ala, D-(N-Me)Ala, or D-(N-Me)Glu. In another embodiment, $X^5$ is L-(N-Me)Ala, D-(N-Me)Ala, or L-(N-Me)Glu. In yet another embodiment, $X^5$ is D-(N-Me)Ala or D-(N-Me)Glu. In another embodiment, $X^5$ is L-(N-Me)Ala or L-(N-Me)Glu.

In some embodiments of the Formulae above, $X^6$ is D-Bip, L-(4-$CF_3$)Phe, D-(4-$CF_3$)Phe, L-(3,4-diCl)Phe, D-(3,4-diCl)Phe, L-(3-F)Phe, D-(3-F)Phe, L-(4-Cl)Phe, or D-(4-Cl)Phe. In another embodiment, $X^6$ is L-Bip, L-(4-$CF_3$)Phe, D-(4-$CF_3$)Phe, L-(3,4-diCl)Phe, D-(3,4-diCl)Phe, L-(3-F)Phe, D-(3-F)Phe, L-(4-Cl)Phe, or D-(4-Cl)Phe. In yet another embodiment, $X^6$ is L-Bip, D-Bip, D-(4-$CF_3$)Phe, L-(3,4-diCl)Phe, D-(3,4-diCl)Phe, L-(3-F)Phe, D-(3-F)Phe, L-(4-Cl)Phe, or D-(4-Cl)Phe. In another embodiment, $X^6$ is L-Bip, D-Bip, L-(4-$CF_3$)Phe, L-(3,4-diCl)Phe, D-(3,4-diCl)Phe, L-(3-F)Phe, D-(3-F)Phe, L-(4-Cl)Phe, or D-(4-Cl)Phe. In another embodiment, $X^6$ is L-Bip, D-Bip, L-(4-$CF_3$)Phe, D-(4-$CF_3$)Phe, D-(3,4-diCl)Phe, L-(3-F)Phe, D-(3-F)Phe, L-(4-Cl)Phe, or D-(4-Cl)Phe. In yet another embodiment, $X^6$ is L-Bip, D-Bip, L-(4-$CF_3$)Phe, D-(4-$CF_3$)Phe, L-(3,4-diCl)Phe, L-(3-F)Phe, D-(3-F)Phe, L-(4-Cl)Phe, or D-(4-Cl)Phe.

In another embodiment, $X^6$ is L-Bip, D-Bip, L-(4-$CF_3$)Phe, D-(4-$CF_3$)Phe, L-(3,4-diCl)Phe, D-(3,4-diCl)Phe, D-(3-F)Phe, L-(4-Cl)Phe, or D-(4-Cl)Phe. In another embodiment, $X^6$ is L-Bip, D-Bip, L-(4-$CF_3$)Phe, D-(4-$CF_3$)Phe, L-(3,4-diCl)Phe, D-(3,4-diCl)Phe, L-(3-F)Phe, L-(4-Cl)Phe, or D-(4-Cl)Phe. In yet another embodiment, $X^6$ is L-Bip, D-Bip, L-(4-$CF_3$)Phe, D-(4-$CF_3$)Phe, L-(3,4-diCl)Phe, D-(3,4-diCl)Phe, L-(3-F)Phe, D-(3-F)Phe, or D-(4-Cl)Phe. In another embodiment, $X^6$ is L-Bip, D-Bip, L-(4-$CF_3$)Phe, D-(4-$CF_3$)Phe, L-(3,4-diCl)Phe, D-(3,4-diCl)Phe, L-(3-F)Phe, D-(3-F)Phe, or L-(4-Cl)Phe. In yet another embodiment, $X^6$ is D-Bip, D-(4-$CF_3$)Phe, D-(3,4-diCl)Phe, D-(3-F)Phe, or D-(4-Cl)Phe. In another embodiment, $X^6$ is L-Bip, L-(4-$CF_3$)Phe, L-(3,4-diCl)Phe, L-(3-F)Phe, or L-(4-Cl)Phe.

In some embodiments of the Formulae above, $X^7$ is D-(N-Me)Ala, L-(N-Me)Phe, or D-(N-Me)Phe. In another embodiment, $X^7$ is L-(N-Me)Ala, L-(N-Me)Phe, or D-(N-Me)Phe. In yet another embodiment, $X^7$ is L-(N-Me)Ala, D-(N-Me)Ala, or D-(N-Me)Phe. In another embodiment, $X^7$ is L-(N-Me)Ala, D-(N-Me)Ala, or L-(N-Me)Phe. In yet another embodiment, $X^7$ is D-(N-Me)Ala or D-(N-Me)Phe. In another embodiment, $X^7$ is L-(N-Me)Ala or L-(N-Me)Phe.

In some embodiments of the Formulae above, $X^8$ is D-Bip, L-Ser, D-Ser, L-Tyr, D-Tyr, L-(4-CF$_3$)Phe, D-(4-CF$_3$)Phe, L-Ala, D-Ala, L-Phe, D-Phe, L-Val, or D-Val. In another embodiment, $X^8$ is L-Bip, L-Ser, D-Ser, L-Tyr, D-Tyr, L-(4-CF$_3$)Phe, D-(4-CF$_3$)Phe, L-Ala, D-Ala, L-Phe, D-Phe, L-Val, or D-Val. In yet another embodiment, $X^8$ is L-Bip, D-Bip, D-Ser, L-Tyr, D-Tyr, L-(4-CF$_3$)Phe, D-(4-CF$_3$)Phe, L-Ala, D-Ala, L-Phe, D-Phe, L-Val, or D-Val. In another embodiment, $X^8$ is L-Bip, D-Bip, L-Ser, L-Tyr, D-Tyr, L-(4-CF$_3$)Phe, D-(4-CF$_3$)Phe, L-Ala, D-Ala, L-Phe, D-Phe, L-Val, or D-Val. In yet another embodiment, $X^8$ is L-Bip, D-Bip, L-Ser, D-Ser, D-Tyr, L-(4-CF$_3$)Phe, D-(4-CF$_3$)Phe, L-Ala, D-Ala, L-Phe, D-Phe, L-Val, or D-Val. In another embodiment, $X^8$ is L-Bip, D-Bip, L-Ser, D-Ser, L-Tyr, L-(4-CF$_3$)Phe, D-(4-CF$_3$)Phe, L-Ala, D-Ala, L-Phe, D-Phe, L-Val, or D-Val. In yet another embodiment, $X^8$ is L-Bip, D-Bip, L-Ser, D-Ser, L-Tyr, D-Tyr, D-(4-CF$_3$)Phe, L-Ala, D-Ala, L-Phe, D-Phe, L-Val, or D-Val. In another embodiment, $X^8$ is L-Bip, D-Bip, L-Ser, D-Ser, L-Tyr, D-Tyr, L-(4-CF$_3$)Phe, L-Ala, D-Ala, L-Phe, D-Phe, L-Val, or D-Val. In yet another embodiment, $X^8$ is L-Bip, D-Bip, L-Ser, D-Ser, L-Tyr, D-Tyr, L-(4-CF$_3$)Phe, D-(4-CF$_3$)Phe, D-Ala, L-Phe, D-Phe, L-Val, or D-Val.

In another embodiment, $X^8$ is L-Bip, D-Bip, L-Ser, D-Ser, L-Tyr, D-Tyr, L-(4-CF$_3$)Phe, D-(4-CF$_3$)Phe, L-Ala, L-Phe, D-Phe, L-Val, or D-Val. In another embodiment, $X^8$ is L-Bip, D-Bip, L-Ser, D-Ser, L-Tyr, D-Tyr, L-(4-CF$_3$)Phe, D-(4-CF$_3$)Phe, L-Ala, D-Ala, D-Phe, L-Val, or D-Val. In yet another embodiment, $X^8$ is L-Bip, D-Bip, L-Ser, D-Ser, L-Tyr, D-Tyr, L-(4-CF$_3$)Phe, D-(4-CF$_3$)Phe, L-Ala, D-Ala, L-Phe, L-Val, or D-Val. In another embodiment, $X^8$ is L-Bip, D-Bip, L-Ser, D-Ser, L-Tyr, D-Tyr, L-(4-CF$_3$)Phe, D-(4-CF$_3$)Phe, L-Ala, D-Ala, L-Phe, D-Phe, or D-Val. In yet another embodiment, $X^8$ is L-Bip, D-Bip, L-Ser, D-Ser, L-Tyr, D-Tyr, L-(4-CF$_3$)Phe, D-(4-CF$_3$)Phe, L-Ala, D-Ala, L-Phe, D-Phe, or L-Val. In another embodiment, $X^8$ is D-Bip, D-Ser, D-Tyr, D-(4-CF$_3$)Phe, D-Ala, D-Phe, or D-Val. In yet another embodiment, $X^8$ is L-Bip, L-Ser, L-Tyr, L-(4-CF$_3$)Phe, L-Ala, L-Phe, or L-Val.

In some embodiments of the Formulae above, $X^9$ is D-Thr. In another embodiment, $X^9$ is L-Thr.

In some embodiments of the Formulae above, $X^{10}$ is D-Thr, L-Ser, or D-Ser. In another embodiment, $X^{10}$ is L-Thr, L-Ser, or D-Ser. In yet another embodiment, $X^{10}$ is L-Thr, D-Thr, or D-Ser. In yet another embodiment, $X^{10}$ is L-Thr, D-Thr, or L-Ser. In another embodiment, $X^{10}$ is D-Thr or D-Ser. In yet another embodiment, $X^{10}$ is L-Thr or L-Ser.

In some embodiments of the Formulae above, $X^{11}$ is D-Ser, L-Asp, D-Asp, L-Asn, D-Asn, L-Pro, D-Pro, L-Ala, D-Ala, L-Hse, or D-Hse. In another embodiment, $X^{11}$ is L-Ser, L-Asp, D-Asp, L-Asn, D-Asn, L-Pro, D-Pro, L-Ala, D-Ala, L-Hse, or D-Hse. In another embodiment, $X^{11}$ is L-Ser, D-Ser, D-Asp, L-Asn, D-Asn, L-Pro, D-Pro, L-Ala, D-Ala, L-Hse, or D-Hse. In another embodiment, $X^{11}$ is L-Ser, D-Ser, L-Asp, L-Asn, D-Asn, L-Pro, D-Pro, L-Ala, D-Ala, L-Hse, or D-Hse. In yet another embodiment, $X^{11}$ is D-Ala, L-Hse, or D-Hse. In another embodiment, $X^{11}$ is L-Ser, D-Ser, L-Asp, D-Asp, L-Pro, D-Pro, L-Ala, D-Ala, L-Hse, or D-Hse. In yet another embodiment, $X^{11}$ is L-Ser, D-Ser, L-Asp, D-Asp, L-Asn, D-Pro, L-Ala, D-Ala, L-Hse, or D-Hse. In another embodiment, $X^{11}$ is L-Ser, D-Ser, L-Asp, D-Asp, L-Asn, D-Asn, L-Pro, L-Ala, D-Ala, L-Hse, or D-Hse.

In another embodiment, $X^{11}$ is L-Ser, D-Ser, L-Asp, D-Asp, L-Asn, D-Asn, L-Pro, D-Pro, D-Ala, L-Hse, or D-Hse. In yet another embodiment, $X^{11}$ is L-Ser, D-Ser, L-Asp, D-Asp, L-Asn, D-Asn, L-Pro, D-Pro, L-Ala, L-Hse, or D-Hse. In another embodiment, $X^{11}$ is L-Ser, D-Ser, L-Asp, D-Asp, L-Asn, D-Asn, L-Pro, D-Pro, L-Ala, D-Ala, or D-Hse. In yet another embodiment, $X^{11}$ is L-Ser, D-Ser, L-Asp, D-Asp, L-Asn, D-Asn, L-Pro, D-Pro, L-Ala, D-Ala, or L-Hse. In another embodiment, $X^{11}$ is D-Ser, D-Asp, D-Asn, D-Pro, D-Ala, or D-Hse. In yet another embodiment, $X^{11}$ is L-Ser, L-Asp, L-Asn, L-Pro, L-Ala, or L-Hse.

In some embodiments of the Formulae above, $X^{12}$ is L-Val, D-Val, L-Glu, or D-Glu. In another embodiment, $X^{12}$ is L-Val, D-Val, L-Glu, or D-Glu. In yet another embodiment, $X^{12}$ is D-Val, L-Glu, or D-Glu. In another embodiment, $X^{12}$ is L-Val, L-Glu, or D-Glu. In yet another embodiment, $X^{12}$ is L-Val, D-Val, or D-Glu. In another embodiment, $X^{12}$ is L-Val, D-Val, or L-Glu. In another embodiment, $X^{12}$ is L-Val or D-Glu. In another embodiment, $X^{12}$ is D-Val or D-Glu. In yet another embodiment, $X^{12}$ is D-Val or D-Glu. In another embodiment, $X^{12}$ is L-Val or L-Glu. In some embodiments of the Formulae above, $X^{13}$ is D-Phe. In another embodiment, $X^{13}$ is L-Phe.

In some embodiments of the Formulae above, $X^{13}$ is L-Phe and $X^2$ is L-Pro. In another embodiment, $X^{13}$ is L-Phe and $X^9$ is L-Thr. In another embodiment, $X^{13}$ is L-Phe and $X^{12}$ is L-Val or L-Glu. In yet another embodiment, $X^{13}$ is L-Phe and $X^{12}$ is L-Val. In another embodiment, $X^{13}$ is L-Phe and $X^1$ is absent or Gly. In yet another embodiment, $X^{13}$ is L-Phe and $X^{10}$ is L-Thr or L-Ser. In another embodiment, $X^{13}$ is L-Phe and $R^1$ is H or $(C_1-C_3)$alkyl. In yet another embodiment, $X^{13}$ is L-Phe and $R^1$ is H.

In some embodiments of the Formulae above, $X^2$ is L-Pro and $X^9$ is L-Thr. In another embodiment, $X^2$ is L-Pro and $X^{12}$ is L-Val or L-Glu. In yet another embodiment, $X^2$ is L-Pro and $X^{12}$ is L-Val. In yet another embodiment, $X^2$ is L-Pro and $X^1$ is absent or Gly. In another embodiment, $X^2$ is L-Pro and $X^{10}$ is L-Thr or L-Ser. In yet another embodiment, $X^2$ is L-Pro and $R^1$ is H or $(C_1-C_3)$alkyl. In another embodiment, $X^2$ is L-Pro and $R^1$ is H.

In some embodiments of the Formulae above, $X^9$ is L-Thr and $X^{12}$ is L-Val or L-Glu. In another embodiment, $X^9$ is L-Thr and $X^{12}$ is L-Val. In yet another embodiment, $X^9$ is L-Thr and $X^1$ is absent or Gly. In another embodiment, $X^9$ is L-Thr and $X^{10}$ is L-Thr or L-Ser. In yet another embodiment, $X^9$ is L-Thr and $R^1$ is H or $(C_1-C_3)$alkyl. In another embodiment, $X^9$ is L-Thr and $R^1$ is H.

In some embodiments of the Formulae above, $X^{12}$ is L-Val or L-Glu and $X^1$ is absent or Gly. In another embodiment, $X^{12}$ is L-Val or L-Glu and $X^{10}$ is L-Thr or L-Ser. In yet another embodiment, $X^{12}$ is L-Val or L-Glu and $R^1$ is H or $(C_1-C_3)$alkyl. In another embodiment, $X^{12}$ is L-Val or L-Glu and $R^1$ is H. In yet another embodiment, $X^{12}$ is L-Val and $X^1$ is absent or Gly. In another embodiment, $X^{12}$ is L-Val and $X^{10}$ is L-Thr or L-Ser. In yet another embodiment, $X^{12}$ is L-Val and $R^1$ is H or $(C_1-C_3)$alkyl. In another embodiment, $X^{12}$ is L-Val and $R^1$ is H.

In some embodiments of the Formulae above, $X^1$ is absent or Gly and $X^{10}$ is L-Thr or L-Ser. In another embodiment, $X^1$ is absent or Gly and $R^1$ is H or $(C_1-C_3)$alkyl. In yet another embodiment, $X^1$ is absent or Gly and $R^1$ is H. In another embodiment, $X^{10}$ is L-Thr or L-Ser and $R^1$ is H or $(C_1-C_3)$ alkyl. In yet another embodiment, $X^{10}$ is L-Thr or L-Ser and $R^1$ is H.

In some embodiments of the Formulae above, $X^{13}$ is L-Phe, $X^2$ is L-Pro, and $X^9$ is L-Thr. In yet another embodiment, $X^{13}$ is L-Phe, $X^2$ is L-Pro, and $X^{12}$ is L-Val or L-Glu. In another embodiment, $X^{13}$ is L-Phe, $X^2$ is L-Pro, and $X^{12}$ is L-Val. In another embodiment, $X^{13}$ is L-Phe, $X^2$ is L-Pro, and $X^1$ is absent or Gly. In another embodiment, $X^{13}$ is L-Phe, $X^2$ is L-Pro, and $X^{10}$ is L-Thr or L-Ser. In another embodiment, $X^{13}$ is L-Phe, $X^2$ is L-Pro, and $R^1$ is H or $(C_1-C_3)$alkyl. In another embodiment, $X^{13}$ is L-Phe, $X^2$ is L-Pro, and $R^1$ is H.

In some embodiments of the Formulae above, $X^{13}$ is L-Phe, $X^9$ is L-Thr, and $X^{12}$ is L-Val or L-Glu. In another embodiment, $X^{13}$ is L-Phe, $X^9$ is L-Thr, and $X^{12}$ is L-Val. In yet another embodiment, $X^{13}$ is L-Phe, $X^9$ is L-Thr, and $X^1$ is absent or Gly. In another embodiment, $X^{13}$ is L-Phe, $X^9$ is L-Thr, and $X^{10}$ is L-Thr or L-Ser. In yet another embodiment, $X^{13}$ is L-Phe, $X^9$ is L-Thr, and $R^1$ is H or $(C_1-C_3)$alkyl. In another embodiment, $X^{13}$ is L-Phe, $X^9$ is L-Thr, and $R^1$ is H.

In some embodiments of the Formulae above, $X^9$ is L-Thr, $X^{12}$ is L-Val or L-Glu, and $X^1$ is absent or Gly. In another embodiment, $X^9$ is L-Thr, $X^{12}$ is L-Val or L-Glu, and $X^{10}$ is L-Thr or L-Ser. In yet another embodiment, $X^9$ is L-Thr, $X^{12}$ is L-Val or L-Glu, and $R^1$ is H or $(C_1-C_3)$alkyl. In another embodiment, $X^9$ is L-Thr, $X^{12}$ is L-Val or L-Glu, and $R^1$ is H.

In some embodiments of the Formulae above, $X^9$ is L-Thr, $X^{12}$ is L-Val, and $X^1$ is absent or Gly. In another embodiment, $X^9$ is L-Thr, $X^{12}$ is L-Val, and $X^{10}$ is L-Thr or L-Ser. In yet another embodiment, $X^9$ is L-Thr, $X^{12}$ is L-Val, and $R^1$ is H or $(C_1-C_3)$alkyl. In another embodiment, $X^9$ is L-Thr, $X^{12}$ is L-Val, and $R^1$ is H. In yet another embodiment, $X^{12}$ is L-Val or L-Glu, $X^1$ is absent or Gly, and $X^{10}$ is L-Thr or L-Ser. In another embodiment, $X^{12}$ is L-Val or L-Glu, $X^1$ is absent or Gly, and $R^1$ is H or $(C_1-C_3)$alkyl. In yet another embodiment, $X^{12}$ is L-Val or L-Glu, $X^1$ is absent or Gly, and $R^1$ is H. In another embodiment, $X^1$ is absent or Gly, $X^{10}$ is L-Thr or L-Ser, and $R^1$ is H or $(C_1-C_3)$alkyl. In another embodiment, $X^1$ is absent or Gly, $X^{10}$ is L-Thr or L-Ser, and $R^1$ is H.

In some embodiments of the Formulae above, $X^{13}$ is L-Phe, $X^2$ is L-Pro, $X^9$ is L-Thr, and $X^{12}$ is L-Val or L-Glu. In another embodiment, $X^{13}$ is L-Phe, $X^2$ is L-Pro, $X^9$ is L-Thr, and $X^{12}$ is L-Val. In yet another embodiment, $X^{13}$ is L-Phe, $X^2$ is L-Pro, $X^9$ is L-Thr, and $X^1$ is absent or Gly. In another embodiment, $X^{13}$ is L-Phe, $X^2$ is L-Pro, $X^9$ is L-Thr, and $X^{10}$ is L-Thr or L-Ser. In yet another embodiment, $X^{13}$ is L-Phe, $X^2$ is L-Pro, $X^9$ is L-Thr, and $R^1$ is H or $(C_1-C_3)$alkyl. In another embodiment, $X^{13}$ is L-Phe, $X^2$ is L-Pro, $X^9$ is L-Thr, and $R^1$ is H. In yet another embodiment, $X^{13}$ is L-Phe, $X^2$ is L-Pro, $X^9$ is L-Thr, and $X^1$ is absent, Gly, Gly-L-Lys*, or Gly-D-Lys*, wherein * denotes the point of attachment to NHR$^1$.

In some embodiments of the Formulae above, $X^{13}$ is L-Phe, $X^2$ is L-Pro, $X^{12}$ is L-Val or L-Glu, and $X^1$ is absent or Gly. In another embodiment, $X^{13}$ is L-Phe, $X^2$ is L-Pro, $X^{12}$ is L-Val or L-Glu, and $X^{10}$ is L-Thr or L-Ser. In another embodiment, $X^{13}$ is L-Phe, $X^2$ is L-Pro, $X^{12}$ is L-Val or L-Glu, and $R^1$ is H or $(C_1-C_3)$alkyl. In another embodiment, $X^{13}$ is L-Phe, $X^2$ is L-Pro, $X^{12}$ is L-Val or L-Glu, and $R^1$ is H. In yet another embodiment, $X^{13}$ is L-Phe, $X^2$ is L-Pro, $X^{12}$ is L-Val, and $X^1$ is absent or Gly. In another embodiment, $X^{13}$ is L-Phe, $X^2$ is L-Pro, $X^{12}$ is L-Val, and $X^{10}$ is L-Thr or L-Ser. In yet another embodiment, $X^{13}$ is L-Phe, $X^2$ is L-Pro, $X^{12}$ is L-Val, and $R^1$ is H or $(C_1-C_3)$alkyl. In another embodiment, $X^{13}$ is L-Phe, $X^2$ is L-Pro, $X^{12}$ is L-Val, and $R^1$ is H. In yet another embodiment, $X^{13}$ is L-Phe, $X^2$ is L-Pro, $X^1$ is absent or Gly, and $X^{10}$ is L-Thr or L-Ser. In another embodiment, $X^{13}$ is L-Phe, $X^2$ is L-Pro, $X^1$ is absent or Gly, and $R^1$ is H or $(C_1-C_3)$alkyl. In yet another embodiment, $X^{13}$ is L-Phe, $X^2$ is L-Pro, $X^1$ is absent or Gly, and $R^1$ is H.

In some embodiments of the Formulae above, $X^{13}$ is L-Phe, $X^2$ is L-Pro, $X^{12}$ is L-Val or L-Glu, and $X^1$ is absent, Gly, Gly-L-Lys*, or Gly-D-Lys*, wherein * denotes the point of attachment to NHR$^1$. In another embodiment, $X^{13}$ is L-Phe, $X^2$ is L-Pro, $X^{12}$ is L-Val, and $X^1$ is absent, Gly, Gly-L-Lys*, or Gly-D-Lys*, wherein * denotes the point of attachment to NHR$^1$. In yet another embodiment, $X^{13}$ is L-Phe, $X^2$ is L-Pro, $X^1$ is absent, Gly, Gly-L-Lys*, or Gly-D-Lys*, wherein * denotes the point of attachment to NHR$^1$, and $X^{10}$ is L-Thr or L-Ser. In another embodiment, $X^{13}$ is L-Phe, $X^2$ is L-Pro, $X^1$ is absent, Gly, Gly-L-Lys*, or Gly-D-Lys*, wherein * denotes the point of attachment to NHR$^1$, and $R^1$ is H or $(C_1-C_3)$alkyl. In yet another embodiment, $X^{13}$ is L-Phe, $X^2$ is L-Pro, $X^1$ is absent, Gly, Gly-L-Lys*, or Gly-D-Lys*, wherein * denotes the point of attachment to NHR$^1$, and $R^1$ is H.

In some embodiments of the Formulae above, $X^{13}$ is L-Phe, $X^9$ is L-Thr, $X^{12}$ is L-Val or L-Glu, and $X^1$ is absent or Gly. In another embodiment, $X^{13}$ is L-Phe, $X^9$ is L-Thr, $X^{12}$ is L-Val or L-Glu, and $X^{10}$ is L-Thr or L-Ser. In yet another embodiment, $X^{13}$ is L-Phe, $X^9$ is L-Thr, $X^{12}$ is L-Val or L-Glu, and $R^1$ is H or $(C_1-C_3)$alkyl. In another embodiment, $X^{13}$ is L-Phe, $X^9$ is L-Thr, $X^{12}$ is L-Val or L-Glu, and $R^1$ is H. In yet another embodiment, $X^{13}$ is L-Phe, $X^9$ is L-Thr, $X^{12}$ is L-Val, and $X^1$ is absent or Gly. In another embodiment, $X^{13}$ is L-Phe, $X^9$ is L-Thr, $X^{12}$ is L-Val, and $X^{10}$ is L-Thr or L-Ser. In another embodiment, $X^{13}$ is L-Phe, $X^9$ is L-Thr, $X^{12}$ is L-Val, and $R^1$ is H or $(C_1-C_3)$alkyl. In another embodiment, $X^{13}$ is L-Phe, $X^9$ is L-Thr, $X^{12}$ is L-Val, and $R^1$ is H.

In some embodiments of the Formulae above, $X^{13}$ is L-Phe, $X^9$ is L-Thr, $X^{12}$ is L-Val or L-Glu, and $X^1$ is absent, Gly, Gly-L-Lys*, or Gly-D-Lys*, wherein * denotes the point of attachment to NHR$^1$. In yet another embodiment, $X^{13}$ is L-Phe, $X^9$ is L-Thr, $X^{12}$ is L-Val, and $X^1$ is absent, Gly, Gly-L-Lys*, or Gly-D-Lys*, wherein * denotes the point of attachment to NHR$^1$.

In some embodiments of the Formulae above, $X^{13}$ is L-Phe, $X^{12}$ is L-Val or L-Glu, $X^1$ is absent or Gly, and $X^{10}$ is L-Thr or L-Ser. In another embodiment, $X^{13}$ is L-Phe, $X^{12}$ is L-Val or L-Glu, $X^1$ is absent or Gly, and $R^1$ is H or $(C_1-C_3)$alkyl. In another embodiment, $X^{13}$ is L-Phe, $X^{12}$ is L-Val or L-Glu, $X^1$ is absent or Gly, and $R^1$ is H. In another embodiment, $X^{13}$ is L-Phe, $X^{12}$ is L-Val, $X^1$ is absent or Gly, and $X^{10}$ is L-Thr or L-Ser. In yet another embodiment, $X^{13}$ is L-Phe, $X^{12}$ is L-Val, $X^1$ is absent or Gly, and $R^1$ is H or $(C_1-C_3)$alkyl. In another embodiment, $X^{13}$ is L-Phe, $X^{12}$ is L-Val, $X^1$ is absent or Gly, and $R^1$ is H.

In some embodiments of the Formulae above, $X^{13}$ is L-Phe, $X^1$ is absent or Gly, $X^{10}$ is L-Thr or L-Ser, and $R^1$ is H or $(C_1-C_3)$alkyl. In another embodiment, $X^{13}$ is L-Phe, $X^1$ is absent or Gly, $X^{10}$ is L-Thr or L-Ser, and $R^1$ is H.

In some embodiments of the Formulae above, $X^{13}$ is L-Phe, $X^{12}$ is L-Val or L-Glu, $X^1$ is absent, Gly, Gly-L-Lys*, or Gly-D-Lys*, wherein * denotes the point of attachment to NHR$^1$, and $X^{10}$ is L-Thr or L-Ser. In another embodiment, $X^{13}$ is L-Phe, $X^{12}$ is L-Val or L-Glu, $X^1$ is absent, Gly, Gly-L-Lys*, or Gly-D-Lys*, wherein * denotes the point of attachment to NHR$^1$, and R$^1$ is H or (C$_1$-C$_3$)alkyl. In yet another embodiment, X$^{13}$ is L-Phe, X$^{12}$ is L-Val or L-Glu, X$^1$ is absent, Gly, Gly-L-Lys*, or Gly-D-Lys*, wherein * denotes the point of attachment to NHR$^1$, and R$^1$ is H. In another embodiment, X$^{13}$ is L-Phe, X$^{12}$ is L-Val, X$^1$ is absent, Gly, Gly-L-Lys*, or Gly-D-Lys*, wherein * denotes the point of attachment to NHR$^1$, and X$^{10}$ is L-Thr or L-Ser. In yet another embodiment, X$^{13}$ is L-Phe, X$^{12}$ is L-Val, X$^1$ is absent, Gly, Gly-L-Lys*, or Gly-D-Lys*, wherein * denotes the point of attachment to NHR$^1$, and R$^1$ is H or (C$_1$-C$_3$)alkyl. In another embodiment, X$^{13}$ is L-Phe, X$^{12}$ is L-Val, X$^1$ is absent, Gly, Gly-L-Lys*, or Gly-D-Lys*, wherein * denotes the point of attachment to NHR$^1$, and R$^1$ is H.

In some embodiments of the Formulae above, X$^{13}$ is L-Phe, X$^1$ is absent, Gly, Gly-L-Lys*, or Gly-D-Lys*, wherein * denotes the point of attachment to NHR$^1$, X$^{10}$ is L-Thr or L-Ser, and R$^1$ is H or (C$_1$-C$_3$)alkyl. In another embodiment, X$^{13}$ is L-Phe, X$^1$ is absent, Gly, Gly-L-Lys*, or Gly-D-Lys*, wherein * denotes the point of attachment to NHR$^1$, X$^{10}$ is L-Thr or L-Ser, and R$^1$ is H.

In some embodiments of the Formulae above, X$^{13}$ is L-Phe, X$^2$ is L-Pro, X$^9$ is L-Thr, X$^{12}$ is L-Val or L-Glu, and X$^1$ is absent or Gly. In another embodiment, X$^{13}$ is L-Phe, X$^2$ is L-Pro, X$^9$ is L-Thr, X$^{12}$ is L-Val or L-Glu, and X$^{10}$ is L-Thr or L-Ser. In yet another embodiment, X$^{13}$ is L-Phe, X$^2$ is L-Pro, X$^9$ is L-Thr, X$^{12}$ is L-Val or L-Glu, and R$^1$ is H or (C$_1$-C$_3$)alkyl. In another embodiment, X$^{13}$ is L-Phe, X$^2$ is L-Pro, X$^9$ is L-Thr, X$^{12}$ is L-Val or L-Glu, and R$^1$ is H. In yet another embodiment, X$^{13}$ is L-Phe, X$^2$ is L-Pro, X$^9$ is L-Thr, X$^{12}$ is L-Val, and X$^1$ is absent or Gly.

In another embodiment, X$^{13}$ is L-Phe, X$^2$ is L-Pro, X$^9$ is L-Thr, X$^{12}$ is L-Val, and X$^{10}$ is L-Thr or L-Ser. In yet another embodiment, X$^{13}$ is L-Phe, X$^2$ is L-Pro, X$^9$ is L-Thr, X$^{12}$ is L-Val, and R$^1$ is H or (C$_1$-C$_3$)alkyl. In another embodiment, X$^{13}$ is L-Phe, X$^2$ is L-Pro, X$^9$ is L-Thr, X$^{12}$ is L-Val, and R$^1$ is H.

In some embodiments of the Formulae above, X$^{13}$ is L-Phe, X$^2$ is L-Pro, X$^9$ is L-Thr, X$^{12}$ is L-Val or L-Glu, and X$^1$ is absent, Gly, Gly-L-Lys*, or Gly-D-Lys*, wherein * denotes the point of attachment to NHR$^1$. In yet another embodiment, X$^{13}$ is L-Phe, X$^2$ is L-Pro, X$^9$ is L-Thr, X$^{12}$ is L-Val, and X$^1$ is absent, Gly, Gly-L-Lys*, or Gly-D-Lys*, wherein * denotes the point of attachment to NHR$^1$.

In some embodiments of the Formulae above, X$^{13}$ is L-Phe, X$^2$ is L-Pro, X$^9$ is L-Thr, X$^{12}$ is L-Val or L-Glu, X$^1$ is absent or Gly, and X$^{10}$ is L-Thr or L-Ser. In another embodiment, X$^{13}$ is L-Phe, X$^2$ is L-Pro, X$^9$ is L-Thr, X$^{12}$ is L-Val or L-Glu, X$^1$ is absent or Gly, and R$^1$ is H or (C$_1$-C$_3$)alkyl. In yet another embodiment, X$^{13}$ is L-Phe, X$^2$ is L-Pro, X$^9$ is L-Thr, X$^{12}$ is L-Val or L-Glu, X$^1$ is absent or Gly, and R$^1$ is H. In another embodiment, X$^{13}$ is L-Phe, X$^9$ is L-Thr, X$^{12}$ is L-Val or L-Glu, X$^1$ is absent or Gly, X$^{10}$ is L-Thr or L-Ser and R$^1$ is H or (C$_1$-C$_3$)alkyl. In yet another embodiment, X$^{13}$ is L-Phe, X$^9$ is L-Thr, X$^{12}$ is L-Val or L-Glu, X$^1$ is absent or Gly, X$^{10}$ is L-Thr or L-Ser and R$^1$ is H. In another embodiment, X$^{13}$ is L-Phe, X$^2$ is L-Pro, X$^9$ is L-Thr, X$^{12}$ is L-Val, X$^1$ is absent or Gly, and X$^{10}$ is L-Thr or L-Ser. In yet another embodiment, X$^{13}$ is L-Phe, X$^2$ is L-Pro, X$^9$ is L-Thr, X$^{12}$ is L-Val, X$^1$ is absent or Gly, and R$^1$ is H or (C$_1$-C$_3$)alkyl. In another embodiment, X$^{13}$ is L-Phe, X$^2$ is L-Pro, X$^9$ is L-Thr, X$^{12}$ is L-Val, X$^1$ is absent or Gly, and R$^1$ is H. In yet another embodiment, X$^{13}$ is L-Phe, X$^9$ is L-Thr, X$^{12}$ is L-Val, X$^1$ is absent or Gly, X$^{10}$ is L-Thr or L-Ser and R$^1$ is H or (C$_1$-C$_3$)alkyl. In another embodiment, X$^{13}$ is L-Phe, X$^9$ is L-Thr, X$^{12}$ is L-Val or L-Glu, X$^1$ is absent or Gly, X$^{10}$ is L-Thr or L-Ser and R$^1$ is H.

In some embodiments of the Formulae above, X$^{13}$ is L-Phe, X$^2$ is L-Pro, X$^9$ is L-Thr, X$^{12}$ is L-Val or L-Glu, X$^1$ is absent, Gly, Gly-L-Lys*, or Gly-D-Lys*, wherein * denotes the point of attachment to NHR$^1$, and X$^{10}$ is L-Thr or L-Ser. In another embodiment, X$^{13}$ is L-Phe, X$^2$ is L-Pro, X$^9$ is L-Thr, X$^{12}$ is L-Val or L-Glu, X$^1$ is absent, Gly, Gly-L-Lys*, or Gly-D-Lys*, wherein * denotes the point of attachment to NHR$^1$, and R$^1$ is H or (C$_1$-C$_3$)alkyl. In yet another embodiment, X$^{13}$ is L-Phe, X$^2$ is L-Pro, X$^9$ is L-Thr, X$^{12}$ is L-Val or L-Glu, X$^1$ is absent, Gly, Gly-L-Lys*, or Gly-D-Lys*, wherein * denotes the point of attachment to NHR$^1$, and R$^1$ is H. In another embodiment, X$^{13}$ is L-Phe, X$^9$ is L-Thr, X$^{12}$ is L-Val or L-Glu, X$^1$ is absent, Gly, Gly-L-Lys*, or Gly-D-Lys*, wherein * denotes the point of attachment to NHR$^1$, X$^{10}$ is L-Thr or L-Ser and R$^1$ is H or (C$_1$-C$_3$)alkyl. In yet another embodiment, X$^{13}$ is L-Phe, X$^9$ is L-Thr, X$^{12}$ is L-Val or L-Glu, X$^1$ is absent, Gly, Gly-L-Lys*, or Gly-D-Lys*, wherein * denotes the point of attachment to NHR$^1$, X$^{10}$ is L-Thr or L-Ser and R$^1$ is H. In another embodiment, X$^{13}$ is L-Phe, X$^2$ is L-Pro, X$^9$ is L-Thr, X$^{12}$ is L-Val, X$^1$ is absent, Gly, Gly-L-Lys*, or Gly-D-Lys*, wherein * denotes the point of attachment to NHR$^1$, and X$^{10}$ is L-Thr or L-Ser. In yet another embodiment, X$^{13}$ is L-Phe, X$^2$ is L-Pro, X$^9$ is L-Thr, X$^{12}$ is L-Val, X$^1$ is absent, Gly, Gly-L-Lys*, or Gly-D-Lys*, wherein * denotes the point of attachment to NHR$^1$, and R$^1$ is H or (C$_1$-C$_3$)alkyl. In another embodiment, X$^{13}$ is L-Phe, X$^2$ is L-Pro, X$^9$ is L-Thr, X$^{12}$ is L-Val, X$^1$ is absent, Gly, Gly-L-Lys*, or Gly-D-Lys*, wherein * denotes the point of attachment to NHR$^1$, and R$^1$ is H. In yet another embodiment, X$^{13}$ is L-Phe, X$^9$ is L-Thr, X$^{12}$ is L-Val, X$^1$ is absent, Gly, Gly-L-Lys*, or Gly-D-Lys*, wherein * denotes the point of attachment to NHR$^1$, X$^{10}$ is L-Thr or L-Ser and R$^1$ is H or (C$_1$-C$_3$)alkyl. In another embodiment, X$^{13}$ is L-Phe, X$^9$ is L-Thr, X$^{12}$ is L-Val, X$^1$ is absent, Gly, Gly-L-Lys*, or Gly-D-Lys*, wherein * denotes the point of attachment to NHR$^1$, X$^{10}$ is L-Thr or L-Ser and R$^1$ is H.

In some embodiments of the Formulae above, X$^{13}$ is L-Phe, X$^9$ is L-Thr, X$^{12}$ is L-Val or L-Glu, X$^1$ is absent or Gly, X$^{10}$ is L-Thr or L-Ser and R$^1$ is H or (C$_1$-C$_3$)alkyl. In another embodiment, X$^{13}$ is L-Phe, X$^9$ is L-Thr, X$^{12}$ is L-Val or L-Glu, X$^1$ is absent or Gly, X$^{10}$ is L-Thr or L-Ser and R$^1$ is H. In yet another embodiment, X$^{13}$ is L-Phe, X$^9$ is L-Thr, X$^{12}$ is L-Val, X$^1$ is absent or Gly, X$^{10}$ is L-Thr or L-Ser and R$^1$ is H or (C$_1$-C$_3$)alkyl. In another embodiment, X$^{13}$ is L-Phe, X$^9$ is L-Thr, X$^{12}$ is L-Val, X$^1$ is absent or Gly, X$^{10}$ is L-Thr or L-Ser and R$^1$ is H.

In some embodiments of the Formulae above, X$^{13}$ is L-Phe, X$^2$ is L-Pro, X$^9$ is L-Thr, X$^{12}$ is L-Val or L-Glu, X$^1$ is absent or Gly, X$^{10}$ is L-Thr or L-Ser and R$^1$ is H or (C$_1$-C$_3$)alkyl. In another embodiment, X$^{13}$ is L-Phe, X$^2$ is L-Pro, X$^9$ is L-Thr, X$^{12}$ is L-Val or L-Glu, X$^1$ is absent or Gly, $X^{10}$ is L-Thr or L-Ser and $R^1$ is H. In yet another embodiment, $X^{13}$ is L-Phe, $X^2$ is L-Pro, $X^9$ is L-Thr, $X^{12}$ is L-Val, $X^1$ is absent or Gly, $X^{10}$ is L-Thr or L-Ser and $R^1$ is H or $(C_1-C_3)$alkyl. In another embodiment, $X^{13}$ is L-Phe, $X^2$ is L-Pro, $X^9$ is L-Thr, $X^{12}$ is L-Val, $X^1$ is absent or Gly, $X^{10}$ is L-Thr or L-Ser and $R^1$ is H.

In some embodiments of the Formulae above, $X^{13}$ is L-Phe, $X^2$ is L-Pro, $X^9$ is L-Thr, $X^{12}$ is L-Val or L-Glu, $X^1$ is absent, Gly, Gly-L-Lys*, or Gly-D-Lys*, wherein * denotes the point of attachment to $NHR^1$, $X^{10}$ is L-Thr or L-Ser and $R^1$ is H or $(C_1-C_3)$alkyl. In another embodiment, $X^{13}$ is L-Phe, $X^2$ is L-Pro, $X^9$ is L-Thr, $X^{12}$ is L-Val or L-Glu, $X^1$ is absent, Gly, Gly-L-Lys*, or Gly-D-Lys*, wherein * denotes the point of attachment to $NHR^1$, $X^{10}$ is L-Thr or L-Ser and $R^1$ is H. In yet another embodiment, $X^{13}$ is L-Phe, $X^2$ is L-Pro, $X^9$ is L-Thr, $X^{12}$ is L-Val, $X^1$ is absent, Gly, Gly-L-Lys*, or Gly-D-Lys*, wherein * denotes the point of attachment to $NHR^1$, $X^{10}$ is L-Thr or L-Ser and $R^1$ is H or $(C_1-C_3)$alkyl. In another embodiment, $X^{13}$ is L-Phe, $X^2$ is L-Pro, $X^9$ is L-Thr, $X^{12}$ is L-Val, $X^1$ is absent, Gly, Gly-L-Lys*, or Gly-D-Lys*, wherein * denotes the point of attachment to $NHR^1$, $X^{10}$ is L-Thr or L-Ser and $R^1$ is H.

In some embodiments of the Formulae above, $R^1$ is H or $(C_1-C_4)$alkyl, $X^1$ is absent or Gly, $X^2$ is L-Pro, and $X^3$ is L-Arg, L-Ser, L-His, or L-Ala. In another embodiment, $R^1$ is H or $(C_1-C_4)$alkyl, $X^1$ is absent or Gly, $X^2$ is L-Pro, $X^3$ is L-Arg, L-Ser, L-His, or L-Ala, and $X^4$ is L-Asp, L-Asn, L-Glu, L-Lys, L-Gln, L-Pro, L-Ala, or L-(N-Me)Glu. In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, and $X^5$ is L-(N-Me)Ala or L-(N-Me)Glu. In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^6$ is L-Bip, L-(4-$CF_3$)Phe, L-(3,4-diCl)Phe, L-(3-F)Phe, or L-(4-Cl)Phe.

In some embodiments of the Formulae above, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, and $X^3$ is L-Arg, L-Ser, L-His, or L-Ala. In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, and $X^4$ is L-Asp, L-Asn, L-Glu, L-Lys, L-Gln, L-Pro, L-Ala, or L-(N-Me)Glu. In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, and $X^5$ is L-(N-Me)Ala or L-(N-Me)Glu. In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^6$ is L-Bip, L-(4-$CF_3$)Phe, L-(3,4-diCl)Phe, or L-(4-Cl)Phe.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, and $X^7$ is L-(N-Me)Ala or L-(N-Me)Phe.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-$CF_3$)Phe, L-Ala, L-Phe, or L-Val.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, and $X^9$ is L-Thr.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, and $X^{10}$ is L-Thr or L-Ser.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent or Gly, and $X^3$ is L-Arg, L-Ser, L-His, or L-Ala. In another embodiment, $R^1$ is H or $(C_1-C_4)$alkyl, $X^1$ is absent or Gly, $X^3$ is L-Arg, L-Ser, L-His, or L-Ala, and $X^4$ is L-Asp, L-Asn, L-Glu, L-Lys, L-Gln, L-Pro, L-Ala, or L-(N-Me)Glu. In yet another embodiment, $R^1$ is H or $(C_1-C_4)$alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, and $X^5$ is L-(N-Me)Ala or L-(N-Me)Glu. In another embodiment, $R^1$ is H or $(C_1-C_4)$alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^6$ is L-Bip, L-(4-CF$_3$)Phe, L-(3,4-diCl)Phe, L-(3-F)Phe, or L-(4-Cl)Phe.

In another embodiment, $R^1$ is H or (C$_1$-C$_4$)alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, and $X^7$ is L-(N-Me)Ala or L-(N-Me)Phe. In yet another embodiment, $R^1$ is H or (C$_1$-C$_4$)alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-CF$_3$)Phe, L-Ala, L-Phe, or L-Val.

In another embodiment, $R^1$ is H or (C$_1$-C$_4$)alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, and $X^9$ is L-Thr. In yet another embodiment, $R^1$ is H or (C$_1$-C$_4$)alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, and $X^{10}$ is L-Thr or L-Ser.

In another embodiment, $R^1$ is H or (C$_1$-C$_4$)alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse. In yet another embodiment, $R^1$ is H or (C$_1$-C$_4$)alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or (C$_1$-C$_4$)alkyl, $X^1$ is absent or Gly, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or (C$_1$-C$_4$)alkyl, $X^1$ is absent or Gly, $X^2$ is L-Pro, and $X^4$ is L-Asp, L-Asn, L-Glu, L-Lys, L-Gln, L-Pro, L-Ala, or L-(N-Me)Glu. In another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, and $X^5$ is L-(N-Me)Ala or L-(N-Me)Glu. In another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^6$ is L-Bip, L-(4-CF$_3$)Phe, L-(3,4-diCl)Phe, L-(3-F)Phe, or L-(4-Cl)Phe.

In another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, and $X^7$ is L-(N-Me)Ala or L-(N-Me)Phe.

In another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-CF$_3$)Phe, L-Ala, L-Phe, or L-Val. In yet another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, and $X^9$ is L-Thr.

In another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, and $X^{10}$ is L-Thr or L-Ser. In yet another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or (C$_1$-C$_4$)alkyl, $X^1$ is absent or Gly, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Ala, or L-Hse, $X^{12}$ is L-Val or L-Glu, and $X^{13}$ is L-Phe.

In some embodiments of the Formulae above, $R^1$ is H or (C$_1$-C$_4$)alkyl, $X^1$ is absent or Gly, $X^2$ is L-Pro, $X^3$ is L-Arg, L-Ser, L-His, or L-Ala, and $X^5$ is L-(N-Me)Ala or L-(N-Me)Glu. In another embodiment, $R^1$ is H or (C$_1$-C$_4$)alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, and $X^6$ is L-Bip, L-(4-CF$_3$)Phe, L-(3,4-diCl)Phe, L-(3-F)Phe, or L-(4-Cl)Phe. In another embodiment, $R^1$ is H or (C$_1$-C$_4$)alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, and $X^7$ is L-(N-Me)Ala or L-(N-Me)Phe.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-CF$_3$)Phe, L-Ala, L-Phe, or L-Val. In yet another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, and $X^9$ is L-Thr.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, and $X^{10}$ is L-Thr or L-Ser. In yet another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, and $X^6$ is L-Bip, L-(4-CF$_3$)Phe, L-(3,4-diCl)Phe, L-(3-F)Phe, or L-(4-Cl)Phe. In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^6$ is L-Bip, L-(4-CF$_3$)Phe, L-(3,4-diCl)Phe, L-(3-F)Phe, or L-(4-Cl)Phe, and $X^7$ is L-(N-Me)Ala or L-(N-Me)Phe.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-CF$_3$)Phe, L-Ala, L-Phe, or L-Val. In yet another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, and $X^{10}$ is L-Thr or L-Ser.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^7$ is L-(N-Me)Ala or L-(N-Me)Phe. In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, and $X^8$ is L-Bip, L-Ser, L-Tyr, L-(4-CF$_3$)Phe, L-Ala, L-Phe, or L-Val.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, and $X^9$ is L-Thr. In yet another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, and $X^{10}$ is L-Thr or L-Ser.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse. In yet another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-

Me)Ala or L-(N-Me)Glu, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, and $X^8$ is L-Bip, L-Ser, L-Tyr, L-(4-CF$_3$)Phe, L-Ala, L-Phe, or L-Val. In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^8$ is L-Bip, L-Ser, L-Tyr, L-(4-CF$_3$)Phe, L-Ala, L-Phe, or L-Val, and $X^9$ is L-Thr.

In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^8$ is L-Bip, L-Ser, L-Tyr, L-(4-CF$_3$)Phe, L-Ala, L-Phe, or L-Val, $X^9$ is L-Thr, and $X^{10}$ is L-Thr or L-Ser. In yet another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, and $X^9$ is L-Thr. In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, and $X^{10}$ is L-Thr or L-Ser.

In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, $X^{10}$ is L-Thr or L-Ser, and $X^{11}$ is L-Ser, L-Asp, L-Asn, L-Pro, L-Ala, or L-Hse. In yet another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, and $X^{10}$ is L-Thr or L-Ser. In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or $(C_1$-$C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, and $X^{11}$ is L-Ser, L-Asp, L-Asn, L-Pro, L-Ala, or L-Hse. In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{12}$ is L-Val or L-Glu, and $X^{13}$ is L-Phe.

In some embodiments of the Formulae above, $R^1$ is H or $(C_1-C_4)$alkyl, $X^1$ is absent or Gly, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{13}$ is L-Phe.

In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, and $X^7$ is L-(N-Me)Ala or L-(N-Me)Phe.

In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-CF$_3$)Phe, L-Ala, L-Phe, or L-Val.

In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, and $X^9$ is L-Thr.

In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, and $X^{10}$ is L-Thr or L-Ser.

In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-CF$_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-CF$_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent, Gly, Gly-L-Lys*, or Gly-D-Lys*, wherein * denotes the point of attachment to NHR$^1$, and $X^3$ is L-Arg, L-Ser, L-His, or L-Ala. In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^3$ is L-Arg, L-Ser, L-His, or L-Ala, and $X^4$ is L-Asp, L-Asn, L-Glu, L-Lys, L-Gln, L-Pro, L-Ala, or L-(N-Me)Glu. In yet another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, and $X^5$ is L-(N-Me)Ala or L-(N-Me)Glu. In another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^6$ is L-Bip, L-(4-CF$_3$)Phe, L-(3,4-diCl)Phe, L-(3-F)Phe, or L-(4-Cl)Phe.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, and $X^7$ is L-(N-Me)Ala or L-(N-Me)Phe. In yet another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-$CF_3$)Phe, L-Ala, L-Phe, or L-Val.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, and $X^9$ is L-Thr. In yet another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, and $X^{10}$ is L-Thr or L-Ser.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse. In yet another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, and $X^4$ is L-Asp, L-Asn, L-Glu, L-Lys, L-Gln, L-Pro, L-Ala, or L-(N-Me)Glu. In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, and $X^5$ is L-(N-Me)Ala or L-(N-Me)Glu. In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^6$ is L-Bip, L-(4-$CF_3$)Phe, L-(3,4-diCl)Phe, L-(3-F)Phe, or L-(4-Cl)Phe.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, and $X^7$ is L-(N-Me)Ala or L-(N-Me)Phe.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, and $X^8$ is L-Bip, L-Ser, L-Tyr, L-(4-$CF_3$)Phe, L-Ala, L-Phe, or L-Val. In yet another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, and $X^9$ is L-Thr.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, and $X^{10}$ is L-Thr or L-Ser.

In yet another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or $(C_1-C_4)$alkyl, $X^1$ is absent, Gly, Gly-L-Lys*, or Gly-D-Lys*, wherein * denotes the point of attachment to NHR$^1$, X$^2$ is L-Pro, X$^4$ is L-Asp, L-Asn, L-Glu, L-Lys, L-Gln, L-Pro, L-Ala, or L-(N-Me)Glu, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, X$^{10}$ is L-Thr or L-Ser, X$^{11}$ is L-Ser, L-Asp, L-Asn, L-Pro, L-Ala, or L-Hse, X$^{12}$ is L-Val or L-Glu, and X$^{13}$ is L-Phe.

In some embodiments of the Formulae above, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, and X$^5$ is L-(N-Me)Ala or L-(N-Me)Glu. In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, and X$^6$ is L-Bip, L-(4-CF$_3$)Phe, L-(3,4-diCl)Phe, L-(3-F)Phe, or L-(4-Cl)Phe. In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, and X$^7$ is L-(N-Me)Ala or L-(N-Me)Phe.

In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, and X$^8$ is L-Bip, L-Ser, L-Tyr, L-(4-CF$_3$)Phe, L-Ala, L-Phe, or L-Val. In yet another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, and X$^9$ is L-Thr.

In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, and X$^{10}$ is L-Thr or L-Ser. In yet another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, X$^{10}$ is L-Thr or L-Ser, and X$^{11}$ is L-Ser, L-Asp, L-Asn, L-Pro, L-Ala, or L-Hse.

In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, X$^{10}$ is L-Thr or L-Ser, X$^{11}$ is L-Ser, L-Asp, L-Asn, L-Pro, L-Ala, or L-Hse, and X$^{12}$ is L-Val or L-Glu. In yet another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^5$ is L-(N-Me)Ala or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, X$^{10}$ is L-Thr or L-Ser, X$^{11}$ is L-Ser, L-Asp, L-Asn, L-Pro, L-Ala, or L-Hse, L-Val, L-Glu, and X$^{13}$ is L-Phe.

In some embodiments of the Formulae above, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^4$ is L-Asp, L-Asn, L-Glu, L-Lys, L-Gln, L-Pro, L-Ala, or L-(N-Me)Glu, and X$^6$ is L-Bip, L-(4-CF$_3$)Phe, L-(3,4-diCl)Phe, L-(3-F)Phe, or L-(4-Cl)Phe. In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^4$ is L-Asp, L-Asn, L-Glu, L-Lys, L-Gln, L-Pro, L-Ala, or L-(N-Me)Glu, X$^6$ is L-Bip, L-(4-CF$_3$)Phe, L-(3,4-diCl)Phe, L-(3-F)Phe, or L-(4-Cl)Phe, and X$^7$ is L-(N-Me)Ala or L-(N-Me)Phe.

In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^4$ is L-Asp, L-Asn, L-Glu, L-Lys, L-Gln, L-Pro, L-Ala, or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, and X$^8$ is L-Bip, L-Ser, L-Tyr, L-(4-CF$_3$)Phe, L-Ala, L-Phe, or L-Val. In yet another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^4$ is L-Asp, L-Asn, L-Glu, L-Lys, L-Gln, L-Pro, L-Ala, or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, and X$^9$ is L-Thr.

In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^4$ is L-Asp, L-Asn, L-Glu, L-Lys, L-Gln, L-Pro, L-Ala, or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, and X$^{10}$ is L-Thr or L-Ser. In yet another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^4$ is L-Asp, L-Asn, L-Glu, L-Lys, L-Gln, L-Pro, L-Ala, or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, X$^{10}$ is L-Thr or L-Ser, and X$^{11}$ is L-Ser, L-Asp, L-Asn, L-Pro, L-Ala, or L-Hse.

In another embodiment, R$^1$ is H or (C$_1$-C$_4$)alkyl, X$^1$ is absent, Gly, Gly-L-Lys*, or Gly-D-Lys*, wherein * denotes the point of attachment to NHR$^1$, X$^2$ is L-Pro, X$^3$ is L-Arg, L-Ser, L-His, or L-Ala, X$^4$ is L-Asp, L-Asn, L-Glu, L-Lys, L-Gln, L-Pro, L-Ala, or L-(N-Me)Glu, X$^6$ is L-Bip, L-(4-CF$_3$)Phe, L-(3,4-diCl)Phe, L-(3-F)Phe, or L-(4-Cl)Phe, X$^7$ is L-(N-Me)Ala or L-(N-Me)Phe, X$^8$ is L-Bip, L-Ser, L-Tyr, L-(4-CF$_3$)Phe, L-Ala, L-Phe, or L-Val, X$^9$ is L-Thr, X$^{10}$ is L-Thr or L-Ser, X$^{11}$ is L-Ser, L-Asp, L-Asn, L-Pro, L-Ala, or L-Hse, and X$^{12}$ is L-Val or L-Glu. In yet another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, and $X^7$ is L-(N-Me)Ala or L-(N-Me)Phe. In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, and $X^8$ is L-Bip, L-Ser, L-Tyr, L-(4-$CF_3$)Phe, L-Ala, L-Phe, or L-Val.

In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, and $X^9$ is L-Thr. In yet another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, and $X^{10}$ is L-Thr or L-Ser.

In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse. In yet another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, and $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, and $X^8$ is L-Bip, L-Ser, L-Tyr, L-(4-$CF_3$)Phe, L-Ala, L-Phe, or L-Val. In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^8$ is L-Bip, L-Ser, L-Tyr, L-(4-$CF_3$)Phe, L-Ala, L-Phe, or L-Val, and $X^9$ is L-Thr.

In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^8$ is L-Bip, L-Ser, L-Tyr, L-(4-$CF_3$)Phe, L-Ala, L-Phe, or L-Val, $X^9$ is L-Thr, and $X^{10}$ is L-Thr or L-Ser. In yet another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, and $X^9$ is L-Thr. In another embodiment, $R^1$ is H or $(C_1$-$C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, and $X^{10}$ is L-Thr or L-Ser.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, $X^{10}$ is L-Thr or L-Ser, and $X^{11}$ is L-Ser, L-Asp, L-Asn, L-Pro, L-Ala, or L-Hse. In yet another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, $X^{10}$ is L-Thr or L-Ser, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^9$ is L-Thr, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, and $X^{10}$ is L-Thr or L-Ser. In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^{10}$ is L-Thr or L-Ser, and $X^{11}$ is L-Ser, L-Asp, L-Asn, L-Pro, L-Ala, or L-Hse.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^{10}$ is L-Thr or L-Ser, $X^{11}$ is L-Ser, L-Asp, L-Asn, L-Pro, L-Ala, or L-Hse, and $X^{12}$ is L-Val or L-Glu. In yet another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^{10}$ is L-Thr or L-Ser, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, and $X^{11}$ is L-Ser, L-Asp, L-Asn, L-Pro, L-Ala, or L-Hse. In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{11}$ is L-Ser, L-Asp, L-Asn, L-Pro, L-Ala, or L-Hse, and $X^{12}$ is L-Val or L-Glu.

In another embodiment, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{11}$ is L-Ser, L-Asp, L-Asn, L-Pro, L-Ala, or L-Hse, $X^{12}$ is L-Val or L-Glu, and $X^{13}$ is L-Phe.

In some embodiments of the Formulae above, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{12}$ is L-Val or L-Glu, and $X^{13}$ is L-Phe.

In some embodiments of the Formulae above, $R^1$ is H or $(C_1-C_4)$alkyl, $X^1$ is absent, Gly, Gly-L-Lys*, or Gly-D-Lys*, wherein * denotes the point of attachment to $NHR^1$, $X^2$ is L-Pro, $X^3$ is L-Arg, L-Ser, L-His, or L-Ala, $X^4$ is L-Asp, L-Asn, L-Glu, L-Lys, L-Gln, L-Pro, L-Ala, or L-(N-Me)Glu, $X^5$ is L-(N-Me)Ala or L-(N-Me)Glu, $X^6$ is L-Bip, L-(4-$CF_3$)Phe, L-(3,4-diCl)Phe, L-(3-F)Phe, or L-(4-Cl)Phe, $X^7$ is L-(N-Me)Ala or L-(N-Me)Phe, $X^8$ is L-Bip, L-Ser, L-Tyr, L-(4-$CF_3$)Phe, L-Ala, L-Phe, or L-Val, $X^9$ is L-Thr, $X^{10}$ is L-Thr or L-Ser, $X^{11}$ is L-Ser, L-Asp, L-Asn, L-Ala, or L-Hse, and $X^{13}$ is L-Phe.

Embodiment 1. A Polypeptide According to Formula (I) wherein:

$R^1$ is H or $(C_1-C_4)$alkyl;

$X^1$ is absent or Gly;

X² is L-Pro or D-Pro;
X³ is L-Arg, D-Arg, L-Ser, D-Ser, L-His, D-His, L-Ala, or D-Ala;
X⁴ is L-Asp, D-Asp, L-Asn, D-Asn, L-Glu, D-Glu, L-Lys, D-Lys, L-Gln, D-Gln, L-Pro, D-Pro, L-Ala, D-Ala, L-(N-Me)Glu, or D-(N-Me)Glu;
X⁵ is L-(N-Me)Ala, D-(N-Me)Ala, L-(N-Me)Glu, or D-(N-Me)Glu;
X⁶ is L-Bip, D-Bip, L-(4-CF₃)Phe, D-(4-CF₃)Phe, L-(3,4-diCl)Phe, D-(3,4-diCl)Phe, L-(3-F)Phe, D-(3-F)Phe, L-(4-Cl)Phe, or D-(4-Cl)Phe;
X⁷ is L-(N-Me)Ala, D-(N-Me)Ala, L-(N-Me)Phe, or D-(N-Me)Phe;
X⁸ is L-Bip, D-Bip, L-Ser, D-Ser, L-Tyr, D-Tyr, L-(4-CF₃)Phe, D-(4-CF₃)Phe, L-Ala, D-Ala, L-Phe, D-Phe, L-Val, or D-Val;
X⁹ is L-Thr or D-Thr;
X¹⁰ is L-Thr, D-Thr, L-Ser, or D-Ser;
X¹¹ is L-Ser, D-Ser, L-Asp, D-Asp, L-Asn, D-Asn, L-Pro, D-Pro, L-Ala, D-Ala, L-Hse, or D-Hse;
X¹² is L-Val, D-Val, L-Glu or D-Glu; and
X¹³ is L-Phe or D-Phe;
wherein:
Bip is 4-phenyl-phenylalanine;
Hse is homoserine;
(4-CF₃)Phe is 4-trifluoromethyl-phenylalanine;
(3,4-diCl)Phe is 3,4-dichloro-phenylalanine;
(3-F)Phe is 3-fluoro-phenylalanine; and
(4-Cl)Phe is 4-chloro-phenylalanine;

or pharmaceutically acceptable salts, hydrates, solvates, stereoisomers, or tautomers thereof.

Embodiment 2. The polypeptide according to Embodiment 1, wherein $X^{13}$ is L-Phe.

Embodiment 3. The polypeptide according to Embodiment 1 or 2, wherein $X^2$ is L-Pro.

Embodiment 4. The polypeptide according to any one of Embodiments 1-3, wherein $X^9$ is L-Thr.

Embodiment 5. The polypeptide according to Embodiment 1, having the Formula (II), Formula (III), Formula (IV), Formula (V), or Formula (VI).

Embodiment 6. The polypeptide according to any one of Embodiments 1-5, wherein $X^{12}$ is L-Val or L-Glu.

Embodiment 7. The polypeptide according to any one of Embodiments 1-6, wherein $X^{12}$ is L-Val or L-Glu.

Embodiment 8. The polypeptide according to any one of Embodiments 1-7, wherein $X^{12}$ is L-Val.

Embodiment 9. The polypeptide according to any one of Embodiments 1-8, wherein $X^1$ is absent.

Embodiment 10. The polypeptide according to any one of Embodiments 1-9, wherein $X^1$ is Gly.

Embodiment 11. The polypeptide according to any one of Embodiments 1-10, wherein $X^{10}$ is L-Thr or L-Ser.

Embodiment 12. The polypeptide according to any one of Embodiments 1-11, wherein $R^1$ is H or $(C_1-C_3)$alkyl.

Embodiment 13. The polypeptide according to any one of Embodiments 1-12, wherein $R^1$ is H.

Non-limiting illustrative polypeptides of the disclosure include:

| Ex. No. | Embodiment No. | Polypeptide Sequence |
|---|---|---|
| 1-1 | 14 | Ac*-F-V-D-T-T-S-(N-Me)F-B-(N-Me)E-N-S-P-C*-G-NH₂; or Ac*-(L-Phe)-(L-Val)-(L-Asp)-(L-Thr)-(L-Thr)-(L-Ser)-(L-(N-Me)Phe)-(L-Bip)-(L-(N-Me)Glu)-(L-Asn)-(L-Ser)-(L-Pro)-(L-Cys)*-(Gly)-NH₂; or |

L-Phe-L-Val-L-Asp-L-Thr-L-Thr-L-Ser-L-(N-Me)Phe-L-Bip-L-(N-Me)Glu-L-Asn-L-Ser-L-Pro-...

(SEQ ID No.: 1)

| 1-2 | 15 | Ac*-F-V-S-T-T-B-(N-Me)A-B-(N-Me)A-D-R-P-C*-G-NH₂; or Ac*-(L-Phe)-(L-Val)-(L-Ser)-(L-Thr)-(L-Thr)-(L-Bip)-(L-(N-Me)Ala)-(L-Bip)-(L-(N-Me)Ala)-(L-Asp)-(L-Arg)-(L-Pro)-(L-Cys)*-(Gly)-NH₂; or |

L-Phe-L-Val-L-Ser-L-Thr-L-Thr-L-Bip-L-(N-Me)Ala-L-Bip-L-(N-Me)Ala-L-Asp-L-Arg-L-Pro-...

(SEQ ID No.: 2)

-continued

| Ex. No. | Embodiment No. | Polypeptide Sequence |
|---|---|---|
| 1-3 | 16 | Ac*-F-V-D-T-T-S-(N-Me)F-B-(N-Me)A-N-S-P-C*-G-NH$_2$; or<br>Ac*-(L-Phe)-(L-Val)-(L-Asp)-(L-Thr)-(L-Thr)-(L-Ser)-(L-(N-Me)Phe)-(L-Bip)-(L-(N-Me)Ala)-(L-Asn)-(L-Ser)-(L-Pro)-(L-Cys)*-(Gly)-NH$_2$; or<br>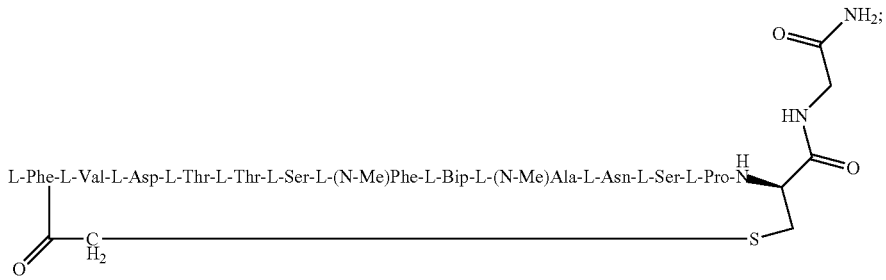<br>(SEQ ID No.: 3) |
| 1-4 | 17 | Ac*-F-V-D-S-T-Y-(N-Me)A-B-(N-Me)A-N-H-P-C*-G-NH$_2$; or<br>Ac*-(L-Phe)-(L-Val)-(L-Asp)-(L-Ser)-(L-Thr)-(L-Tyr)-(L-(N-Me)Ala)-(L-Bip)-(L-(N-Me)Ala)-(L-Asn)-(L-His)-(L-Pro)-(L-Cys)*-(Gly)-NH$_2$; or<br>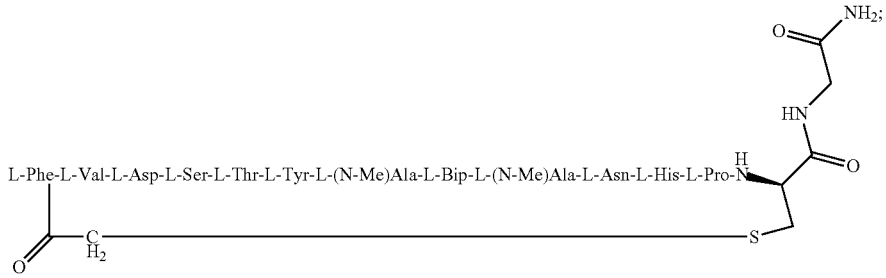<br>(SEQ ID No.: 4) |
| 1-5 | 18 | Ac*-F-V-D-T-T-S-(N-Me)F-B-(N-Me)A-E-S-P-C*-G-NH$_2$; or<br>Ac*-(L-Phe)-(L-Val)-(L-Asp)-(L-Thr)-(L-Thr)-(L-Ser)-(L-(N-Me)Phe)-(L-Bip)-(L-(N-Me)Ala)-(L-Glu)-(L-Ser)-(L-Pro)-(L-Cys)*-(Gly)-NH$_2$; or<br>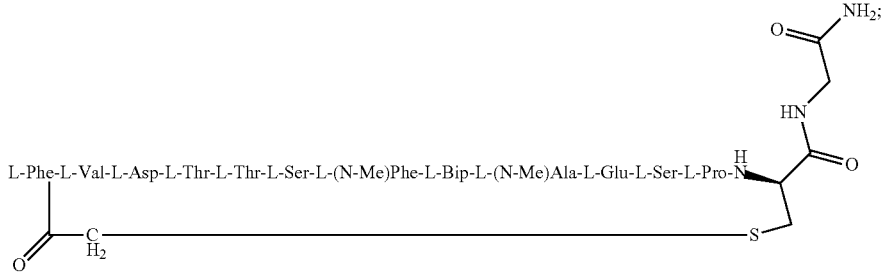<br>(SEQ ID No.: 5) |

| Ex. No. | Embodiment No. | Polypeptide Sequence |
|---|---|---|
| 1-6 | 19 | Ac*-F-V-D-T-T-S-(N-Me)F-(p-CF$_3$)F-(N-Me)A-E-S-P-C*-G-NH$_2$; or Ac*-(L-Phe)-(L-Val)-(L-Asp)-(L-Thr)-(L-Thr)-(L-Ser)-(L-(N-Me)Phe)-(L-(4-CF$_3$)Phe)-(L-(N-Me)Ala)-(L-Glu)-(L-Ser)-(L-Pro)-(L-Cys)*-(Gly)-NH$_2$; or |

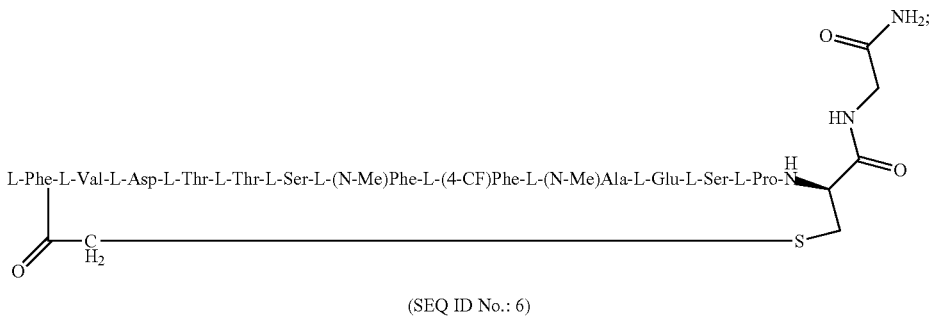

(SEQ ID No.: 6)

| 1-7 | 20 | Ac*-F-V-D-T-T-S-(N-Me)A-B-(N-Me)A-K-S-P-C*-G-NH$_2$; or Ac*-(L-Phe)-(L-Val)-(L-Asp)-(L-Thr)-(L-Thr)-(L-Ser)-(N-Me)Ala)-(L-Bip)-(N-Me)Ala)-(L-Lys)-(L-Ser)-(L-Pro)-(L-Cys)*-(Gly)-NH$_2$; or |

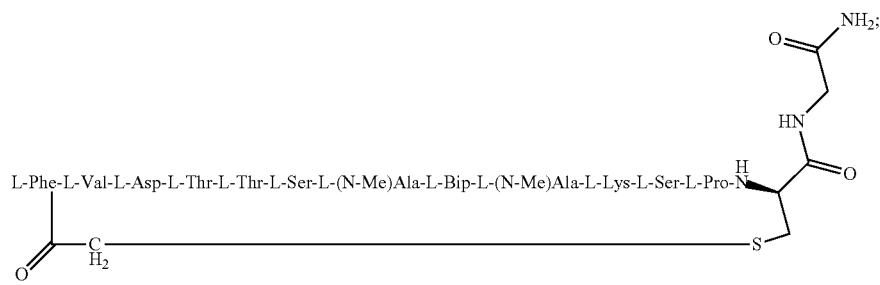

(SEQ ID No.: 7)

| 1-8 | 21 | Ac*-F-V-S-T-T-B-(N-Me)A-B-(N-Me)A-D-S-P-C*-G-NH$_2$; or Ac*-(L-Phe)-(L-Val)-(L-Ser)-(L-Thr)-(L-Thr)-(L-Bip)-(L-(N-Me)Ala)-(L-Bip)-(L-(N-Me) Ala)-(L-Asp)-(L-Ser)-(L-Pro)-(L-Cys)*-(Gly)-NH$_2$; or |

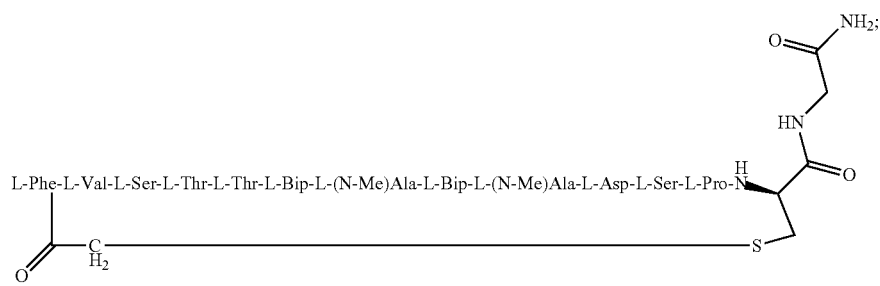

(SEQ ID No.: 8)

-continued

| Ex. No. | Embodiment No. | Polypeptide Sequence |
|---|---|---|
| 1-9 | 22 | Ac*-F-V-S-T-T-S-(N-Me)F-B-(N-Me)A-D-R-P-C*-G-NH$_2$; or Ac*-(L-Phe)-(L-Val)-(L-Ser)-(L-Thr)-(L-Thr)-(L-Ser)-(L-(N-Me)Phe)-(L-Bip)-(L-(N-Me)Ala)-(L-Asp)-(L-Arg)-(L-Pro)-(L-Cys)*-(Gly)-NH$_2$; or |

L-Phe-L-Val-L-Ser-L-Thr-L-Thr-L-Ser-L-(N-Me)Phe-L-Bip-L-(N-Me)Ala-L-Asp-L-Arg-L-Pro-N... -C(=O)-CH$_2$-S-...-Cys-C(=O)-NH-CH$_2$-C(=O)-NH$_2$ (SEQ ID No.: 9)

| 1-10 | 23 | Ac*-F-V-D-T-T-B-(N-Me)A-B-(N-Me)A-E-S-P-C*-G-NH$_2$; or Ac*-(L-Phe)-(L-Val)-(L-Asp)-(L-Thr)-(L-Thr)-(L-Bip)-(L-(N-Me)Ala)-(L-Bip)-(L-(N-Me)Ala)-(L-Glu)-(L-Ser)-(L-Pro)-(L-Cys)*-(Gly)-NH$_2$; or |

L-Phe-L-Val-L-Asp-L-Thr-L-Thr-L-Bip-L-(N-Me)Ala-L-Bip-L-(N-Me)Ala-L-Glu-L-Ser-L-Pro-N...-C(=O)-CH$_2$-S-...-Cys-C(=O)-NH-CH$_2$-C(=O)-NH$_2$ (SEQ ID No.: 10)

| 1-11 | 24 | Ac*-F-V-S-T-T-(p-CF$_3$)F-(N-Me)A-(p-CF$_3$)F-(N-Me)A-E-R-P-C*-G-NH$_2$; or Ac*-(L-Phe)-(L-Val)-(L-Ser)-(L-Thr)-(L-Thr)-(L-(4-CF$_3$)Phe)-(L-(N-Me)Ala)-(L-(4-CF$_3$)Phe)-(L-(N-Me)Ala)-(L-Glu)-(L-Arg)-(L-Pro)-(L-Cys)*-(Gly)-NH$_2$; or |

L-Phe-L-Val-L-Ser-L-Thr-L-Thr-L-(4-CF$_3$)Phe-L-(N-Me)Ala-L-(4-CF$_3$)Phe-L-(N-Me)Ala-L-Glu-L-Arg-L-Pro-N...-C(=O)-CH$_2$-S-...-Cys-C(=O)-NH-CH$_2$-C(=O)-NH$_2$ (SEQ ID No.: 11)

| Ex. No. | Embodiment No. | Polypeptide Sequence |
|---|---|---|
| 1-12 | 25 | Ac*-F-V-S-T-T-S-(N-Me)F-B-(N-Me)A-E-S-P-C*-G-NH$_2$; or Ac*-(L-Phe)-(L-Val)-(L-Ser)-(L-Thr)-(L-Thr)-(L-Ser)-(L-(N-Me)Phe)-(L-Bip)-(L-(N-Me)Ala)-(L-Glu)-(L-Ser)-(L-Pro)-(L-Cys)*-(Gly)-NH$_2$; or 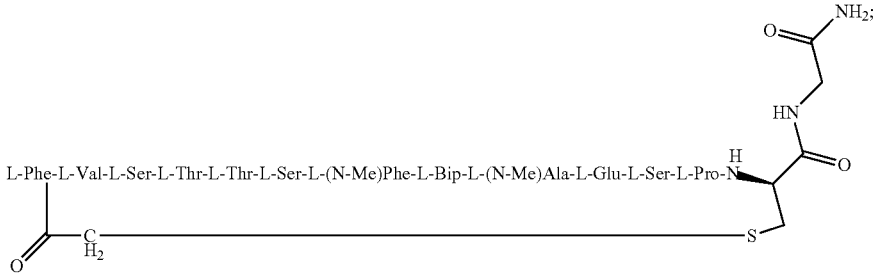 (SEQ ID No.: 12) |
| 1-13 | 26 | Ac*-F-V-S-T-T-B-(N-Me)F-B-(N-Me)A-E-S-P-C*-G-NH$_2$; or Ac*-(L-Phe)-(L-Val)-(L-Ser)-(L-Thr)-(L-Thr)-(L-Bip)-(L-(N-Me)Phe)-(L-Bip)-(L-(N-Me)Ala)-(L-Glu)-(L-Ser)-(L-Pro)-(L-Cys)*-(Gly)-NH$_2$; or 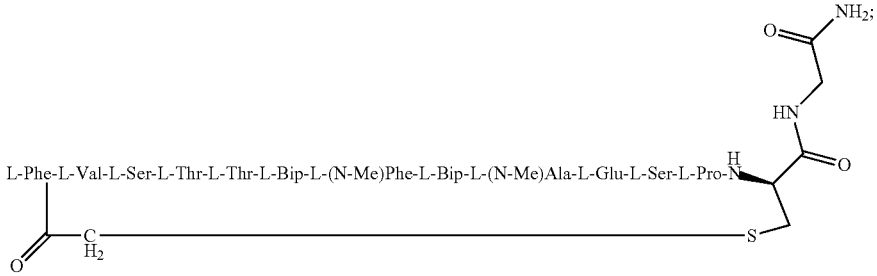 (SEQ ID No.: 13) |
| 1-14 | 27 | Ac*-F-V-S-T-T-B-(N-Me)A-(3,4-diCl)F-(N-Me)A-D-R-P-C*-G-NH$_2$; or Ac*-(L-Phe)-(L-Val)-(L-Ser)-(L-Thr)-(L-Thr)-(L-Bip)-(L-(N-Me)Ala)-(L-(3,4-diCl)Phe)-(L-(N-Me)Ala)-(L-Asp)-(L-Arg)-(L-Pro)-(L-Cys)*-(Gly)-NH$_2$; or 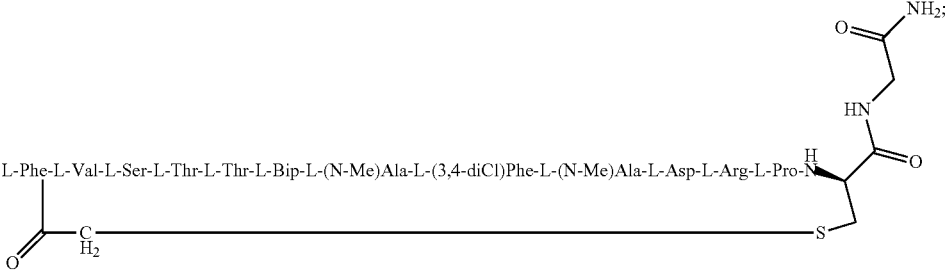 (SEQ ID No.: 14) |

-continued

| Ex. No. | Embodiment No. | Polypeptide Sequence |
|---|---|---|
| 1-15 | 28 | Ac*-F-V-S-T-T-B-(N-Me)A-(3-F)F-(N-Me)A-D-R-P-C*-G-NH$_2$; or Ac*-(L-Phe)-(L-Val)-(L-Ser)-(L-Thr)-(L-Thr)-(L-Bip)-(L-(N-Me)Ala)-(L-(3-F)Phe)-(L-(N-Me) Ala)-(L-Asp)-(L-Arg)-(L-Pro)-(L-Cys)*-(Gly)-NH$_2$; or 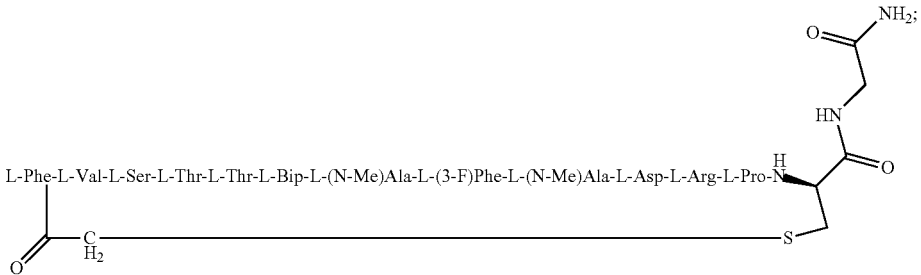 (SEQ ID No.: 15) |
| 1-16 | 29 | Ac*-F-V-D-T-T-A-(N-Me)F-B-(N-Me)A-E-A-P-C*-G-NH$_2$; or Ac*-(L-Phe)-(L-Val)-(L-Asp)-(L-Thr)-(L-Thr)-(L-Ala)-(L-(N-Me)Phe)-(L-Bip)-(L-(N-Me)Ala)-(L-Glu)-(L-Ala)-(L-Pro)-(L-Cys)*-(Gly)-NH$_2$; or 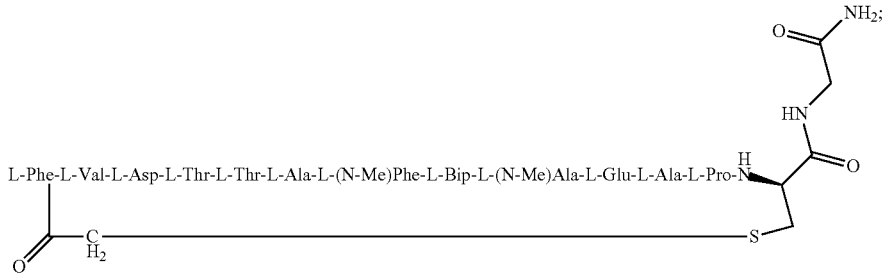 (SEQ ID No.: 16) |
| 1-17 | 30 | Ac*-F-V-D-T-T-F-(N-Me)A-B-(N-Me)A-E-S-P-C*-G-NH$_2$; or Ac*-(L-Phe)-(L-Val)-(L-Asp)-(L-Thr)-(L-Thr)-(L-Phe)-(L-(N-Me)Ala)-(L-Bip)-(L-(N-Me)Ala)-(L-Glu)-(L-Ser)-(L-Pro)-(L-Cys)*-(Gly)-NH$_2$; or 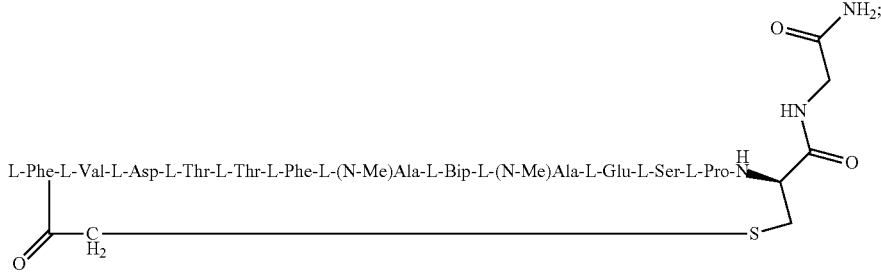 (SEQ ID No.: 17) |

| Ex. No. | Embodiment No. | Polypeptide Sequence |
|---|---|---|
| 1-18 | 31 | Ac*-F-V-N-T-T-A-(N-Me)F-B-(N-Me)A-Q-A-P-C*-G-NH₂; or<br>Ac*-(L-Phe)-(L-Val)-(L-Asn)-(L-Thr)-(L-Thr)-(L-Ala)-(L-(N-Me)Phe)-(L-Bip)-(L-(N-Me)Ala)-(L-Gln)-(L-Ala)-(L-Pro)-(L-Cys)*-(Gly)-NH₂; or<br>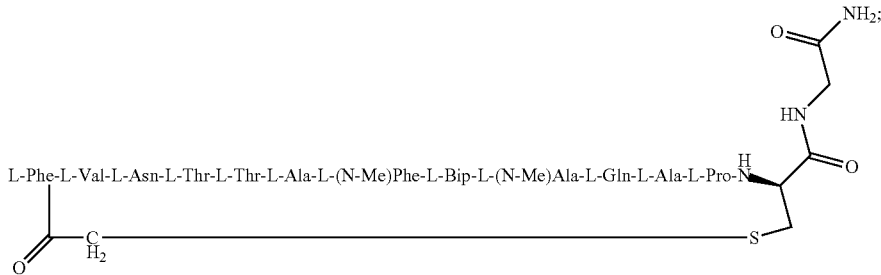<br>(SEQ ID No.: 18) |
| 1-19 | 32 | Ac*-F-V-P-T-T-B-(N-Me)A-B-(N-Me)A-D-R-P-C*-G-NH₂; or<br>Ac*-(L-Phe)-(L-Val)-(L-Pro)-(L-Thr)-(L-Thr)-(L-Bip)-(L-(N-Me)Ala)-(L-Bip)-(L-(N-Me)Ala)-(L-Asp)-(L-Arg)-(L-Pro)-(L-Cys)*-(Gly)-NH₂; or<br>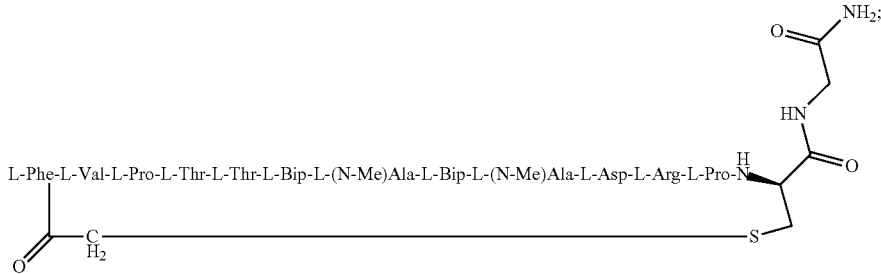<br>(SEQ ID No.: 19) |
| 1-20 | 33 | Ac*-F-V-S-T-T-B-(N-Me)A-B-(N-Me)A-P-S-P-C*-G-NH₂; or<br>Ac*-(L-Phe)-(L-Val)-(L-Ser)-(L-Thr)-(L-Thr)-(L-Bip)-(L-(N-Me)Ala)-(L-Bip)-(L-(N-Me)Ala)-(L-Pro)-(L-Ser)-(L-Pro)-(L-Cys)*-(Gly)-NH₂; or<br>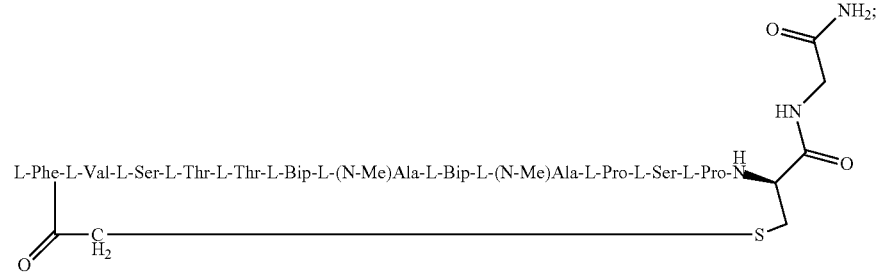<br>(SEQ ID No.: 20) |

| Ex. No. | Embodiment No. | Polypeptide Sequence |
|---|---|---|
| 1-21 | 34 | Ac*-F-V-P-T-T-A-(N-Me)F-B-(N-Me)A-E-A-P-C*-G-NH₂; or<br>Ac*-(L-Phe)-(L-Val)-(L-Pro)-(L-Thr)-(L-Thr)-(L-Ala)-(L-(N-Me)Phe)-(L-Bip)-(L-(N-Me)Ala)-(L-Glu)-(L-Arg)-(L-Pro)-(L-Cys)*-(Gly)-NH₂; or<br>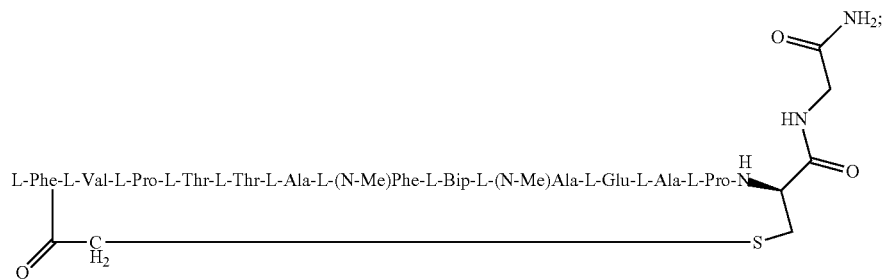<br>(SEQ ID No.: 21) |
| 1-22 | 35 | Ac*-F-V-A-T-T-F-(N-Me)A-B-(N-Me)A-K-A-P-C*-G-NH₂; or<br>Ac*-(L-Phe)-(L-Val)-(L-Ala)-(L-Thr)-(L-Thr)-(L-Phe)-(L-(N-Me)Ala)-(L-Bip)-(L-(N-Me)Ala)-(L-Lys)-(L-Ala)-(L-Pro)-(L-Cys)*-(Gly)-NH₂; or<br>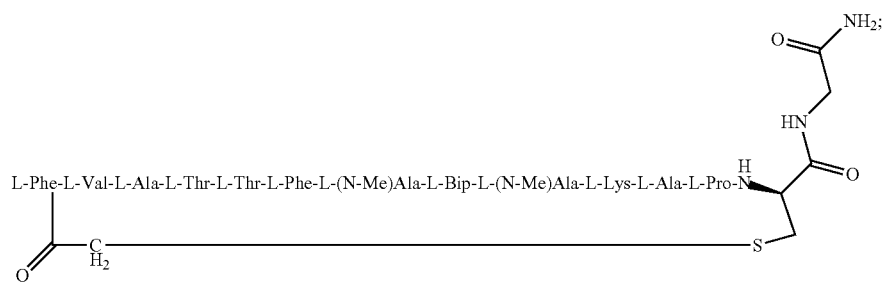<br>(SEQ ID No.: 22) |
| 1-23 | 36 | Ac*-F-V-N-T-T-F-(N-Me)A-B-(N-Me)A-K-A-P-C*-G-NH₂; or<br>Ac*-(L-Phe)-(L-Val)-(L-Asn)-(L-Thr)-(L-Thr)-(L-Phe)-(L-(N-Me)Ala)-(L-Bip)-(L-(N-Me)Ala)-(L-Lys)-(L-Ala)-(L-Pro)-(L-Cys)*-(Gly)-NH₂; or<br>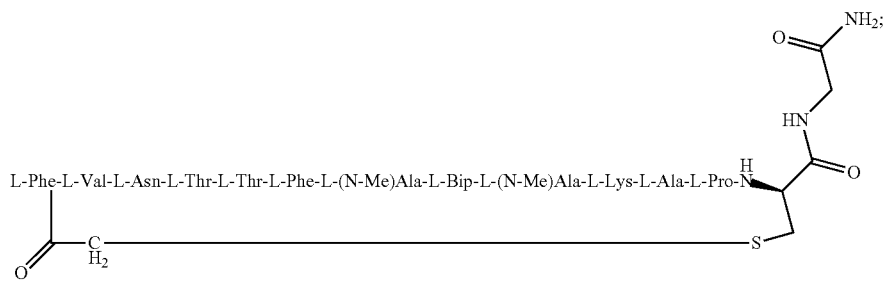<br>(SEQ ID No.: 23) |

| Ex. No. | Embodiment No. | Polypeptide Sequence |
|---|---|---|
| 1-24 | 37 | Ac*-F-V-S-T-T-F-(N-Me)A-B-(N-Me)A-E-A-P-C*-G-NH$_2$; or<br>Ac*-(L-Phe)-(L-Val)-(L-Ser)-(L-Thr)-(L-Thr)-(L-Phe)-(L-(N-Me)Ala)-(L-Bip)-(L-(N-Me)Ala)-(L-Glu)-(L-Ala)-(L-Pro)-(L-Cys)*-(Gly)-NH$_2$; or<br>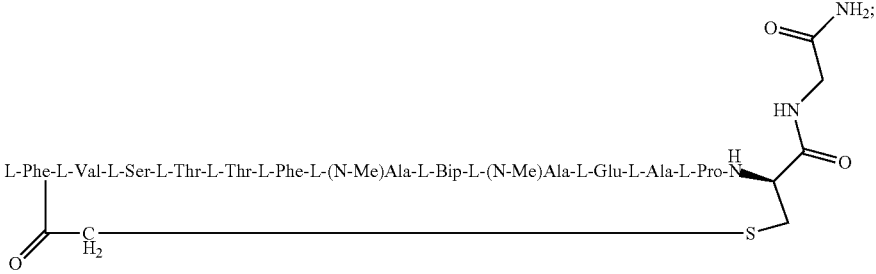<br>(SEQ ID No.: 24) |
| 1-25 | 38 | Ac*-F-V-S-T-T-B-(N-Me)A-B-(N-Me)A-E-S-P-C*-G-NH$_2$; or<br>Ac*-(L-Phe)-(L-Val)-(L-Ser)-(L-Thr)-(L-Thr)-(L-Bip)-(L-(N-Me)Ala)-(L-Bip)-(L-(N-Me)Ala)-(L-Glu)-(L-Ser)-(L-Pro)-(L-Cys)*-(Gly)-NH$_2$; or<br>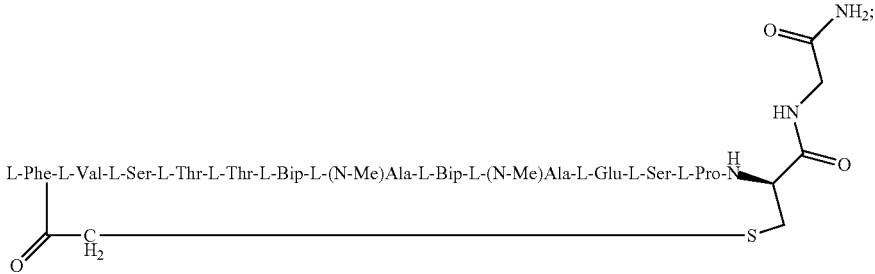<br>(SEQ ID No.: 25) |
| 1-26 | 39 | Ac*-F-V-D-T-T-B-(N-Me)A-(3,4-diCl)F-(N-Me)A-E-S-P-C*-G-NH$_2$; or<br>Ac*-(L-Phe)-(L-Val)-(L-Asp)-(L-Thr)-(L-Thr)-(L-Bip)-(L-(N-Me)Ala)-(L-(3,4-diCl)Phe)-(L-(N-Me)Ala)-(L-Glu)-(L-Ser)-(L-Pro)-(L-Cys)*-(Gly)-NH$_2$; or<br>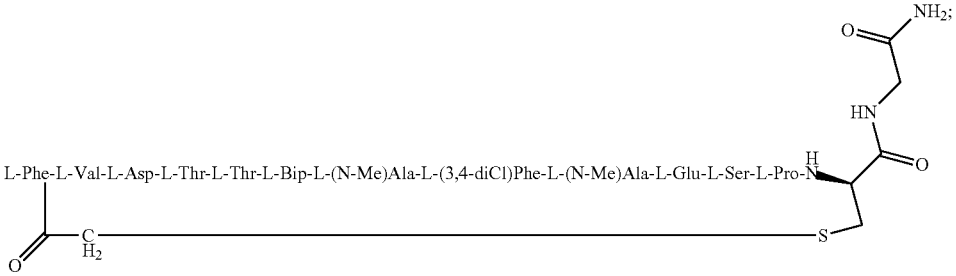<br>(SEQ ID No.: 26) |

| Ex. No. | Embodiment No. | Polypeptide Sequence |
|---|---|---|
| 1-27 | 40 | Ac*-F-E-N-T-T-F-(N-Me)A-B-(N-Me)A-A-S-P-C*-G-NH$_2$; or<br>Ac*-(L-Phe)-(L-Glu)-(L-Asn)-(L-Thr)-(L-Thr)-(L-Phe)-(L-(N-Me)Ala)-(L-Bip)-(L-(N-Me)Ala)-(L-Ala)-(L-Ser)-(L-Pro)-(L-Cys)*-(Gly)-NH$_2$; or<br>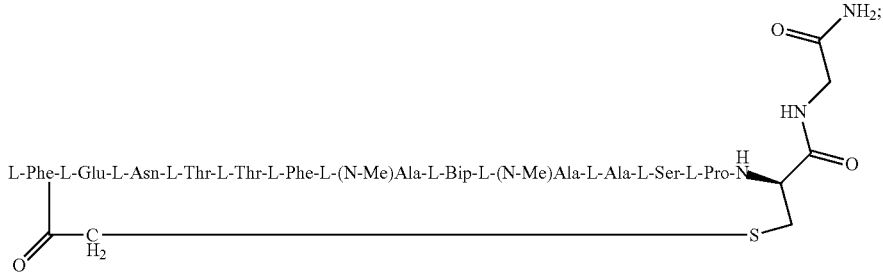<br>(SEQ ID No.: 27) |
| 2-1 | 41 | Ac*-F-V-P-T-T-F-(N-Me)A-(p-Cl)F-(N-Me)A-P-A-P-C*-NH$_2$; or<br>Ac*-(L-Phe)-(L-Val)-(L-Pro)-(L-Thr)-(L-Thr)-(L-Phe)-(L-(N-Me)Ala)-(L-(4-Cl)Phe)-(L-(N-Me)Ala)-(L-Pro)-(L-Ala)-(L-Pro)-(L-Cys)*-NH$_2$; or<br>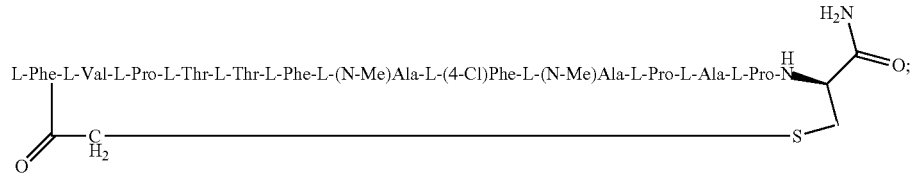<br>(SEQ ID No.: 28) |
| 2-2 | 42 | Ac*-F-V-P-T-T-F-(N-Me)A-(p-Cl)F-(N-Me)A-D-A-P-C*-NH$_2$; or<br>Ac*-(L-Phe)-(L-Val)-(L-Pro)-(L-Thr)-(L-Thr)-(L-Phe)-(L-(N-Me)Ala)-(L-(4-Cl)Phe)-(L-(N-Me)Ala)-(L-Asp)-(L-Ala)-(L-Pro)-(L-Cys)*-NH$_2$; or<br>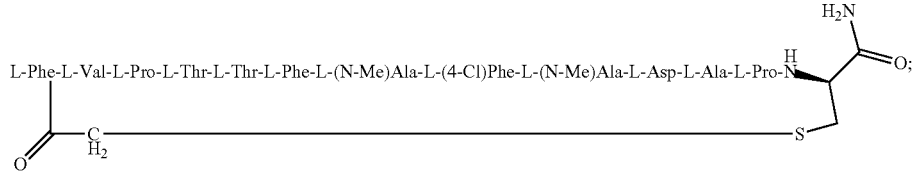<br>(SEQ ID No.: 29) |
| 2-3 | 43 | Ac*-F-V-HomoSer-T-T-F-(N-Me)A-(p-Cl)F-(N-Me)A-D-A-P-C*-NH$_2$; or<br>Ac*-(L-Phe)-(L-Val)-(L-Hse)-(L-Thr)-(L-Thr)-(L-Phe)-(L-(N-Me)Ala)-(L-(4-Cl)Phe)-(L-(N-Me)Ala)-(L-Asp)-(L-Ala)-(L-Pro)-(L-Cys)*-NH$_2$; or<br>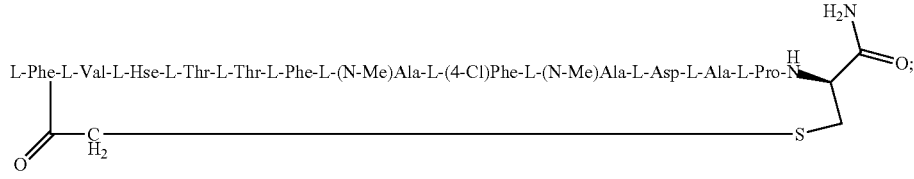<br>(SEQ ID No.: 30) |

| Ex. No. | Embodiment No. | Polypeptide Sequence |
|---|---|---|
| 2-4 | 44 | Ac*-F-V-S-T-T-B-(N-Me)A-B-(N-Me)A-D-R-P-C*-NH$_2$; or<br>Ac*-(L-Phe)-(L-Val)-(L-Ser)-(L-Thr)-(L-Thr)-(L-Bip)-(L-(N-Me)Ala)-(L-Bip)-(L-(N-Me)Ala)-(L-Asp)-(L-Arg)-(L-Pro)-(L-Cys)*-NH$_2$; or<br><br>L-Phe-L-Val-L-Ser-L-Thr-L-Thr-L-Bip-L-(N-Me)Ala-L-Bip-L-(N-Me)Ala-L-Asp-L-Arg-L-Pro-cyclic[CH$_2$-C(O)...S-Cys-C(O)NH$_2$]<br><br>(SEQ ID No.: 31) |
| 2-5 | 45 | Ac*-F-V-A-T-T-F-(N-Me)A-(p-Cl)F-(N-Me)A-N-A-P-C*-NH$_2$; or<br>Ac*-(L-Phe)-(L-Val)-(L-Ala)-(L-Thr)-(L-Thr)-(L-Phe)-(L-(N-Me)Ala)-(L-(4-Cl)Phe)-(L-(N-Me)Ala)-(L-Asn)-(L-Ala)-(L-Pro)-(L-Cys)*-NH$_2$; or<br><br>L-Phe-L-Val-L-Ala-L-Thr-L-Thr-L-Phe-L-(N-Me)Ala-L-(4-Cl)Phe-L-(N-Me)Ala-L-Asn-L-Ala-L-Pro-cyclic[CH$_2$-C(O)...S-Cys-C(O)NH$_2$]<br><br>(SEQ ID No.: 32) |
| 2-6 | 46 | Ac*-F-V-P-T-T-V-(N-Me)A-(p-Cl)F-(N-Me)A-E-A-P-C*-NH$_2$; or<br>Ac*-(L-Phe)-(L-Val)-(L-Pro)-(L-Thr)-(L-Thr)-(L-Val)-(L-(N-Me)Ala)-(L-(4-Cl)Phe)-(L-(N-Me)Ala)-(L-Glu)-(L-Ala)-(L-Pro)-(L-Cys)*-NH$_2$; or<br><br>L-Phe-L-Val-L-Pro-L-Thr-L-Thr-L-Val-L-(N-Me)Ala-L-(4-Cl)Phe-L-(N-Me)Ala-L-Glu-L-Ala-L-Pro-cyclic[CH$_2$-C(O)...S-Cys-C(O)NH$_2$]<br><br>(SEQ ID No.: 33) |
| 3-1 | 47 | Ac*-F-V-N-T-T-F-(N-Me)A-B-(N-Me)A-(N-Me)E-A-P-C*-NHEt; or<br>Ac*-(L-Phe)-(L-Val)-(L-Asn)-(L-Thr)-(L-Thr)-(L-Phe)-(L-(N-Me)Ala)-(L-Bip)-(L-(N-Me)Ala)-(L-(N-Me)Glu)-(L-Ala)-(L-Pro)-(L-Cys)*-NHEt; or<br><br>L-Phe-L-Val-L-Asn-L-Thr-L-Thr-L-Phe-L-(N-Me)Ala-L-Bip-L-(N-Me)Ala-L-(N-Me)Glu-L-Ala-L-Pro-cyclic[CH$_2$-C(O)...S-Cys-C(O)NHEt]<br><br>(SEQ ID No.: 34) |

| Ex. No. | Embodiment No. | Polypeptide Sequence |
|---|---|---|
| 3-2 | 48 | Ac*-F-V-P-T-T-F-(N-Me)A-B-(N-Me)A-E-A-P-C*-NHEt; or<br>Ac*-(L-Phe)-(L-Val)-(L-Pro)-(L-Thr)-(L-Thr)-(L-Phe)-(L-(N-Me)Ala)-(L-Bip)-(L-(N-Me)Ala)-(L-Glu)-(L-Ala)-(L-Pro)-(L-Cys)*-NHEt; or<br>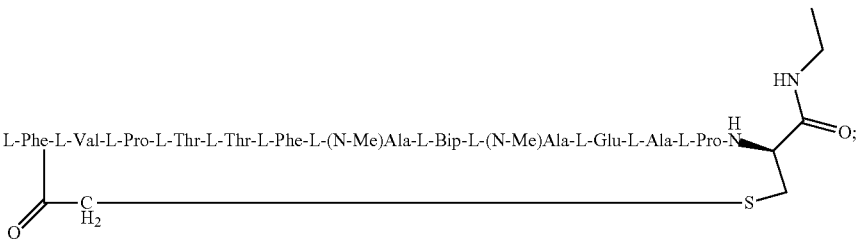<br>(SEQ ID No.: 35) |
| 3-3 | 49 | Ac*-F-V-P-T-T-B-(N-Me)A-B-(N-Me)A-E-A-P-C*-NHEt; or<br>Ac*-(L-Phe)-(L-Val)-(L-Pro)-(L-Thr)-(L-Thr)-(L-Bip)-(L-(N-Me)Ala)-(L-Bip)-(L-(N-Me)Ala)-(L-Glu)-(L-Ala)-(L-Pro)-(L-Cys)*-NHEt; or<br>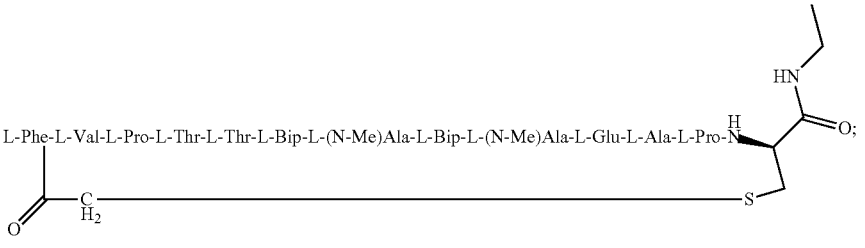<br>(SEQ ID No.: 36); |
| 3-4 | 50 | Ac*-F-V-P-T-T-B-(N-Me)A-B-(N-Me)A-A-A-P-C*-NHEt; or<br>Ac*-(L-Phe)-(L-Val)-(L-Pro)-(L-Thr)-(L-Thr)-(L-Bip)-(L-(N-Me)Ala)-(L-Bip)-(L-(N-Me)Ala)-(L-Ala)-(L-Ala)-(L-Pro)-(L-Cys)*-NHEt; or<br>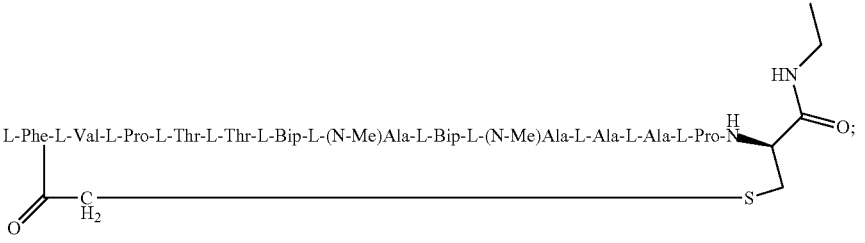<br>(SEQ ID No.: 37); and |

| Ex. No. | Embodiment No. | Polypeptide Sequence |
|---|---|---|
| 3-5 | 51 | Ac*-F-V-P-T-T-B-(N-Me)A-B-(N-Me)A-E-A-P-C*-G-K-NH$_2$; or Ac*-(L-Phe)-(L-Val)-(L-Pro)-(L-Thr)-(L-Thr)-(L-Bip)-(L-(N-Me)Ala)-(L-Bip)-(L-(N-Me)Ala)-(L-Glu)-(L-Ala)-(L-Pro)-(L-Cys)*-(Gly)-(L-Lys)-NH$_2$; or 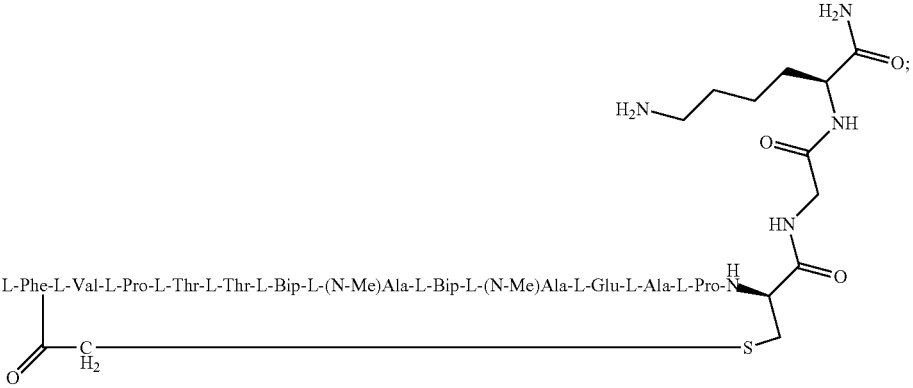 (SEQ ID No.: 38). | wherein Ac is acetyl and wherein acetyl labeled with the "*" and the amino acid labeled with the "*" are linked via a sulfide bond formed via their side chain or terminus.

wherein Ac is acetyl and wherein acetyl labeled with the "*" and the amino acid labeled with the "*" are linked via a sulfide bond formed via their side chain or terminus.

Embodiment 51. A pharmaceutical composition comprising a therapeutically effective amount of a cyclic polypeptide according to any one of Embodiments 1-50, or a pharmaceutically acceptable salt thereof, and one or more pharmaceutically acceptable carriers or excipients.

Embodiment 52. A combination comprising a polypeptide according to any one of Embodiments 1-50, or a pharmaceutically acceptable salt thereof, and one or more additional therapeutically active agents.

Embodiment 53. The combination according to Embodiment 52, wherein the additional therapeutically active agent is a statin.

Embodiment 54. The pharmaceutical composition according to Embodiment 51 or combination according to any one of Embodiment 52 or 53 for use in the treatment, prevention, amelioration, or delay in the progression of a PCSK9-mediated disease or disorder.

Embodiment 55. The pharmaceutical composition or the combination according to Embodiment 54, wherein said PCSK9-mediated disease or disorder or the disease or disorder requiring inhibition of PCSK9 activity is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 56. A method of modulating PCSK9 comprising administering to a patient in need thereof a cyclic polypeptide of any one of Embodiments 1-50, or a pharmaceutically acceptable salt thereof.

Embodiment 57. A method of inhibiting PCSK9 comprising administering to a patient in need thereof a cyclic polypeptide of any one of Embodiments 1-50, or a pharmaceutically acceptable salt thereof.

Embodiment 58. A method for treating, preventing, ameliorating or delaying the progression of a PCSK9-mediated disease or disorder comprising the step of administering to a patient in need thereof a therapeutically effective amount of a cyclic polypeptide according to any one of Embodiments 1-50, or a pharmaceutically acceptable salt thereof.

Embodiment 59. The method of Embodiment 58, wherein said PCSK9-mediated disease or disorder is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 60. A method of (i) reducing Lp(a), (ii) reducing Lp(a) plasma levels, (iii) reducing Lp(a) serum levels, (iv) reducing serum TRL or LDL levels, (v) reducing serum triglyceride levels, (vi) reducing LDL-C, (vii) reducing total plasma apoB concentrations, (viii) reducing LDL apoB, (ix) reducing TRL apoB, or (x) reducing non HDL-C, the method comprising administering to a patient in need thereof a therapeutically effective amount of a cyclic polypeptide of any one of Embodiments 1-50, or a pharmaceutically acceptable salt thereof to the patient, thereby reducing LDL-C in the patient.

Embodiment 61. The method of claims any one of Embodiments 56-60, wherein administering is performed orally, parentally, subcutaneously, by injection, or by infusion.

Embodiment 62. A cyclic polypeptide according to any one of Embodiments 1-50, or a pharmaceutically acceptable salt thereof, for use in the treatment of a PCSK9-mediated disease or disorder.

Embodiment 63. A cyclic polypeptide according to any one of Embodiments 1-50, or a pharmaceutically acceptable salt thereof, for use in the treatment, prevention, amelioration or delay of progression or for use in the treatment, prevention, amelioration or delay of progression of a disease or disorder requiring inhibition of PCSK9.

Embodiment 64. Use of a polypeptide according to any one of Embodiments 1-50, or a pharmaceutically acceptable salt thereof, for the treatment, prevention, amelioration or delay of progression of a PCSK9-mediated disease or disorder or for the treatment, prevention, amelioration or delay of progression of a disease or disorder requiring inhibition of PCSK9.

Embodiment 65. Use of a polypeptide according to any one of Embodiments 1-50, or a pharmaceutically acceptable salt thereof, in the manufacture of a medicament for the treatment, prevention, amelioration or delay of progression of a PCSK9-mediated disease or disorder or for the treatment, prevention, amelioration or delay of progression of a disease or disorder requiring inhibition of PCSK9.

Embodiment 66. A method for treating, preventing, ameliorating or delaying the progression of a PCSK9-mediated disease or disorder or of disease or disorder requiring inhibition of PCSK9 or of PCSK9 activity comprising the step of administering to a patient in need thereof a therapeutically effective amount of a polypeptide according to any one of Embodiments 1-50, or a pharmaceutically acceptable salt thereof.

Embodiment 67. The polypeptide for use according to Embodiment 63, the use of a polypeptide according to Embodiment 64 or 65, or the method for according to Embodiment 66, wherein said PCSK9-mediated disease or disorder or the disease or disorder requiring inhibition of PCSK9 is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 68. A polypeptide according to Formula (I), wherein:

$R^1$ is H or $(C_1-C_4)$alkyl;
$X^1$ is absent, Gly, Gly-L-Lys*, or Gly-D-Lys*, wherein * denotes the point of attachment to $NHR^1$;
$X^2$ is L-Pro or D-Pro;
$X^3$ is L-Arg, D-Arg, L-Ser, D-Ser, L-His, D-His, L-Ala, or D-Ala;
$X^4$ is L-Asp, D-Asp, L-Asn, D-Asn, L-Glu, D-Glu, L-Lys, D-Lys, L-Gln, D-Gln, L-Pro, D-Pro, L-Ala, D-Ala, L-(N-Me)Glu, or D-(N-Me)Glu;
$X^5$ is L-(N-Me)Ala, D-(N-Me)Ala, L-(N-Me)Glu, or D-(N-Me)Glu;
$X^6$ is L-Bip, D-Bip, L-(4-CF$_3$)Phe, D-(4-CF$_3$)Phe, L-(3,4-diCl)Phe, D-(3,4-diCl)Phe, L-(3-F)Phe, D-(3-F)Phe, L-(4-Cl)Phe, or D-(4-Cl)Phe;
$X^7$ is L-(N-Me)Ala, D-(N-Me)Ala, L-(N-Me)Phe, or D-(N-Me)Phe;
$X^8$ is L-Bip, D-Bip, L-Ser, D-Ser, L-Tyr, D-Tyr, L-(4-CF$_3$)Phe, D-(4-CF$_3$)Phe, L-Ala, D-Ala, L-Phe, D-Phe, L-Val, or D-Val;
$X^9$ is L-Thr or D-Thr;
$X^{10}$ is L-Thr, D-Thr, L-Ser, or D-Ser;
$X^{11}$ is L-Ser, D-Ser, L-Asp, D-Asp, L-Asn, D-Asn, L-Pro, D-Pro, L-Ala, D-Ala, L-Hse, or D-Hse;
$X^{12}$ is L-Val, D-Val, L-Glu or D-Glu; and
$X^{13}$ is L-Phe or D-Phe;
wherein:
Bip is 4-phenyl-phenylalanine;
Hse is homoserine;
(4-CF$_3$)Phe is 4-trifluoromethyl-phenylalanine;
(3,4-diCl)Phe is 3,4-dichloro-phenylalanine;
(3-F)Phe is 3-fluoro-phenylalanine; and
(4-Cl)Phe is 4-chloro-phenylalanine;
or pharmaceutically acceptable salts, hydrates, solvates, stereoisomers, or tautomers thereof.'

Embodiment 69. The polypeptide according to Embodiment 68, wherein:

$R^1$ is H or $(C_1-C_4)$alkyl;
$X^1$ is absent or Gly;
$X^2$ is L-Pro or D-Pro;
$X^3$ is L-Arg, D-Arg, L-Ser, D-Ser, L-His, D-His, L-Ala, or D-Ala;
$X^4$ is L-Asp, D-Asp, L-Asn, D-Asn, L-Glu, D-Glu, L-Lys, D-Lys, L-Gln, D-Gln, L-Pro, D-Pro, L-Ala, D-Ala, L-(N-Me)Glu, or D-(N-Me)Glu;
$X^5$ is L-(N-Me)Ala, D-(N-Me)Ala, L-(N-Me)Glu, or D-(N-Me)Glu;
$X^6$ is L-Bip, D-Bip, L-(4-CF$_3$)Phe, D-(4-CF$_3$)Phe, L-(3,4-diCl)Phe, D-(3,4-diCl)Phe, L-(3-F)Phe, D-(3-F)Phe, L-(4-Cl)Phe, or D-(4-Cl)Phe;
$X^7$ is L-(N-Me)Ala, D-(N-Me)Ala, L-(N-Me)Phe, or D-(N-Me)Phe;
$X^8$ is L-Bip, D-Bip, L-Ser, D-Ser, L-Tyr, D-Tyr, L-(4-CF$_3$)Phe, D-(4-CF$_3$)Phe, L-Ala, D-Ala, L-Phe, D-Phe, L-Val, or D-Val;
$X^9$ is L-Thr or D-Thr;
$X^{10}$ is L-Thr, D-Thr, L-Ser, or D-Ser;
$X^{11}$ is L-Ser, D-Ser, L-Asp, D-Asp, L-Asn, D-Asn, L-Pro, D-Pro, L-Ala, D-Ala, L-Hse, or D-Hse;
$X^{12}$ is L-Val, D-Val, L-Glu or D-Glu; and
$X^{13}$ is L-Phe or D-Phe;
wherein:
Bip is 4-phenyl-phenylalanine;
Hse is homoserine;
(4-CF$_3$)Phe is 4-trifluoromethyl-phenylalanine;
(3,4-diCl)Phe is 3,4-dichloro-phenylalanine;
(3-F)Phe is 3-fluoro-phenylalanine; and
(4-Cl)Phe is 4-chloro-phenylalanine;
or pharmaceutically acceptable salts, hydrates, solvates, stereoisomers, or tautomers thereof.

Embodiment 70. The polypeptide according to Embodiment 68 or 69, wherein $X^{13}$ is L-Phe.

Embodiment 71. The polypeptide according to any one of Embodiments 68-70, wherein $X^2$ is L-Pro.

Embodiment 72. The polypeptide according to any one of Embodiments 68-71, wherein $X^9$ is L-Thr.

Embodiment 73. The polypeptide according to Embodiment 68 or 69, having the Formula (II), Formula (III), Formula (IV), Formula (V), or Formula (VI).

Embodiment 74. The polypeptide according to any one of Embodiments 68-73, wherein $X^{12}$ is L-Val or L-Glu.

Embodiment 75. The polypeptide according to any one of Embodiments 68-74, wherein $X^{12}$ is L-Val or L-Glu.

Embodiment 76. The polypeptide according to any one of Embodiments 68-75, wherein $X^{12}$ is L-Val.

Embodiment 77. The polypeptide according to any one of Embodiments 68-76, wherein $X^1$ is absent.

Embodiment 78. The polypeptide according to any one of Embodiments 68-77, wherein $X^1$ is Gly.

Embodiment 79. The polypeptide according to any one of Embodiments 68-78, wherein $X^{10}$ is L-Thr or L-Ser.

Embodiment 80. The polypeptide according to any one of Embodiments 68-79, wherein $R^1$ is H or $(C_1-C_3)$alkyl.

Embodiment 81. The polypeptide according to any one of Embodiments 68-80, wherein $R^1$ is H.

Embodiment 82. A pharmaceutical composition comprising a therapeutically effective amount of a cyclic polypeptide according to any one of Embodiments 68-81 and 14-51, or a pharmaceutically acceptable salt thereof, and one or more pharmaceutically acceptable carriers or excipients.

Embodiment 83. A combination comprising a polypeptide according to any one of Embodiments 68-81 and 14-51, or a pharmaceutically acceptable salt thereof, and one or more additional therapeutically active agents.

Embodiment 84. The combination according to Embodiment 83, wherein the additional therapeutically active agent is a statin.

Embodiment 85. The pharmaceutical composition according to Embodiment 82 or combination according to any one of Embodiment 83 or 84 for use in the treatment, prevention, amelioration, or delay in the progression of a PCSK9-mediated disease or disorder.

Embodiment 86. The pharmaceutical composition or the combination according to Embodiment 85, wherein said PCSK9-mediated disease or disorder or the disease or disorder requiring inhibition of PCSK9 activity is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 87. A method of modulating PCSK9 comprising administering to a patient in need thereof a cyclic polypeptide of any one of Embodiments 68-81 and 14-51, or a pharmaceutically acceptable salt thereof.

Embodiment 88. A method of inhibiting PCSK9 comprising administering to a patient in need thereof a cyclic polypeptide of any one of Embodiments 68-81 and 14-51, or a pharmaceutically acceptable salt thereof.

Embodiment 89. A method for treating, preventing, ameliorating or delaying the progression of a PCSK9-mediated disease or disorder comprising the step of administering to a patient in need thereof a therapeutically effective amount of a cyclic polypeptide according to any one of Embodiments 68-81 and 14-51, or a pharmaceutically acceptable salt thereof.

Embodiment 90. The method of Embodiment 89, wherein said PCSK9-mediated disease or disorder is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

Embodiment 91. A method of (i) reducing Lp(a), (ii) reducing Lp(a) plasma levels, (iii) reducing Lp(a) serum levels, (iv) reducing serum TRL or LDL levels, (v) reducing serum triglyceride levels, (vi) reducing LDL-C, (vii) reducing total plasma apoB concentrations, (viii) reducing LDL apoB, (ix) reducing TRL apoB, or (x) reducing non HDL-C, the method comprising administering to a patient in need thereof a therapeutically effective amount of a cyclic polypeptide of any one of Embodiments 68-81 and 14-51, or a pharmaceutically acceptable salt thereof to the patient, thereby reducing LDL-C in the patient.

Embodiment 92. The method of claims any one of Embodiments 87-91, wherein administering is performed orally, parentally, subcutaneously, by injection, or by infusion.

Embodiment 93. A cyclic polypeptide according to any one of Embodiments 68-81 and 14-51, or a pharmaceutically acceptable salt thereof, for use in the treatment of a PCSK9-mediated disease or disorder.

Embodiment 94. A cyclic polypeptide according to any one of Embodiments 68-81 and 14-51, or a pharmaceutically acceptable salt thereof, for use in the treatment, prevention, amelioration or delay of progression or for use in the treatment, prevention, amelioration or delay of progression of a disease or disorder requiring inhibition of PCSK9.

Embodiment 95. Use of a polypeptide according to any one of Embodiments 68-81 and 14-51, or a pharmaceutically acceptable salt thereof, for the treatment, prevention, amelioration or delay of progression of a PCSK9-mediated disease or disorder or for the treatment, prevention, amelioration or delay of progression of a disease or disorder requiring inhibition of PCSK9.

Embodiment 96. Use of a polypeptide according to any one of Embodiments 68-81 and 14-51, or a pharmaceutically acceptable salt thereof, in the manufacture of a medicament for the treatment, prevention, amelioration or delay of progression of a PCSK9-mediated disease or disorder or for the treatment, prevention, amelioration or delay of progression of a disease or disorder requiring inhibition of PCSK9.

Embodiment 97. A method for treating, preventing, ameliorating or delaying the progression of a PCSK9-mediated disease or disorder or of disease or disorder requiring inhibition of PCSK9 or of PCSK9 activity comprising the step of administering to a patient in need thereof a therapeutically effective amount of a polypeptide according to any one of Embodiments 68-81 and 14-51, or a pharmaceutically acceptable salt thereof.

Embodiment 98. The polypeptide for use according to Embodiment 94, the use of a polypeptide according to Embodiment 95 or 96, or the method for according to Embodiment 97, wherein said PCSK9-mediated disease or disorder or the disease or disorder requiring inhibition of PCSK9 is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

In another embodiment, the polypeptides of Formula (I) are enantiomers. In some embodiments the polypeptides are the (S)-enantiomer. In other embodiments, the polypeptides are the (R)-enantiomer. In yet other embodiments, the polypeptides of Formula (I) may be (+) or (−) enantiomers.

In another embodiment, the polypeptides of Formula (I) are diastereomers.

It should be understood that all isomeric forms are included within the disclosure, including mixtures thereof. If the polypeptide contains a double bond, the substituent may be in the E or Z configuration. If the polypeptide contains a disubstituted cycloalkyl, the cycloalkyl substituent may have a cis- or trans configuration. All tautomeric forms are also intended to be included.

Polypeptides of the disclosure, and pharmaceutically acceptable salts, hydrates, solvates, stereoisomers and prodrugs thereof may exist in their tautomeric form (for example, as an amide or imino ether). All such tautomeric forms are contemplated herein as part of the disclosure.

The polypeptides of the disclosure may contain asymmetric or chiral centers, and, therefore, exist in different stereoisomeric forms. It is intended that all stereoisomeric forms of the polypeptides of the disclosure as well as mixtures thereof, including racemic mixtures, form part of the disclosure. In addition, the disclosure embraces all geometric and positional isomers. For example, if a polypeptide of the disclosure incorporates a double bond or a fused ring, both the cis- and trans-forms, as well as mixtures, are embraced within the scope of the disclosure. Each polypeptide herein disclosed includes all the enantiomers that conform to the general structure of the polypeptide. The polypeptides may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the polypeptides of the disclosure may be atropisomers (e.g., substituted biaryls) and are considered as part of this disclosure. Enantiomers can also be separated by use of a chiral HPLC column.

It is also possible that the polypeptides of the disclosure may exist in different tautomeric forms, and all such forms are embraced within the scope of the disclosure. Also, for example, all keto-enol and imine-enamine forms of the polypeptides are included in the disclosure.

All stereoisomers (for example, geometric isomers, optical isomers and the like) of the present polypeptides (including those of the salts, solvates, esters and prodrugs of the polypeptides as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a polypeptide of Formula (I) incorporates a double bond or a fused ring, both the cis- and trans-forms, as well as mixtures, are embraced within the scope of the disclosure. Also, for example, all keto-enol and imine-enamine forms of the polypeptides are included in the disclosure.) Individual stereoisomers of the polypeptides of the disclosure may, for example, be substantially free of other isomers, or may be admixed, for example, as racemates or with all other, or other selected, stereoisomers. The chiral centers of the disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive polypeptides.

The polypeptides of Formula (I) may form salts which are also within the scope of this disclosure. Reference to a polypeptide of the Formula herein is understood to include reference to salts thereof, unless otherwise indicated.

The disclosure relates to polypeptides which are modulators of PCSK9. In one embodiment, the polypeptides of the disclosure are inhibitors of PCSK9.

The disclosure is directed to polypeptides as described herein and pharmaceutically acceptable salts, hydrates, solvates, prodrugs, stereoisomers, or tautomers thereof, and pharmaceutical compositions comprising one or more polypeptides as described herein, or pharmaceutically acceptable salts, hydrates, solvates, prodrugs, stereoisomers, or tautomers thereof.

Activity of the Polypeptides

The activity of cyclic polypeptides according to the disclosure as PCSK9 can be assessed using a time resolved fluorescence resonance energy transfer (TR-FRET) assay. This time resolved fluorescence resonance energy transfer (TR-FRET) assay measures the ability of a cyclic polypeptides of the disclosure to interfere with the binding of human PCSK9 to human LDLR, providing measures of both potency (IC50) and efficacy (Amax).

Solutions of varying concentrations are prepared by diluting a cyclic polypeptide of the disclosure in dimethylsulfoxide (DMSO) and the resulting solutions are pipetted into a plate. DMSO is used as a negative control. An intermediate plate is prepared in by transferring a known amount of each polypeptide solution and of the control from the compound plate into a corresponding well containing assay buffer and mixing thoroughly. A third plate is then prepared to be used for the assay by adding Human PCSK9 Alexa Fluor 647, followed by a known amount of each solution from the intermediate plate. Unlabeled human PCSK9 in assay buffer containing DMSO is used as a positive control for the assay. Following incubation, Human LDLR extracellular domain-Europium Kryptate is added to each well of the assay plate and the resulting mixture is incubated for an additional period of time. The TR-FRET signal is measured and the FRET ratio (FRET/Europium) is used to calculate the $IC_{50}$ and Amax of the cyclic polypeptides.

Method of Synthesizing the Polypeptides

The polypeptides of the disclosure may be made by a variety of methods, including standard chemistry. Suitable synthetic routes are depicted in the Schemes given below.

All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed.

The peptides and polypeptides of the disclosure can be produced by the per se known procedures for peptide synthesis. The methods for peptide synthesis may be any of a solid-phase synthesis and a liquid-phase synthesis. Thus, the peptide and polypeptide of interest can be produced by condensing a partial peptide or amino acid capable of constituting the protein with the residual part thereof and, when the product has a protective group, the protective group is detached whereupon a desired peptide can be manufactured. The known methods for condensation and deprotection include the procedures described in the following literature (1)-(5): (1) M. Bodanszky and M. A. Ondetti, Peptide Synthesis, Interscience Publishers, New York, 1966, (2) Schroeder and Luebke, The Peptide, Academic Press, New York, 1965, (3) Nobuo Izumiya et al., Fundamentals and Experiments in Peptide Synthesis, Maruzen, 1975, (4) Haruaki Yajima and Shumpei Sakakibara, Biochemical Experiment Series 1, Protein Chemistry IV, 205, 1977, and (5) Haruaki Yajima (ed.), Development of Drugs-Continued, 14, Peptide Synthesis, Hirokawa Shoten.

After the reaction, the peptide can be purified and isolated by a combination of conventional purification techniques such as solvent extraction, column chromatography, liquid chromatography, and recrystallization. Where the peptide isolated as above is a free polypeptide, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenz-hydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc-aminomethyl)phenoxy resin, 2-chlorotrityl chloride resin, and so on. Using such a resin, amino acids whose α-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed and if necessary, disulfide bonds are formed to obtain the objective polypeptide.

For the condensation of the above-mentioned protected amino acids, a variety of activating reagents for peptide synthesis can be used such as HATU, HCTU or e.g., a carbodiimide. The carbodiimide includes DCC (N,N'-Dicyclohexylcarbodiimide), N,N'-diisopropylcarbodiimide, and N-ethyl-N'-(3-dimethylaminopropyl)carbodiimide. For activation with such a reagent, a racemization inhibitor additive, e.g., HOBt or Oxyma Pure can be used. The protected amino acid can be directly added to the resin along with the activation reagents and racemization inhibitor or be pre-activated as symmetric acid anhydride, HOBt (Hydroxybenzotriazole) ester, or HOOBt ester then added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned. The reaction temperature can be selected from the range hitherto-known to be useful for peptide bond formation and is usually selected from the range of about −20° C. to about 85° C. The activated amino acid derivative is generally used in a proportion of about 1.5 fold to about 6 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-methoxybenzyloxycarbonyl, Cl—Z, Br—Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned ($C_1$-$C_6$) alkyl, ($C_3$-$C_8$) cycloalkyl and ($C_6$-$C_{10}$)aryl-($C_1$-$C_2$) alkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g., acetyl etc., aroyl groups, e.g., benzoyl, etc., benzyloxycarbonyl, and ethoxycarbonyl. The group suited for said etherification includes benzyl, tetrahydropyranyl, and tertiary-butyl. The protective group for the phenolic hydroxyl group of tyrosine includes Bzl or Z (carboxybenzyl), $Cl_2$-Bzl, 2-nitrobenzyl, Br—Z, and tertiary-butyl.

The protecting group of imidazole for histidine includes Tos or Ts (Tosyl), 4-methoxy-2,3,6-tri ethylbenzenesulfonyl, DNP (2,4-dinitrophenol), benzyloxymethyl, Bum (t-butyloxymethyl), Boc (tert-butyloxy carbonyl), Trt (triphenylmethane), and Fmoc (fluorenylmethyloxycarbonyl).

The activated carboxyl group of the starting amino acid includes the corresponding acid anhydride, azide, and active esters, e.g., esters with alcohols such as pentachlorophenol, 2,4,5-trichlorophenol, 2,4-dinitrophenol, cyanomethyl alcohol, p-nitrophenol, HOBn, N-hydroxysuccinimide, N-hydroxyphthalimide, HOBt (Hydroxybenzotriazole), etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of −20° C.-40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

The polypeptides of Formula (I) may also be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the polypeptide synthesis using methods that are readily apparent to those skilled in the art. The selection processes, as well as the reaction conditions and order of their execution, shall be consistent with the preparation of polypeptides of Formula (I).

Those skilled in the art will recognize if a stereocenter exists in the polypeptides of Formula (I). Accordingly, the disclosure includes both possible stereoisomers (unless specified in the synthesis) and includes not only racemic polypeptides but the individual enantiomers and/or diastereomers as well. When a polypeptide is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The polypeptides described herein may be made from commercially available starting materials or synthesized using known organic, inorganic, and/or enzymatic processes.

Preparation of Polypeptides

The polypeptides of the disclosure can be prepared in a number of ways well known to those skilled in the art of organic synthesis. By way of example, polypeptides of the disclosure can be synthesized using the methods described below, together with synthetic methods known in the art of synthetic organic chemistry, or variations thereof as appreciated by those skilled in the art. Preferred methods include but are not limited to those methods described below. Polypeptides of the disclosure can be synthesized by following the steps outlined in General Scheme 1 which comprise different sequences of assembling intermediates I-a, I-b, I-c, I-d, and I-e. Starting materials are either commercially available or made by known procedures in the reported literature or as illustrated.

General Scheme 1

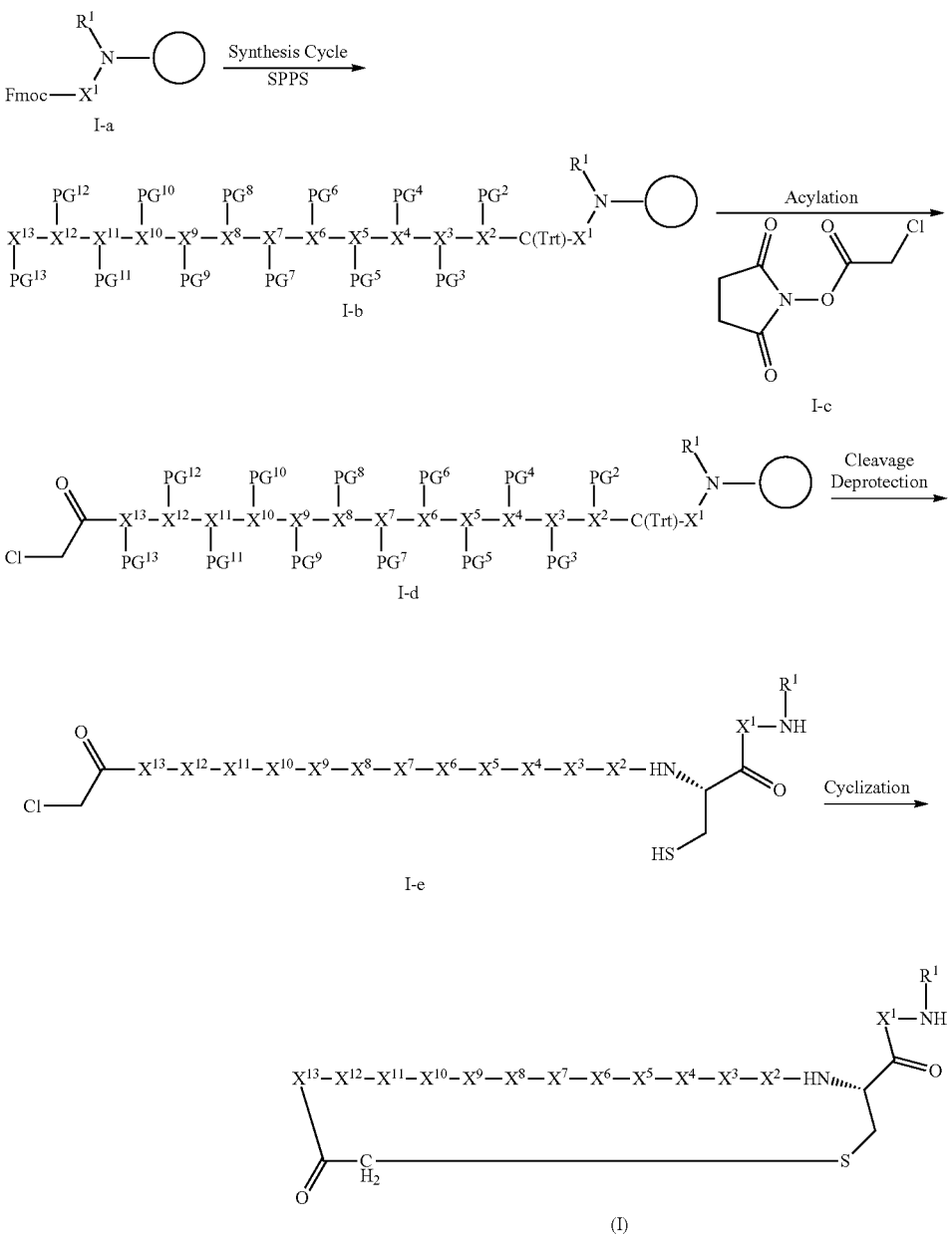

wherein $R^1$, $X^1$, $X^2$, $X^3$ $X^4$, $X^5$, $X^6$, $X^7$, $X^3$ $X^9$, $X^{10}$, $X^{11}$, $X^{12}$, and $X^{13}$ are as defined in Formula (I). PG2, PG3, PG4, PG5, PG6, PG7, PG8, PG9, PG10, PG11, PG12, and PG13 are selected from absent, tert-Butyloxycarbonyl (Boc), 2,2,4,6,7-Pentamethyldihydrobenzofuran-5-sulfonyl (Pbf), or tertbutyl (tBu), respectively.

The general way of preparing polypeptides of Formula (I) by using intermediates I-a, I-b, I-c, I-d, and I-e is outlined in General Scheme 1. Synthesis of intermediate I-b can be accomplished by coupling of an acid with an amine under standard coupling conditions using an amide coupling reagent (e.g., O-(1H-6-chlorobenzotriazole-1-yl)-1,1,3,3-tetramethyluronium hexafluorophosphate (HCTU), O-(7-azobenzotriazol-1-yl)-1,1,3,3-tetramethyluroniumhexafluorophosphate (HATU), or Oxyma Pure® (Ethyl cyano(hydroxyimino)acetate)) and optionally a base (e.g., triethylamine or N,N-diisopropylethylamine (DIPEA)) in a solvent (e.g., dichloromethane (DCM) or dimethylformamide (DMF)) on a resin (e.g., TentaGel™ S RAM resin) optionally at elevated temperature. Solid phase peptide synthesis is a well-established methodology (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). For example, resin I-a can be washed with DMF and then deprotected by treatment with 4-methylpiperidine/DMF. Coupling of a protected amino acid to the deprotected amine I-a can be accomplished under standard coupling conditions as described above. The deprotection and coupling steps are repeated to provide intermediate I-b.

Acylation of I-b with N-succinimidyl 2-chloroacetate I-c in a solvent (e.g., N-methyl-2-pyrrolidone (NMP)) provides I-d. Concomitant removal of the protecting groups and cleavage from the resin using an appropriate reagent, e.g., TFA, phenol, $H_2O$, thioanisole, and/or EDT (Reagent K) provides I-e. (See, D. S. King, C. G. Fields, G. B. Fields, Int. J. Peptide Protein Res. 36, 1990, 255-266) Cyclization of I-e using a base (e.g., triethylamine (TEA)) in a solvent (e.g., dimethylsulfoxide (DMSO)) provides the desired polypeptide of Formula (I).

It should be understood that in the description and formula shown above, the various groups $R^1$, $X^1$, $X^2$, $X^3$ $X^4$, $X^5$, $X^6$, $X^7$, $X^8$ $X^9$, $X^{10}$, $X^{11}$, $X^{12}$, and $X^{13}$, and other variables are as defined above, except where otherwise indicated. Furthermore, for synthetic purposes, the polypeptides of General Scheme 1 are mere representative polypeptides with elected radicals to illustrate the general synthetic methodology of the polypeptides of Formula (I) as defined herein.

Methods of Using the Disclosed Polypeptides

Another aspect of the disclosure is directed to a method of modulating PCSK9. The method comprises administering to a patient in need thereof an effective amount of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier.

In another aspect, the disclosure is directed to a method of inhibiting PCSK9. The method involves administering to a patient in need thereof an effective amount of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier.

Another aspect of the disclosure relates to a method of treating, preventing, inhibiting, or eliminating a disease or disorder in which PCSK9 plays a role. The method comprises administering to a patient in need of a treatment for diseases or disorders in which PCSK9 plays a role an effective amount of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier.

Another aspect of the disclosure relates to a method of treating, preventing, inhibiting, or eliminating a disease or disorder in a patient associated with the inhibition of PCSK9, the method comprising administering to a patient in need thereof an effective amount of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier.

In another aspect, the disclosure relates to a method of treating, preventing, inhibiting, or eliminating a PCSK9-mediated disease or disorder. The method comprises administering to a patient in need of a treatment for a PCSK9-mediated disease or disorder an effective amount of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier.

Another aspect of the disclosure relates to a method of treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides. The method comprises administering to a patient in need of a treatment an effective amount of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier.

In another aspect, the disclosure relates to a method of reducing Lp(a), reducing Lp(a) plasma levels, reducing Lp(a) serum levels, reducing serum TRL or LDL levels, reducing serum triglyceride levels, reducing LDL-C, reducing total plasma apoB concentrations, reducing LDL apoB, reducing TRL apoB, or reducing non HDL-C. The method comprises administering to a patient in need thereof an effective amount of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier.

In another aspect, the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the treatment, prevention, inhibition, or elimination of a disease or disorder in which PCSK9 plays a role.

Another aspect of the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the treatment, prevention, inhibition, or elimination of a disease associated with inhibiting PCSK9.

Another aspect of the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the treatment, prevention, inhibition, or elimination of hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides.

In another aspect, the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the reduction of Lp(a), in the reduction of Lp(a) plasma levels, in the reduction of Lp(a) serum levels, in the reduction of serum TRL or LDL levels, in the reduction of serum triglyceride levels, in the reduction of LDL apoB, in the reduction of TRL apoB, or in the reduction of non HDL-C.

Another aspect of the disclosure relates to the use of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for treating, preventing, inhibiting, or eliminating a disease or disorder in which PCSK9 plays a role.

In another aspect, the disclosure relates to the use of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier in the manufacture of a medicament for inhibiting PCSK9.

In another aspect, the disclosure relates to the use of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier in the manufacture of a medicament for treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides.

Another aspect of the disclosure relates to the use of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier in the manufacture of a medicament for reducing Lp(a), reducing Lp(a) plasma levels, reducing Lp(a) serum levels, reducing serum TRL or LDL levels, reducing serum triglyceride levels, reducing LDL apoB, reducing TRL apoB, or reducing non HDL-C.

In another aspect, the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the manufacture of a medicament for treating a disease associated with inhibiting PCSK9.

Another aspect of the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the manufacture of a medicament for treating a disease in which PCSK9 plays a role.

In another aspect, the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the manufacture of a medicament for treating, preventing, inhibiting, or eliminating hypercholesterolemia, hyperlipidemia, hypertriglyceridemia, sitosterolemia, atherosclerosis, arteriosclerosis, coronary heart disease, peripheral vascular disease, vascular inflammation, xanthoma, peripheral arterial disease, sepsis, elevated Lp(a), elevated LDL, elevated TRL, or elevated triglycerides.

Another aspect of the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the manufacture of a medicament for reducing Lp(a), reducing Lp(a) plasma levels, reducing Lp(a) serum levels, reducing serum TRL or LDL levels, reducing serum triglyceride levels, reducing LDL apoB, reducing TRL apoB, or reducing non HDL-C.

In another aspect, the disclosure relates to the use of an inhibitor of PCSK9 for the preparation of a medicament used in the treatment, prevention, inhibition or elimination of hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, or xanthoma.

Another aspect of the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the treatment of a PCSK9-mediated disease or disorder.

Another aspect of the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the treatment of a PCSK9-mediated disease or disorder which is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

In another aspect, the disclosure relates to the use of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier in the manufacture of a medicament for treating a PCSK9-mediated disease or disorder.

Another aspect of the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use in the manufacture of a medicament for treating a PCSK9-mediated disease or disorder.

In another aspect, the disclosure relates to the use of a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, and a pharmaceutically acceptable carrier for use as a medicament.

The disclosure also relates to the use of an inhibitor of PCSK9 for the preparation of a medicament used in the treatment, prevention, inhibition, or elimination of a disease or condition in which PCSK9 plays a role, wherein the medicament comprises a cyclic polypeptide of Formula (I).

In another aspect, the disclosure relates to a method for the manufacture of a medicament for treating, preventing, inhibiting, or eliminating a disease or condition mediated by PCSK9, wherein the medicament comprises a cyclic polypeptide of Formula (I), or a pharmaceutically acceptable salt, hydrate, solvate, stereoisomer, or tautomer.

In some embodiments of the methods above, the PCSK9-mediated disease or disorder, the disease or disorder in which PCSK9 plays a role, the disease or disorder in a patient associated with the inhibition of PCSK9, and the disease associated with inhibiting PCSK9 is selected from hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

The polypeptides of the disclosure find use in reducing or lowering low density lipoprotein cholesterol (LDL-C) in an individual in need thereof. The individual may have persistently elevated levels of LDL-C. In some embodiments, the individual has LDL-C plasma levels consistently above 70 mg/dL, for example above 80, 90, 100, 110, 120, 130, 140, 150, 160, 170, 180, 190 mg/dL, or higher. The polypeptides of the disclosure may also be used to reduce or lower non-high density lipoprotein cholesterol (non-HDL-C) or total cholesterol in an individual in need thereof.

The disclosure also related to methods for improving blood cholesterol markers associated with increased risk of heart disease. These markers include high total cholesterol, high LDL, high total cholesterol to HDL ratio and high LDL to HDL ratio. A total cholesterol of less than 200 mg/dL is considered desirable, 200-239 mg/dL is considered borderline high and 240 mg/dL and above is considered high.

In a further aspect, the disclosure provides methods of reducing LDL-C, non-HDL-C and/or total cholesterol in an individual in need thereof, the method comprising administering a therapeutically effective amount to the individual a polypeptide as described herein.

In another embodiment, the disclosure relates to a cyclic polypeptide of Formula (I), or a pharmaceutically acceptable salt, hydrate, solvate, stereoisomer, or tautomer thereof, or a pharmaceutical composition comprising a cyclic polypeptide of Formula (I), or a pharmaceutically acceptable salt, hydrate, solvate, stereoisomer, or tautomer thereof, of the disclosure and a pharmaceutically acceptable carrier used for the treatment of diseases including, but not limited to, hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma.

In one embodiment, are provided methods of treating a disease or disorder in which PCSK9 plays a role including hypercholesterolemia, hyperlipidemia, hypertriglyceridemia, sitosterolemia, atherosclerosis, arteriosclerosis, coronary heart disease, peripheral vascular disease, peripheral arterial disease, vascular inflammation, elevated Lp(a), elevated LDL, elevated TRL, elevated triglycerides, sepsis, and xanthoma comprising administering to a patient suffering from at least one of said diseases or disorder a cyclic polypeptide of Formula (I).

The disclosed polypeptides can be administered in effective amounts to treat or prevent a disorder and/or prevent the development thereof in subjects.

The disclosed polypeptides can be administered in effective amounts to treat or prevent a disorder and/or prevent the development thereof in subjects.

Administration, Pharmaceutical Compositions, and Dosing of the Disclosed Polypeptides Administration of the disclosed polypeptides can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Another aspect of the disclosure is directed to pharmaceutical compositions comprising a cyclic polypeptide of Formula (I), or a pharmaceutically acceptable salt, hydrate, solvate, stereoisomer, or tautomer thereof, and a pharmaceutically acceptable carrier. The pharmaceutical acceptable carrier may further include an excipient, diluent, or surfactant. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and
  e) absorbents, colorants, flavors and sweeteners.

Liquid, particularly injectable, compositions can, for example, be prepared by dissolution, dispersion, etc. For example, the disclosed polypeptide is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed polypeptides.

The disclosed polypeptides can be also formulated as a suppository that can be prepared from fatty emulsions or suspensions; using polyalkylene glycols such as propylene glycol, as the carrier.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed polypeptide by weight or volume.

The dosage regimen utilizing the disclosed polypeptide is selected in accordance with a variety of factors including type, species, age, weight, sex and medical condition of the patient; the severity of the condition to be treated; the route of administration; the renal or hepatic function of the patient; and the particular disclosed polypeptide employed. A physician or veterinarian of ordinary skill in the art can readily determine and prescribe the effective amount of the drug required to prevent, counter or arrest the progress of the condition.

Effective dosage amounts of the disclosed cyclic polypeptides, of the disclosed pharmaceutical compositions, or of the disclosed combinations, when used for the indicated effects, range from about 0.5 mg to about 5000 mg of the disclosed polypeptide as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed polypeptide, or, in a range of from one amount to another amount in the list of doses. In one embodiment, the compositions are in the form of a tablet that can be scored. The therapeutically effective dosage of a cyclic peptide, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The cyclic polypeptides of the disclosure can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

Combination Therapy

The cyclic polypeptides of the application can be administered in therapeutically effective amounts in a combinational therapy with one or more therapeutic agents (pharmaceutical combinations) or modalities, e.g., non-drug therapies. For example, synergistic effects can occur with other cardiovascular agents, antihypertensive agents, coronary vasodilators, and diuretic substances. Where the polypeptides of the application are administered in conjunction with other therapies, dosages of the co-administered polypeptides will of course vary depending on the type of co-drug employed, on the specific drug employed, on the condition being treated and so forth.

The cyclic polypeptides of the disclosure may be administered either simultaneously with, or before or after, one or more other therapeutic agent. The cyclic polypeptide of the disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a cyclic polypeptide of the disclosure.

In one embodiment, the disclosure provides a product comprising a cyclic polypeptide of the disclosure and at least one other therapeutic agent as a combined preparation for simultaneous, separate or sequential use in therapy. In one embodiment, the therapy is the treatment of a disease or condition mediated by PCSK9. Products provided as a combined preparation include a composition comprising the cyclic polypeptide of the disclosure and the other therapeutic agent(s) together in the same pharmaceutical composition, or the cyclic polypeptide of the disclosure and the other therapeutic agent(s) in separate form, e.g. in the form of a kit.

In another aspect, the disclosure includes a cyclic polypeptide of Formula (I), Formula (II), Formula (III), Formula (IV), Formula (V), Formula (VI), or a polypeptide according to any one of embodiment No. 1 to No. 50, or any embodiment of Formula (I), Formula (II), Formula (III), Formula (IV), Formula (V), and/or Formula (VI), described herein, or a pharmaceutically acceptable salt thereof, for use in a combination therapy. A composition, medicament and polypeptides for use of Formula (I), Formula (II), Formula (III), Formula (IV), Formula (V), Formula (VI), or a polypeptide according to any one of embodiment No. 1 to No. 50, or any embodiment of Formula (I), Formula (II), Formula (III), Formula (IV), Formula (V), and/or Formula (VI), described herein, or a pharmaceutically acceptable salt thereof, may also be used to advantage in combination with one or more other therapeutic agents.

Another aspect of the disclosure is directed to pharmaceutical compositions comprising a cyclic polypeptide of Formula (I), or a pharmaceutically acceptable salt, hydrate, solvate, stereoisomer, or tautomer thereof, a pharmaceutically acceptable carrier, and one or more therapeutic agents. The pharmaceutical acceptable carrier may further include an excipient, diluent, or surfactant.

Combination therapy includes the administration of the subject polypeptides in further combination with other biologically active ingredients (such as, but not limited to, a second agent such as, but not limited to, a cardiovascular agent, an adrenergic blocker, an antihypertensive agent, an angiotensin system inhibitor, an angiotensin-converting enzyme (ACE) inhibitor, a coronary vasodilator, a diuretic, or an adrenergic stimulant or a second agent that targets PCSK9) and non-drug therapies (such as, but not limited to, surgery or radiation treatment). For instance, the polypeptides of the application can be used in combination with other pharmaceutically active compounds or polypeptides, preferably compounds or polypeptides that are able to enhance the effect of the polypeptides of the application. The polypeptides of the application can be administered simultaneously (as a single preparation or separate preparation) or sequentially to the other drug therapy or treatment modality. In general, a combination therapy envisions administration of two or more drugs during a single cycle or course of therapy.

In some embodiments, polypeptides of the application can be used in combination with agents known to be beneficial for reducing cholesterol, including LDL-C, non-HDL-C, triglyceride-lowering agents, and total cholesterol and/or raising HDL-C.

Exemplary therapeutic agents that may be used in combination with the polypeptides of the disclosure, include, but are not limited to, hypolipidemic agents, niacin and analogs thereof, bile acid sequestrants, a thyroid hormone mimetic, thyroid hormone receptor (THR) β-selective agonist, a microsomal triglyceride transfer protein (MTP) inhibitor, an acyl CoA:diacylglycerol acyltransferase 1 (DGAT1) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, ABCA1 stabilizer or inducer, phospholipid transfer protein (PLTP) inhibitor, fish oil, anti-diabetic agent, anti-obesity agent, agonists of peroxisome proliferator-activator receptors, ATP citrate lyase (ACL) inhibitor, and anti-hypertensive agents.

Examples of hypolipidemic agents that may be used in combination with the polypeptides of the disclosure include, but are not limited to, an HMG-CoA reductase inhibitor, squalene synthase inhibitors, LXR agonist, FXR agonist, fibrates, cholesterol absorption inhibitors, nicotinic acid bile acid binding resins, nicotinic acid and other GPR109 agonists and aspirin.

HMG-CoA reductase inhibitors (i.e., statins) are a class of drugs used to lower cholesterol levels by inhibiting the enzyme HMG-CoA reductase, which plays a central role in the production of cholesterol in the liver. Increased cholesterol levels have been associated with cardiovascular diseases and statins are therefore used in the prevention of these diseases. Exemplary statins include, but are not limited to, atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or pharmaceutically acceptable salts thereof.

Fibrates or fibric acid derivatives lower triglycerides and raise HDL cholesterol. They may have little effect on LDL cholesterol. For example, Gemfibrozil or fenofibrate is prescribed for people who have very high triglycerides or who have low HDL and high triglycerides. Gemfibrozil may be used to reduce the risk of heart attack in people with coronary artery disease (CAD) who have low HDL and high triglycerides. Examples of fibrates include, but are not limited to, clofibrate, gemfibrozil, fenofibrate, ciprofibrate, and bezafibrate.

Cholesterol absorption inhibitors are a class of compounds that prevents the uptake of cholesterol from the small intestine into the circulatory system, and, in turn, reduce plasma LDL-C concentrations. Increased cholesterol levels are associated with increased CVD risk; thus, cholesterol absorption inhibitors are used with the goal of reducing CVD risk. A non-limiting example of a cholesterol absorption inhibitor is Ezetimibe, previously known as "Sch-58235". Another example is Sch-48461. Both compounds are developed by Schering-Plough.

Examples of bile acid sequestrants that may be used in combination with the polypeptides of the disclosure include, but are not limited to, cholestyramine, colestipol, and colesvelam.

A non-limiting example of a thyroid hormone mimetic that may be used in combination with the polypeptides of the disclosure is compound KB2115.

A non-limiting example of a thyroid hormone receptor (THR) β-selective agonist that may be used in combination with the polypeptides of the disclosure is MGL-3196.

DGAT is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1, see Cases et al, Proc. Natl. Acad. Sci. 95:13018-13023, 1998) and DGAT2 (acyl coA-diacylglycerol acyl transferase 2, see Cases et al, J. Biol.

Chem. 276:38870-38876, 2001). DGAT1 and DGAT2 do not share significant protein sequence homology. Importantly, DGAT1 knockout mice are protected from high fat diet-induced weight gain and insulin resistance (Smith et al, Nature Genetics 25:87-90, 2000). The phenotype of the DGAT1 knockout mice suggests that a DGAT1 inhibitor has utility for the treatment of obesity and obesity-associated complications. DGAT1 inhibitors useful in said combination are compounds and analogs generically and specifically disclosed e.g. in WO2007/126957 and WO2009/040410, in particular in the compound claims and the final products of the working examples, the subject-matter of the final products, the pharmaceutical preparations and the claims.

Examples of DGAT1 inhibitors suitable for use in combination with polypeptides of the disclosure, include but are not limited to, {4-[4-(3-Methoxy-5-phenylamino-pyridin-2-yl)-phenyl]-cyclohexyl}-acetic acid, (4-{4-[5-(1-Methyl-1H-pyrazol-3-ylamino)-pyridin-2-yl]-phenyl}-cyclohexyl)-acetic acid, (4-{4-[5-(5-Fluoro-6-methoxy-pyridin-3-ylamino)-pyridin-2-yl]-phenyl}-cyclohexyl)-acetic acid, (4-{5-[5-(6-Trifluoromethyl-pyridin-3-ylamino)-pyridin-2-yl]-spirocyclohexylidenyl-1,1'-indanyl}-acetic acid, (4-{4-[5-(Benzooxazol-2-ylamino)-pyridin-2-yl]-phenyl}-cyclohexyl)-acetic acid, 4-(4-{4-[2-(3-Chlorophenylamino)-oxazol-5-yl]-phenyl}-cyclohexyl)-butyric acid, (4-{4-[5-(6-Trifluoromethyl-pyridin-3-ylamino)-pyridin-2-yl]-phenyl}-cyclohexyl)-acetic acid, (6-{4-[4-(2H-Tetrazol-5-ylmethyl)-cyclohexyl]-phenyl}-pyridazin-3-yl)-(6-trifluoromethyl-pyridin-3-yl)-amine, 3-(4-{4-[6-(6-Trifluoromethyl-pyridin-3-ylamino)-pyridazin-3-yl]-phenyl}-cyclohexylmethyl)-4H-[1,2,4]oxadiazol-5-one, (1-{4-[6-(3-Trifluoromethyl-phenylamino)-pyridazin-3-yl]-phenyl}-piperidin-4-yl)-acetic acid, (4-{4-[4-Methyl-6-(6-trifluoromethyl-pyridin-3-ylamino)-pyridazin-3-yl]-phenyl}-cyclohexyl)-acetic acid, (4-{4-[5-(6-Trifluoromethyl-pyridin-3-ylamino)-pyrazin-2-yl]-phenyl}-cyclohexyl)-acetic acid, 6-[5-(4-Chloro-phenyl)-[1,3,4]oxadiazol-2-yl]-2-(2,6-dichloro-phenyl)-1H-benzoimidazole, 6-(5-Cyclohexyl-[1,3,4]oxadiazol-2-yl)-2-(2,6-dichloro-phenyl)-1H-benzoimidazole, 6-(5-Butyl-[1,3,4]oxadiazol-2-yl)-2-(2,6-dichloro-phenyl)-1H-benzoimidazole, 2-(2,6-Dichloro-phenyl)-6-[5-(5-methyl-pyridin-3-yl)-[1,3,4]oxadiazol-2-yl]-1H-benzoimidazole, 6-[5-(4-Chloro-phenyl)-[1,3,4]oxadiazol-2-yl]-2-(2,6-dimethyl-4-morpholin-4-yl-phenyl)-1H-benzoimidazole, 6-[5-(4-Chloro-phenyl)-[1,3,4]oxadiazol-2-yl]-2-(3,5-dichloro-pyridin-4-yl)-1H-benzoimidazole, 3-(4-{5-[5-(4-Methoxy-phenyl)-[1,3,4]oxadiazol-2-yl]-1H-benzoimidazol-2-yl}-3,5-dimethyl-phenyl)-2,2-dimethyl-propionic acid, 3-(4-{6-[5-(4-Methoxy-phenyl)-[1,3,4]oxadiazol-2-yl]-1H-benzoimidazol-2-yl}-3,5-dimethyl-phenyl)-propionic acid, 3-(4-{6-[5-(4-methoxyphenylamino)-[1,3,4]oxadiazol-2-yl]-1H-benzimidazol-2-yl}-3,5-dimethylphenyl)-propionic acid, [3-(4-{6-[5-(4-Chloro-phenyl)-[1,3,4]oxadiazol-2-yl]-1H-benzoimidazol-2-yl}-3,5-dimethyl-phenyl)-propyl]-phosphonic acid, 2-(2,6-Dichloro-phenyl)-6-(4,5-diphenyl-oxazol-2-yl)-1H-benzoimidazole, (4-{6-[5-(4-Chloro-phenyl)-[1,3,4]oxadiazol-2-yl]-1H-benzoimidazol-2-yl}-3,5-dimethyl-phenoxy)-acetic acid, 2-(2,6-Dichloro-phenyl)-6-(5-pyrrolidin-1-yl-[1,3,4]oxadiazol-2-yl)-1H-benzoimidazole, and 3,5-Dimethyl-4-{6-[5-(4-trifluoromethyl-phenylamino)-[1,3,4]oxadiazol-2-yl]-1H-benzoimidazol-2-yl}-phenol.

A non-limiting example of a Niemann Pick C1-like 1 (NPC1-L1) inhibitor that may be used in combination with the polypeptides of the disclosure is ezetimibe.

Apolipoprotein A-I is a protein that in humans is encoded by the APOA1 gene. It has a specific role in lipid metabolism. Apolipoprotein A-I is the major protein component of high density lipoprotein (HDL) in plasma. Chylomicrons secreted from enterocytes also contain ApoA-I but it is quickly transferred to HDL in the bloodstream. The protein promotes cholesterol efflux from tissues to the liver for excretion. It is a cofactor for lecithin cholesterolacyltransferase (LCAT) which is responsible for the formation of most plasma cholesteryl esters. Infusion of a variant of apoA-I in humans has been shown to regress atherosclerotic plaque, as assessed by intravascular ultrasound; thus, apoA-I reduces CVD risk and has the ability to both slow progression and induce regression of atherosclerosis. A non-limiting example of an apoA-I up-regulator/inducer is RVX208.

ATP-binding cassette transporter, ABCA1 (member 1 of human transporter sub-family ABCA), also known as the cholesterol efflux regulatory protein (CERP) is a protein which in humans is encoded by the ABCA1 gene. This transporter is a major regulator of cellular cholesterol and phospholipid homeostasis. A non-limiting example of an ABCA1 regulator is Probucol. Probucol lowers the level of cholesterol in the bloodstream by increasing the rate of LDL catabolism. Additionally, probucol may inhibit cholesterol synthesis and delay cholesterol absorption. Probucol is a powerful antioxidant which inhibits the oxidation of cholesterol in LDLs; this slows the formation of foam cells, which contribute to atherosclerotic plaques.

The liver X receptor (LXR) is a member of the nuclear receptor family of transcription factors and is closely related to nuclear receptors such as PPAR, FXR and RXR. Liver X receptors (LXRs) are important regulators of cholesterol, fatty acids and glucose homeostasis. LXR agonists are effective for treatment of murine models of atherosclerosis, diabetes, anti-inflammation and Alzheimer's disease. Treatment with LXR agonists (including but not limited to, hypocholamide, T0901317, GW3965, or N,N-dimethyl-3-beta-hydroxy-cholenamide (DMHCA)) lowers the cholesterol level in serum and liver and inhibits the development of atherosclerosis in murine disease models. Examples of LXR agonists include, but are not limited to, GW3965 (a synthetic nonsteroidal liver X receptor (LXR) agonist/activator) and T0901317 (a dual LXR, FXR agonist).

The farnesoid X receptor (FXR), also known as NR1H4 (nuclear receptor subfamily 1, group H, member 4) is a nuclear hormone receptor with activity similar to that seen in other steroid receptors such as estrogen or progesterone but more similar in form to PPAR, LXR and RXR. Activation of the nuclear receptor FXR is known to improve hyperglycemia and hyperlipidemia. A non-limiting example of a FXR agonist is GW4064 (3-(2,6-Dichlorophenyl)-4-(3'-carboxy-2-chlorostilben-4-yl)oxymethyl-5-isopropylisoxazole).

Phospholipid transfer protein (PLTP) is a protein that in humans is encoded by the PLTP gene. The protein encoded by this gene is one of at least two lipid transfer proteins found in human plasma, with CETP being the other. The encoded protein transfers phospholipids from triglyceride-rich lipoproteins to HDL. In addition to regulating the size of HDL particles, this protein may be involved in cholesterol metabolism. At least two transcript variants encoding different isoforms have been found for this gene. Because PLTP influences the metabolism of both triglyceride-rich lipoproteins and HDL, modulation of this transfer protein has the potential to alter cardiovascular disease risk.

Fish oil is derived from the tissues of oily fish. Fish oils contain the omega-3 fatty acids eicosapentaenoic acid (EPA)

and docosahexaenoic acid (DHA), precursors of eicosanoids that are known to have many health benefits. Fish oil and other omega-3 sources are most highly recommended for the following conditions: hypertriglyceridemia, secondary cardiovascular disease and prevention of high blood pressure. For example, Lovaza® is used along with a low-fat and low-cholesterol diet to lower very high triglycerides (fats) in your blood. Examples of omega-3 fatty acids that may be used in combination with the polypeptides of the disclosure include, but are not limited to Lovaza® and Vascepa® (icosapent ethyl).

Examples of anti-diabetic agents that may be used in combination with the polypeptides of the disclosure include, but are not limited to, insulin, insulin derivatives and mimetics; insulin secretagogues such as the sulfonylureas; insulinotropic sulfonylurea receptor ligands such as meglitinides, e.g., nateglinide and repaglinide; protein tyrosine phosphatase-1B (PTP-1B) inhibitors including, but not limited to, PTP-112; GSK3 (glycogen synthase kinase-3) inhibitors including, but not limited to, SB-517955, SB-4195052, SB-216763, NN-57-05441 and NN-57-05445; RXR ligands including, but not limited to, GW-0791 and AGN-194204; sodium-dependent glucose cotransporter inhibitors including, but not limited to, T-1095; glycogen phosphorylase A inhibitors including, but not limited to, BAY R3401; biguanides including, but not limited to, metformin; alpha-glucosidase inhibitors including, but not limited to, acarbose; GLP-1 (glucagon like peptide-1), GLP-1 analogs including, but not limited to, Exendin-4 and GLP-1 mimetics; and DPPIV (dipeptidyl peptidase IV) inhibitors including, but not limited to, vildagliptin.

Examples of sulfonylureas include, but are not limited to, tolbutamide, chlorpropamide, tolazamide, acetohexamide, 4-chloro-N-[(1-pyrolidinylamino)carbonyl]-benzenesulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, amaryl, and tolylcyclamide, or pharmaceutically acceptable salts thereof.

DPP-IV (dipeptidyl peptidase IV) is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. Examples of DPP-IV inhibitors also include, but are not limited to, generically and specifically DPP-IV inhibitors disclosed in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications.

GLP-1 (glucagon like peptide-1) is an insulinotropic protein which is described, e.g., by W. E. Schmidt et al. in *Diabetologia*, 28, 1985, 704-707 and in U.S. Pat. No. 5,705,483. The term "GLP-1 agonists" includes variants and analogs of GLP-1(7-36)NH$_2$ which are disclosed in particular in U.S. Pat. Nos. 5,120,712, 5,118,666, 5,512,549, WO 91/11457 and by C. Orskov, et al, in *J. Biol. Chem.*, 264 (1989) 12826. Further examples include GLP-1(7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig, et al., in *Diabetologia*, 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Examples of anti-obesity agents that may be used in combination with the polypeptides of the disclosure include, but are not limited to, orlistat, sibutramine, phentermine and Cannabinoid Receptor 1 (CB1) antagonists e.g. rimonabant.

Examples of agonists of peroxisome proliferator-activator receptors that may be used in combination with the polypeptides of the disclosure include, but are not limited to, fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

Examples of hypolipidemic agents that may be used in combination with the polypeptides of the disclosure include, but are not limited to, an HMG-CoA reductase inhibitor, squalene synthase inhibitors, LXR agonist, FXR agonist, fibrates, cholesterol absorption inhibitors, nicotinic acid bile acid binding resins, bempedoic acid, nicotinic acid and other GPR109 agonists, and aspirin.

Examples of anti-hypertensive agents that may be used in combination with the polypeptides of the disclosure include, but are not limited to, loop diuretics; angiotensin converting enzyme (ACE); inhibitors of the Na-K-ATPase membrane pump; neutralendopeptidase (NEP) inhibitors; ACE/NEP inhibitors; angiotensin II antagonists; renin inhibitors; β-adrenergic receptor blockers; inotropic agents; calcium channel; aldosterone receptor antagonists; and aldosterone synthase inhibitors.

Examples of loop diuretics that may be used in combination with the polypeptides of the disclosure include, but are not limited to, ethacrynic acid, furosemide and torsemide.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include, but are not limited to, alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, or a pharmaceutically acceptable salt thereof.

A non-limiting example of an inhibitor of the Na-K-ATPase membrane pump is digoxin.

The term "NEP inhibitor" refers to a compound that inhibits neutral endopeptidase (NEP). Examples include, but are not limited to, Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37, and (2R,4s)-5-Biphenyl-4-yl-4-(3-carboxy-propionylamino)-2-methyl-pentanoic acid ethyl ester, or a pharmaceutically acceptable salt thereof. NEP inhibitors also include Phosphono/biaryl substituted dipeptide derivatives, as disclosed in U.S. Pat. No. 5,155,100. NEP inhibitors also include N-mercaptoacyl phenylalanine derivative as disclosed in PCT application WO 2003/104200. NEP inhibitors also include dual-acting anti-hypertensive agents as disclosed in PCT applications WO 2008/133896, WO 2009/035543, or WO 2009/134741. Other examples include compounds disclosed in U.S. application Ser. Nos. 12/788,794; 12/788,766, and 12/947,029. NEP inhibitors also include compounds disclosed in WO 2010/136474, WO 2010/136493, WO 2011/061271, WO 2012/065953, WO 2012/065956, WO 2014/126979, and WO 2014/015965. Other examples of NEP inhibitors are compounds disclosed in WO2015116786, WO2015116760, WO2014138053, WO2014025891, WO2013184934, WO2013067163, WO2012166389, WO2012166387, WO2012112742, and WO2012082853.

The term "ACE/NEP inhibitors" refers to a compound that inhibits both angiotensin converting enzyme (ACE) and neutral endopeptidase (NEP). Examples of ACE/NEP inhibitors that may be used in combination with the polypeptides of the disclosure include, but are not limited to, omapatrilat, sampatrilat, and fasidotril.

The class of angiotensin II antagonists or $AT_1$ receptor antagonists comprises compounds having differing structural features, essentially preferred are the non-peptidic ones. Examples of angiotensin II antagonists that may be used in combination with the polypeptides of the disclosure include, but are not limited to, valsartan, losartan, candesartan, eprosartan, irbesartan, saprisartan, tasosartan, telmisartan, the compounds with the designation E-1477 and ZD-8731 of the following formulae

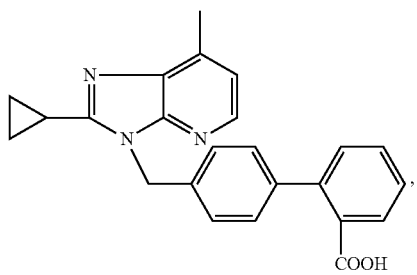

SC-52458

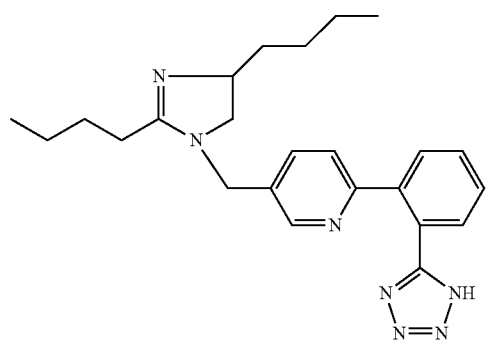

ZD-8731 or, in each case, a pharmaceutically acceptable salt thereof.

The term "renin inhibitor" includes ditekiren (chemical name: [1S-[1R,2R,4R(1R,2R)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2 pyridinylmrthyl)amino]carbonyl]butyl]amino]carbonyl]hexyl]-N-alfa-methyl-L-histidinamide); terlakiren (chemical name: [R-(R,S)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4s,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R[R(R)], 2S,3r]]-N-[1-(cyclohexylmethyl)-2,3-dihydroxy-5-m ethylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

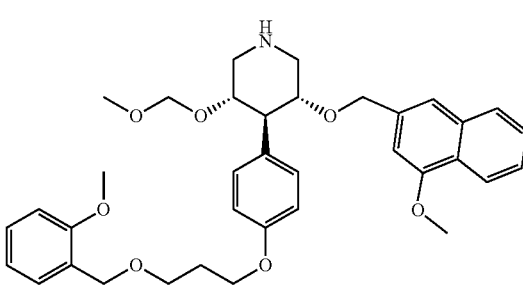

and (B)

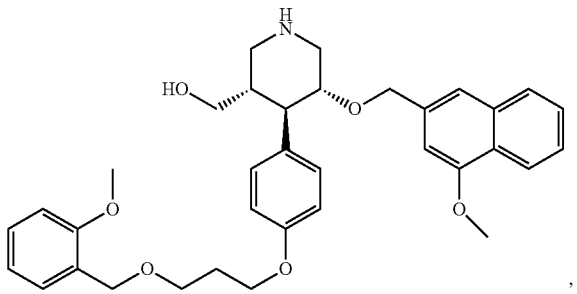

or pharmaceutically acceptable salts thereof. The term "aliskiren", if not defined specifically, is to be understood both as the free base and as a salt thereof, especially a pharmaceutically acceptable salt thereof, most preferably a hemi-fumarate salt thereof.

Examples of β-adrenergic receptor blockers that may be used in combination with the polypeptides of the disclosure include, but are not limited to, acebutolol, atenolol, betaxolol, bisoprolol, metoprolol, nadolol, propranolol, sotalol, and timolol.

Examples of inotropic agents that may be used in combination with the polypeptides of the disclosure include, but are not limited to, digoxin, dobutamine, and milrinone; Inotropes as used herein include, for example, dobutamine, isoproterenol, milrinone, amirinone, levosimendan, epinephrine, norepinephrine, isoproterenol, and digoxin.

Examples of calcium channel blockers that may be used in combination with the polypeptides of the disclosure include, but are not limited to, amlodipine, bepridil, diltiazem, felodipine, nicardipine, nimodipine, nifedipine, nisoldipine and verapamil.

The class of aldosterone synthase inhibitors comprises both steroidal and non-steroidal aldosterone synthase inhibitors, the latter being most preferred. The class of aldosterone synthase inhibitors comprises compounds having differing structural features. Examples of aldosterone synthase inhibitor that can be used in combination with the polypeptides of the disclosure include, but are not limited to, the (+)-enantiomer of the hydrochloride of fadrozole (U.S. Pat. Nos. 4,617,307 and 4,889,861) of formula

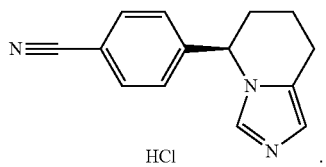 [SMILES: N#Cc1ccc([C@H]2CCCc3cncn32)cc1 ; Cl]

or, if appropriable, a pharmaceutically acceptable salt thereof; and compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Examples of aldosterone synthase inhibitors that can be used in combination with the polypeptides of the disclosure include, but are not limited to, without limitation 4-(6,7-dihydro-5H-pyrrolo[1,2-c]imidazol-5-yl)-3-methyl-benzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluorobenzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include, but are not limited to, compounds and analogs disclosed in WO2008/076860, WO2008/076336, WO2008/076862, WO2008/027284, WO2004/046145, WO2004/014914, and WO2001/076574.

Furthermore, Aldosterone synthase inhibitors also include, but are not limited to, compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the disclosure include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl]-5,6-dihydro-8H-imidazo[5,1-c][1,4]oxazine as developed by Speedel or in each case, the (R) or (S) enantiomer thereof; or if appropriable, a pharmaceutically acceptable salt thereof.

Aldosterone synthase inhibitors useful in said combination include, but are not limited to, compounds and analogs generically and specifically disclosed e.g. in WO 2009/156462 and WO 2010/130796, in particular in the compound claims and the final products of the working examples, the subject-matter of the final products, the pharmaceutical preparations and the claims. Preferred Aldosterone Synthase inhibitors suitable for combination in the disclosure include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl)(cyclopropyl)methyl)ethanesulfonamide, N-(cyclopropyl(5-(1H-indol-5-yl)pyridin-3-yl)methyl)ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

Lipid-lowering agents are known in the art, and described, e.g., in Goodman and *Gilman's The Pharmacological Basis of Therapeutics*, 11th Ed., Brunton, Lazo and Parker, Eds., McGraw-Hill (2006); 2009 *Physicians' Desk Reference* (*PDR*), for example, in the 63rd (2008) Eds., Thomson PDR.

"Combination therapy" is intended to embrace administration of these therapeutic agents in a sequential manner, wherein each therapeutic agent is administered at a different time and in any order, or in alternation and in any order, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

In accordance with the foregoing, the disclosure also provides a therapeutic combination, e.g., a kit, kit of parts, e.g., for use in any method as defined herein, comprising a cyclic polypeptide of Formula (I), or a pharmaceutically acceptable salt thereof, to be used concomitantly or in sequence with at least one pharmaceutical composition comprising at least another therapeutic agent, selected from a hypolipidemic agent, niacin or analogs thereof, a bile acid sequestrant, a thyroid hormone mimetic, a thyroid hormone receptor (THR) β-selective agonist, a microsomal triglyceride transfer protein (MTP) inhibitor, an acyl CoA:diacylglycerol acyltransferase (DGAT) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, an ABCA1 stabilizer or inducer, phospholipid transfer protein (PLTP) inhibitor, fish oil, an antidiabetic agent, an anti-obesity agent, an agonist of peroxisome proliferator-activator receptors, ATP citrate lyase (ACL) inhibitor, and an anti-hypertensive agent, or a pharmaceutically acceptable salt thereof. The kit may comprise instructions for its administration. The combination can be a fixed combination (e.g. in the same pharmaceutical composition) or a free combination (e.g. in separate pharmaceutical compositions).

Similarly, the disclosure provides a kit of parts comprising: (i) a pharmaceutical composition of the disclosure; and (ii) a pharmaceutical composition comprising a compound selected from a hypolipidemic agent, niacin or analogs thereof, a bile acid sequestrant, a thyroid hormone mimetic, a thyroid hormone receptor (THR) β-selective agonist, a microsomal triglyceride transfer protein (MTP) inhibitor, an acyl CoA:diacylglycerol acyltransferase (DGAT) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, an ABCA1 stabilizer or inducer, phospholipid transfer protein (PLTP) inhibitor, fish oil, an antidiabetic agent, an anti-obesity agent, an agonist of peroxisome proliferator-activator receptors, ATP citrate lyase (ACL) inhibitor, and an anti-hypertensive agent, or a pharmaceutically acceptable salt thereof, in the form of two separate units of the components (i) to (ii).

Likewise, the disclosure provides a method as defined above comprising co-administration, e.g., concomitantly or in sequence, of a therapeutically effective amount of a cyclic polypeptide of Formula (I), or a pharmaceutically acceptable salt thereof, and a second drug substance, said second drug substance being a hypolipidemic agent, niacin or analogs thereof, a bile acid sequestrant, a thyroid hormone mimetic, a thyroid hormone receptor (THR) β-selective agonist, a microsomal triglyceride transfer protein (MTP) inhibitor, an acyl CoA:diacylglycerol acyltransferase (DGAT) inhibitor, a Niemann Pick C1-like 1 (NPC1-L1) inhibitor, an agonist of ATP Binding Cassette (ABC) proteins G5 or G8, an inhibitory nucleic acid targeting PCSK9, an inhibitory nucleic acid targeting apoB100, apoA-I up-regulator/inducer, an ABCA1 stabilizer or inducer, phospholipid transfer protein (PLTP) inhibitor, fish oil, an antidiabetic agent, an anti-obesity agent, an agonist of peroxisome proliferator-activator receptors, ATP citrate lyase (ACL) inhibitor, and an anti-hypertensive agent, e.g., as indicated above.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained with a Varian spectrometer at 400 MHz, a Bruker spectrometer at 300 MHz or 400 MHz. Spectra are given in ppm (δ) and coupling constants, J, are reported in Hertz. Tetramethylsilane (TMS) or the solvent peak was used as an internal standard. If not otherwise specified, purity and low resolution mass spectral data were measured using a Thermo Finnigan Surveyor HPLC system with Surveyor photo diode array (PDA) detection and a Thermo LCQ Fleet™ ion trap mass spectrometer. Column: Synergi 4 micron, hydro-RP80A, 30×2.0 mm, Flow rate: 0.500 mL/min; Solvent A (water+0.1% formic acid), Solvent B (acetonitrile+0.1% formic acid); Gradient: 2% B at t=0 to 95% B at 3 min to 95% B at 3.3 min.

General Preparative HPLC Purification Procedure and Mass Spectra

The crude peptides were purified by preparative reverse phase C18-HPLC, using columns of different sizes and with varying flow rates, depending on the amount of crude peptide to be purified. For example, 0.1% TFA in water (A) and 0.1% TFA in acetonitrile (B) were employed as eluents. Product-containing fractions were collected and lyophilized to obtain the purified product.

Condition AA-1 (HRMS)—Column: Acquity UPLC® BEH C18, 130 Å, 1.7 μm 2.1×50 mm, 50° C.; Flow rate: 1.0 mL/min; Mobile phase: (A) 0.1% formic acid+3.75 mM ammonium acetate in water/(B) 0.04% formic+3.75 mM ammonium acetate+5% water in acetonitrile; Gradient: 0.2% to 98% in 7.5 min. Electrospray mass spectra (+), DAD-UV chromatogram 214, 254 nm.

Condition BB-1 (HRMS)—Column: Acquity UPLC® BEH C18, 130 Å, 1.7 μm 2.1×50 mm, 50° C.; Flow rate: 1.0 mL/min; Mobile phase: (A) 0.001% formic acid+2% acetonitrile+3.75 mM ammonium acetate in water/(B) 5% water+3.75 mM ammonium acetate in acetonitrile; Gradient: 2% to 99.9% in 4.4 min; Electrospray mass spectra (+), DAD-UV chromatogram 214, 254 nm.

Condition CC-1 (HRMS)—Column: Acquity UPLC® BEH C18, 130 Å, 1.7 μm 2.1×50 mm, 50° C.; Flow rate: 1.0 mL/min; Mobile phase: (A) 0.1% Formic Acid in water/(B) 0.1% Formic Acid in Acetonitrile; Gradient: 2% to 98% in 1.7 min; Electrospray mass spectra (+), DAD-UV chromatogram 214 nm.

Condition A-1 (LCMS)—Column: Acquity UPLC® BEH C18, 300 Å, 1.7 μm 2.1×50 mm, 80° C.; Flow rate: 1.0 mL/min; Mobile phase: (A) 0.05% TFA in water/(B) 0.04% TFA in acetonitrile; Gradient: 5% to 98% in 4.4 min; Electrospray mass spectra (+), DAD-UV chromatogram 214 nm.

Condition B-1 (LCMS)—Column: Acquity UPLC® HSS T3 100 Å, 1.8 μm 2.1×50 mm, 50° C.; Flow rate: 1.2 mL/min; Mobile phase: (A) 0.05% formic acid+3.75 mM ammonium acetate in water/(B) 0.04% formic acid in acetonitrile; Gradient: 2% to 98% in 1.4 min; Electrospray mass spectra (+), DAD-UV chromatogram 214 nM Condition C-1 (LCMS)—Column: Acquity UPLC® BEH C18, 130 Å, 1.7 μm 2.1×50 mm, 40° C.; Flow rate: 0.7 mL/min; Mobile phase: 5% to 95% in 2.8 min (A) 0.1% formic acid in water/(B) 0.1% formic acid in acetonitrile; Gradient: 5% to 95% in 2.8 min; Electrospray mass spectra (+), DAD-UV chromatogram 214 nm.

Condition D-1 (LCMS)—Column: Acquity UPLC® BEH C18, 300 Å, 1.7 μm 2.1×50 mm, 50° C.; Flow rate: 0.1 mL/min; Mobile phase: (A) 0.05% TFA in water/(B) 0.04% TFA in acetonitrile; Gradient: hold for 2 min 5% B from 5 to 100% B in 11 min; Electrospray mass spectra (+), DAD-UV chromatogram 214 nm.

Condition E-1 (LCMS)—Column: Acquity UPLC® BEH C18, 300 Å, 1.7 μm 2.1×50 mm, 80° C.; Flow rate: 1.0 mL/min; Mobile phase: (A) 0.5% TFA in water/(B) 0.4% TFA in acetonitrile; Gradient: 5% to 98% in 4.4 min; Electrospray mass spectra (+), DAD-UV chromatogram 214 nm.

Condition F-1 (LCMS)—Column: Ascentis Express C18, 2.7 μm 2.1×30 mm, 50° C.; Flow rate: 1.0 mL/min; Mobile phase: (A) 0.05% TFA in water/(B) 0.04% TFA in acetonitrile; Gradient: 5% to 95% in 1.9 m; Electrospray mass spectra (+), DAD-UV chromatogram 212-216 nm.

Condition G-1 (LCMS)—Column: Acquity UPLC® BEH C18, 130 Å, 1.7 μm, 2.1×50 mm, 40° C.; Flow rate: 0.7 mL/min; Mobile phase: (A) 0.1% Formic acid in water/(B) 0.1% Formic acid in acetonitrile; Gradient: 20% to 25% in 1 m, then to 90% in 3.2 mi; Electrospray mass spectra (+), DAD-UV chromatogram 214 nm.

Condition H-1 (LCMS)—Column: Acquity UPLC® BEH C18 300 Å, 1.7 μm 2.1×50 mm, 80° C.; Flow rate: 1.0 mL m; Mobile phase: (A) 0.05% TFA in water; (B) 0.04% TFA in acetonitrile Gradient: 0% to 98% in 4.4 m; Electrospray mass spectra (+), DAD-UV chromatogram 214 nm.

Abbreviations used in the following examples and elsewhere herein are:

AA: amino acid
Ac: acetyl
$Ac_2O$: acetic anhydride
ACN: acetonitrile
aq.: aqueous
AM: aminomethyl
Boc: tert-butoxycarbonyl
BSA: bovine serum albumin
DCM: dichloromethane
DTT: dithiothreitol
DMA: dimethylacetamide
DMF: N,N-dimethylformamide
DMSO: dimethylsulfoxide
DIPEA: N,N-diisopropylethylamine
EDT: ethanedithiol
eq.: equivalent
ESI-MS: electrospray ionization mass spectrometry
Et and EtOAc: ethyl and ethyl acetate
Fmoc: fluorenylmethyloxycarbonyl
FRET: Fluorescence Resonance Energy Transfer
HATU: O-(7-azobenzotriazol-1-yl)-1,1,3,3-tetramethyluroniumhexafluorophosphate
HCTU: O-(1H-6-chlorobenzotriazole-1-yl)-1,1,3,3-tetramethyluronium hexafluorophosphate
HEPES: 4-(2-hydroxyethyl)-1-piperazineethanesulfonic acid
HPLC: high pressure liquid chromatography
h, hr: hour(s)
HRMS: high resolution mass spectrometry
IC50: half maximal inhibitory concentration
LC and LCMS: liquid chromatography and liquid chromatography-mass spectrometry
LDLR: low density lipoprotein receptor
N: equivalent per liter
min: minute(s)
Me: methyl
MS: mass
m/z: mass to charge ratio M and mM: molar and millimolar
mg: milligram
μL, mL and L: microliter(s), milliliter(s) and liter(s)
NMP: N-methyl-2-pyrrolidone
Oxima pure: 2-Cyano-2-(hydroxyimino)acetic acid ethyl ester, potassium salt, Ethyl (hydroxyimino)cyanoacetate potassium salt
PG: protecting group
PyOxim: [Ethyl cyano(hydroxyimino)acetato-O2]tri-1-pyrrolidinylphosphonium hexafluorophosphate
Pbf: 2,2,4,6,7-pentamethyldihydrobenzofuran-5-sulfonyl
PCSK9: Proprotein convertase subtilisin/kexin type 9
Ph: phenyl
RP: reverse phase
rt: room temperature
SPPS: solid phase peptide synthesis
sat.: saturated
TEA: triethylamine
THF: tetrahydrofuran
TentaGel™ S RAM resin: N-Fmoc'-4'-[poly(oxyethylene)carbamoylmethoxy]-2, 4-dimethoxy-benzhydrylamine polymer bound, poly(oxyethylene)-RAM polymer bound
tBu: tertiary butyl
TFA: trifluoroacetic acid
TIS: triisopropylsilane
TR: time resolved
Trt: trityl
UPLC: ultra performance liquid chromatography
UV: ultraviolet
wt: weight General Cyclic Peptide Synthesis Procedure:

Polypeptides of the disclosure can be synthesized by following the steps outlined in general scheme shown below in an analogous manner.

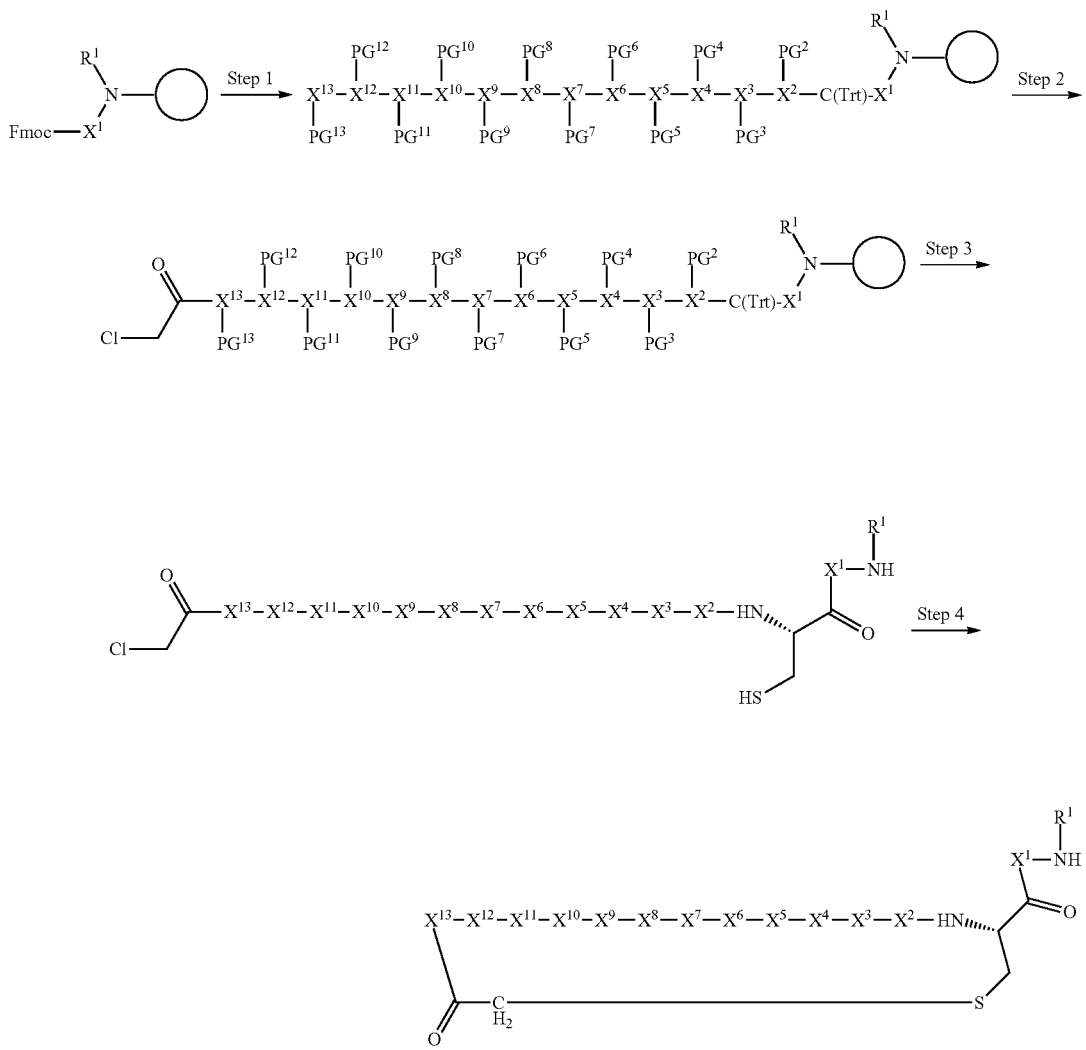

Step 1: Peptide Synthesis

Solid Phase Peptide Synthesis on the Liberty® Peptide Synthesizer from CEM, Inc

Synthesis Cycle A-1

The resin was washed with DMF and then deprotected in two cycles by treatment with 4-methylpiperidine/DMF (1:4)—the first cycle for 30 seconds, and the second cycle for 3 minutes. Coupling was accomplished by addition of the Fmoc-amino acid (4-5 eq.; 0.2 M solution in DMF), HATU (4-5 eq.; 0.5 M solution in DMF) and DIPEA (4-6 eq.; 2 M solution in NMP). The coupling and deprotection steps were repeated until the desired cyclic polypeptide of Formula (I) was obtained. All Fmoc amino acids were coupled for 5 min at 75° C., except for the amino acids shown in Table 3 below. After the final coupling was completed, Fmoc was removed by repetitive treatment with 4-methylpiperidine/DMA (1:4) to provide the deprotected peptide.

TABLE 3

| AA coupling condition for Synthesis Cycle A-1 | | |
|---|---|---|
| AA | Temperature (° C.) | Time (min) |
| Fmoc-N-methyl AA | 75 | 10 |
| Any Fmoc-AA coupled to an N-methyl AA | 75 | 10 |
| Fmoc-C(Trt) | 50 | 10 |

Solid Phase Peptide Synthesis on the Prelude® Peptide Synthesizer from Gyros Protein Technologies AB Alternatively, the peptide was synthesized on the Prelude® Peptide Synthesizer as described in Synthesis Cycle B-1 or in Synthesis Cycle B-2.

Synthesis Cycle B-1

The resin was washed with DMA. Fmoc was then removed by repetitive treatment of the resin with piperidine/DMA (1:4). Coupling was accomplished by addition of the Fmoc-amino acid (3 eq.; 0.2 M solution in NMP), HCTU (3 eq.; 0.3 M solution in NMP), and DIPEA (3-6 eq.; 0.66-0.9 M solution in NMP) followed by mixing of the suspension with nitrogen at rt for typically 15 min to 4 h depending on the specific requirements. After washing with DMA, the coupling step was repeated. After washing with DMA, capping was performed by addition of a mixture of Ac$_2$O/pyridine/DMA (1:1:8) and subsequent mixing of the suspension at rt. After the final coupling was completed, Fmoc was removed as described above in Synthesis Cycle A-1 to provide the peptide.

Synthesis Cycle B-2

The resin was washed with DMA. Fmoc was removed by repetitive treatment with 4-methylpiperidine/DMA (1:4). Coupling was accomplished by addition of a mixture of the Fmoc-amino acid (3 eq.; 0.2 M solution in NMP), Oxyma Pure (3 eq. 0.3 M solution in NMP) and DIPEA (6-7 eq.; 0.66 M solution in NMP) followed by mixing of the suspension with nitrogen at rt for 15 min to 4 h depending on the specific requirements. After washing with DMA, the coupling step was repeated. After washing with DMA capping was performed by addition of a mixture of Ac$_2$O/pyridine/DMA (1:1:8) and subsequent mixing of the suspension at rt. After the final coupling was completed, Fmoc was removed as described above in Synthesis Cycle A-1 to provide the peptide.

Step 2: Peptide Acylation

The resin product obtained from Step 1 was suspended in N-methylpyrrolidine, and N-succinimidyl 2-chloroacetate (5 equivalents) was added. The resulting resin mixture was shaken at room temperature overnight. The resin was then filtered and washed three times each with dimethylformamide and dichloromethane to provide the acylated peptide product.

Step 3: Cleavage from Resin with or without Concomitant Removal of Protecting Groups (PGs)

The resin product obtained from Step 2 was shaken for 1-2 h with one of the cleavage solutions listed herein below (1-5 mL for 0.1 mmol scale). The resin was filtered and treated again with fresh cleavage solution for 0.5-1 h. The cleavage cycle was repeated as needed. The resin was then filtered and the combined filtrates were poured slowly onto a mixture of cold heptane/diethyl ether (1:1) to provide a precipitate. The suspension containing the precipitate was centrifuged and the supernatant was poured off. The precipitate was suspended in cold ether, vortexed briefly, and then centrifuged. This washing process was repeated two more times. The crude peptide product was dried in high vacuum.

The following cleavage solutions were used:
Cleavage Method 1: TFA/H$_2$O/TIS/DTT (92.5:2.5:2.5:2.5)
Cleavage Method 2: 95% aq. TFA/EDT/TIS (95:2.5:2.5)

Step 4: Peptide Cyclization

The crude peptide product obtained from Step 3 was dissolved in DMSO or DMA and treated with TEA or DIPEA. The reaction mixture was then shaken overnight at room temperature. The resulting reaction mixture containing the cyclized peptide was concentrated on a centrifugal evaporator to provide the desired cyclic polypeptide of Formula (I).

Example 1: Synthesis of Ac*-F-V-D-T-T-S-(N-Me)F-B-(N-Me)E-N—S-P-C*-G-NH$_2$ (1-1)

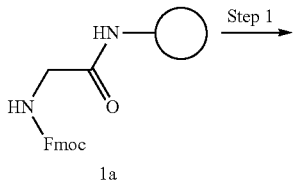

1a

-continued

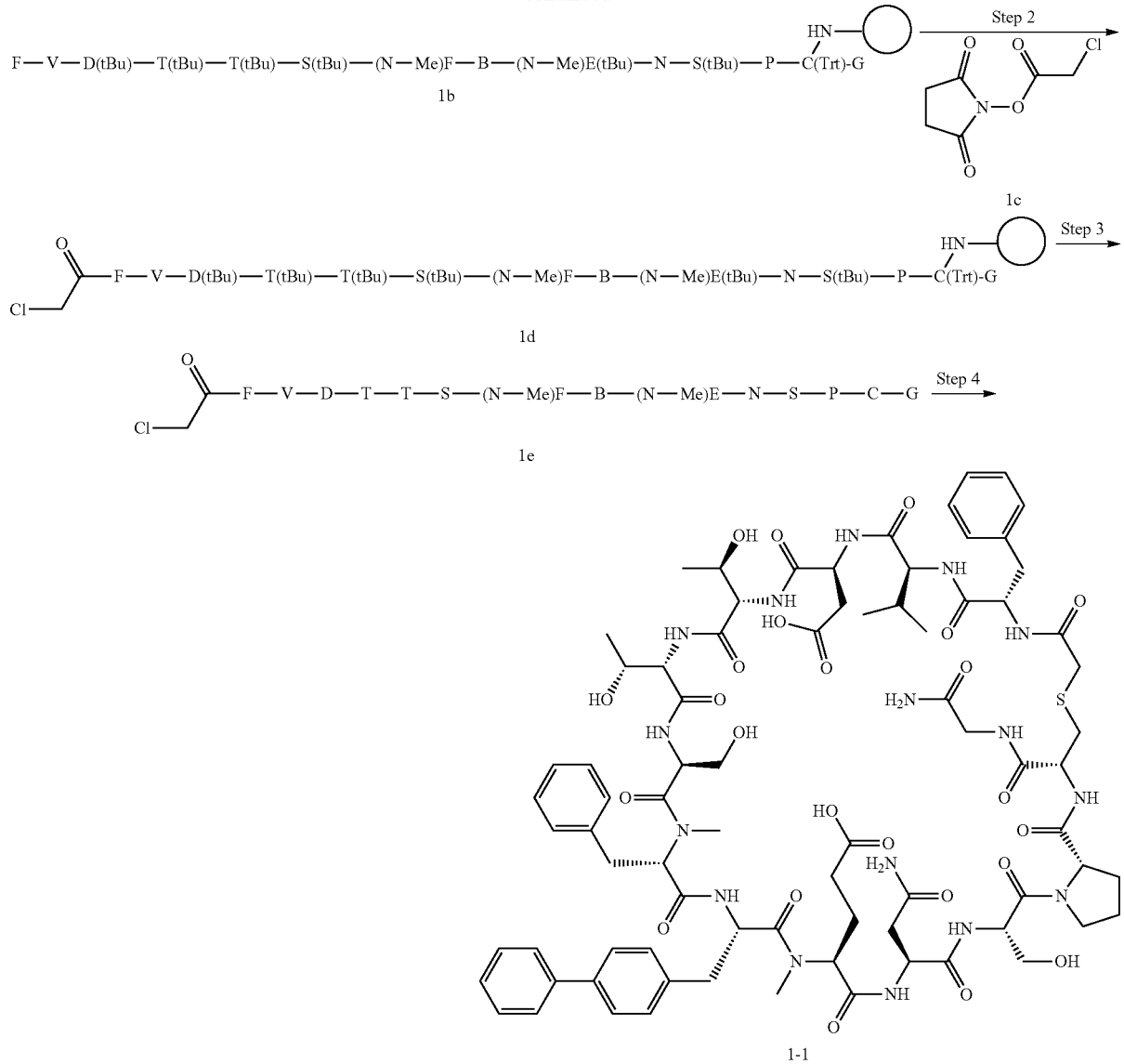

Step 1: F-V-D(tBu)-T(tBu)-T(tBu)-S(tBu)-(N-Me)F-B-(N-Me)E(tBu)-N-S(tBu)-P-C(Trt)-NHresin-G (1b)

The peptide sequence 1b was synthesized on Fmoc-Gly-RAM TentaGel™ Resin (1a, 0.22 mmol/g loading, 0.25 mmol scale) on a Liberty® Peptide Synthesizer following general peptide Synthesis Cycle A-1 (Fmoc-amino acid (4 eq.; 0.2 M solution in DMF), HATU (4 eq.; 0.5 M solution in DMF) and DIPEA (4.4 eq.; 2 M solution in NMP)). The resin was then filtered and washed with DMF (2×) and DCM (3×) to provide the desired product 1b.

Step 2: ClCH$_2$C(O)-F-V-D(tBu)-T(tBu)-T(tBu)-S(tBu)-(N-Me)F-B-(N-Me)E(tBu)-N-S(tBu)-P-C(Trt) resin-G (1d)

A solution of N-succinimidyl 2-chloroacetate (1c, 287 mg, 1.5 mmol) in NMP (8 mL) was added to the peptide resin 1b from Step 1 (0.25 mmol) and the resulting mixture was shaken at room temperature overnight. The resin was then drained, washed with DMF (3×) and DCM (4×), and dried to provide the desired product 1d.

Step 3: ClCH$_2$C(O)-F-V-D-T-T-S-(N-Me)F-B-(N-Me)E-N-S-P-C-G (1e)

The peptide resin product 1d from Step 2 was cleaved from the resin and simultaneously deprotected using Cleavage Method 1 described herein above to provide the crude peptide 1e (266 mg). ESI-MS m/z: 866.6 [M+2H]$^{2+}$.

Step 4: 3-((3R,9S,12S,15S,18S,21S,24S,27S,30S,33S,36S,39S,44aS)-30-([1,1'-biphenyl]-4-ylmethyl)-36-(2-amino-2-oxoethyl)-3-((2-amino-2-oxoethyl)carbamoyl)-9,27-dibenzyl-15-(carboxymethyl)-18,21-bis((R)-1-hydroxyethyl)-24,39-bis(hydroxymethyl)-12-isopropyl-26,32-dimethyl-1,7,10,13,16,19,22,25,28,31,34,37,40-tridecaoxodotetracontahydro-6H-pyrrolo[2,1-f][1]thia[4,7,10,13,16,19,22,25,28,31,34,37,40]tridecaazacyclodotetracontin-33-yl)propanoic acid (1-1)

The crude peptide 1e from Step 3 (266 mg) was dissolved in DMSO (20.5 mL). A few drops of TEA were added to get to pH 8-9. The resulting mixture was stirred at rt overnight. The reaction mixture was then concentrated down to a few mL of DMSO on a centrifugal evaporator. The crude cyclic peptide was purified by preparative HPLC (Sunfire™ Prep 018 Column, 130 Å, 5 µm, 30×50 mm, 15-40% in 6 min, 75 mL/min, ACN in water with 0.1% TFA) and then lyophilized to provide the title polypeptide 1-1 (58 mg, 22%) as a white solid.

The following polypeptides in Table 4 were synthesized according the procedure described in Example 1 for polypeptide (1-1) using the Prelude® peptide synthesizer.

TABLE 4

| Ex. No. | Structure |
|---|---|
| 1-2 | 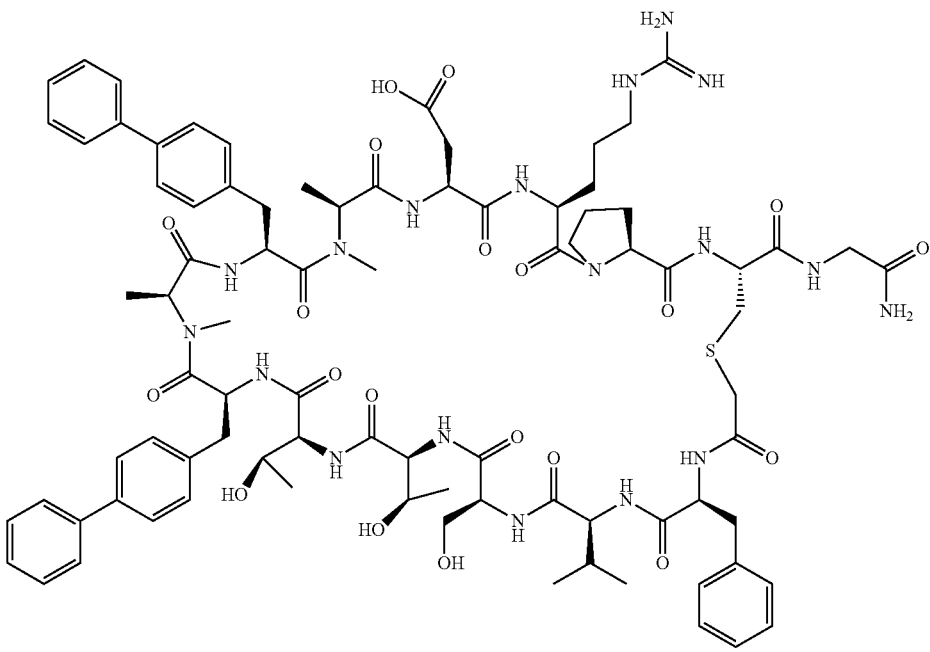 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CCCNC(=N)N)NC(=O)[C@H](CC(=O)O)NC(=O)[C@H](C)N(C)C(=O)[C@H](Cc2ccc(-c3ccccc3)cc2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@H](CO)NC1=O] |
| 1-3 | 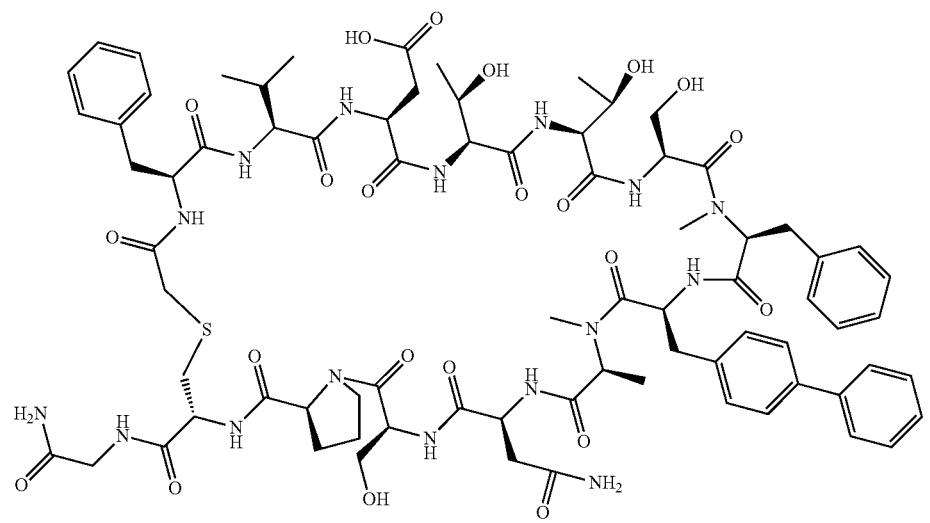 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CC(N)=O)NC(=O)[C@H](C)N(C)C(=O)[C@H](Cc2ccc(-c3ccccc3)cc2)NC(=O)[C@H](Cc2ccccc2)N(C)C(=O)[C@H](CO)NC(=O)[C@H]([C@@H](C)O)NC(=O)[C@H]([C@@H](C)O)NC(=O)[C@H](CC(=O)O)NC1=O] |

US 12,209,144 B2
117                                                                                   118
TABLE 4-continued
| Ex. No. | Structure |
|---|---|
| 1-4 | 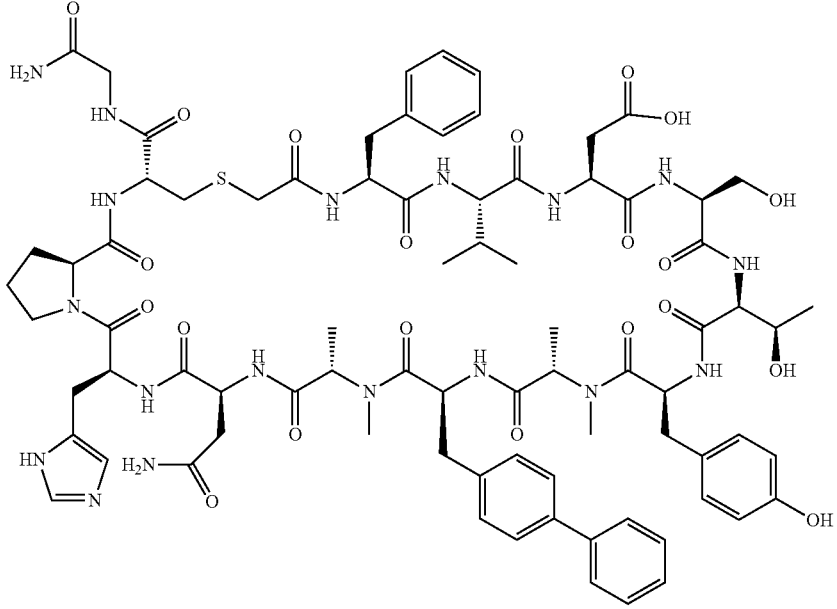 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](Cc2cnc[nH]2)NC(=O)[C@H](CC(N)=O)NC(=O)[C@H](C)N(C)C(=O)[C@H](Cc2ccc(-c3ccccc3)cc2)NC(=O)[C@H](C)N(C)C(=O)[C@H](Cc2ccc(O)cc2)NC(=O)[C@H]([C@@H](C)O)NC(=O)[C@H](CO)NC(=O)[C@H](CC(=O)O)NC1=O] |
| 1-5 | 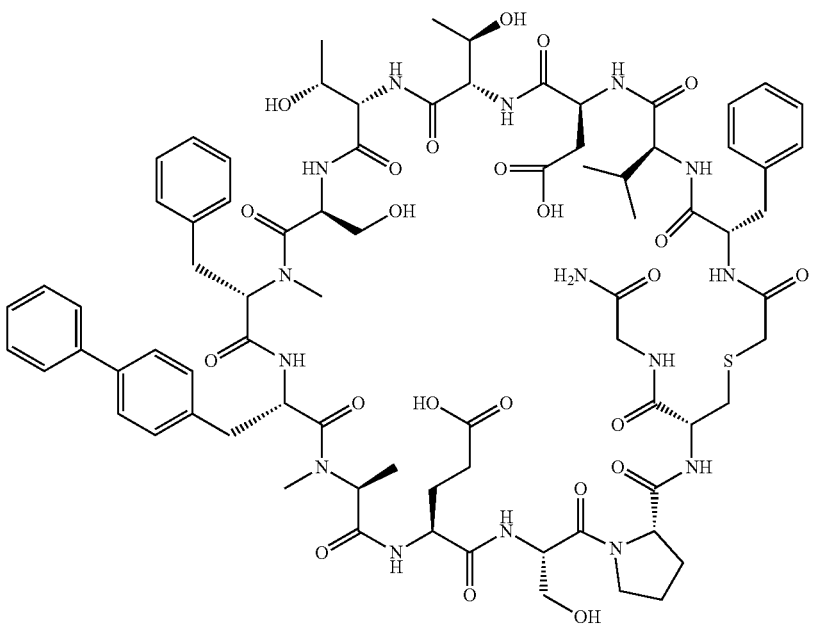 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CCC(=O)O)NC(=O)[C@H](C)N(C)C(=O)[C@H](Cc2ccc(-c3ccccc3)cc2)NC(=O)[C@H](Cc2ccccc2)N(C)C(=O)[C@H](CO)NC(=O)[C@H]([C@@H](C)O)NC(=O)[C@H]([C@@H](C)O)NC(=O)[C@H](CC(=O)O)NC1=O] |

TABLE 4-continued
| Ex. No. | Structure |
|---|---|
| 1-6 | 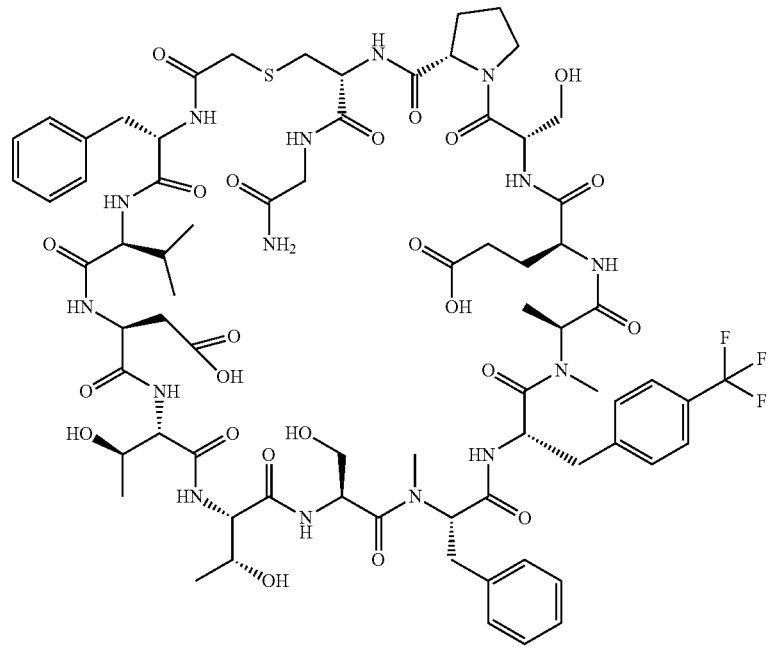 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CCC(=O)O)NC(=O)[C@H](C)N(C)C(=O)[C@H](Cc2ccc(C(F)(F)F)cc2)NC(=O)[C@H](Cc2ccccc2)N(C)C(=O)[C@H](CO)NC(=O)[C@H]([C@@H](C)O)NC(=O)[C@H]([C@@H](C)O)NC(=O)[C@H](CC(=O)O)NC1=O] |
| 1-7 | 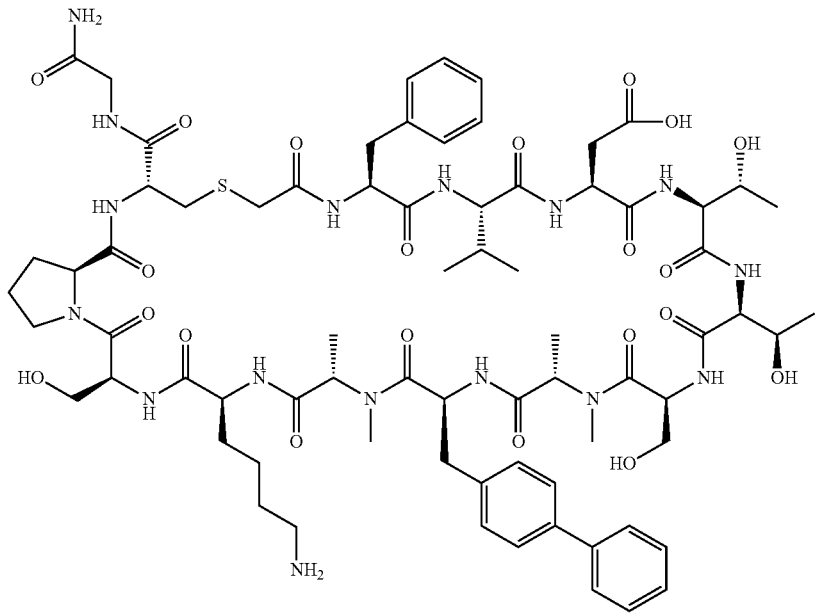 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CCCCN)NC(=O)[C@H](C)N(C)C(=O)[C@H](Cc2ccc(-c3ccccc3)cc2)NC(=O)[C@H](C)N(C)C(=O)[C@H](CO)NC(=O)[C@H]([C@@H](C)O)NC(=O)[C@H]([C@@H](C)O)NC(=O)[C@H](CC(=O)O)NC1=O] |

TABLE 4-continued
| Ex. No. | Structure |
|---|---|
| 1-8 | 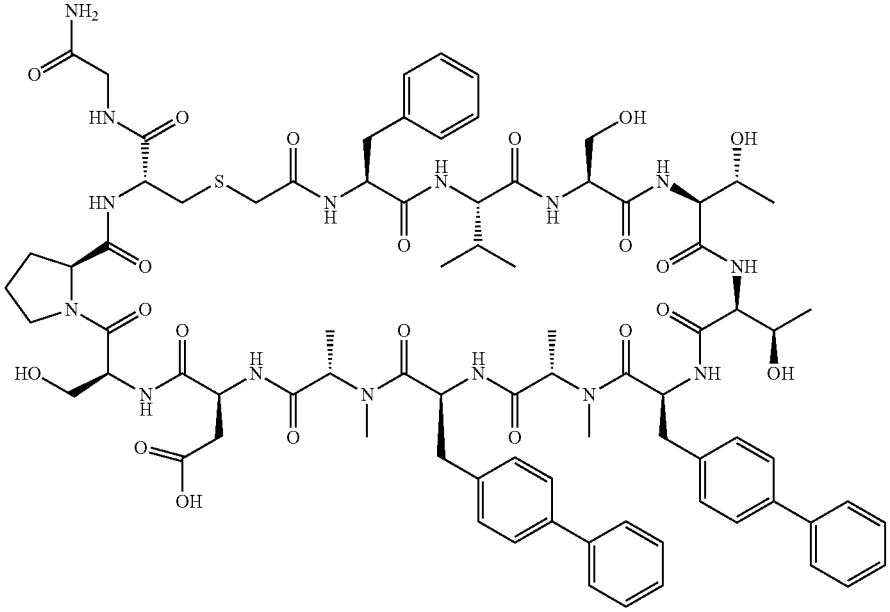 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CC(=O)O)NC(=O)[C@H](C)N(C)C(=O)[C@H](Cc2ccc(-c3ccccc3)cc2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@H](CO)NC1=O] |
| 1-11 | 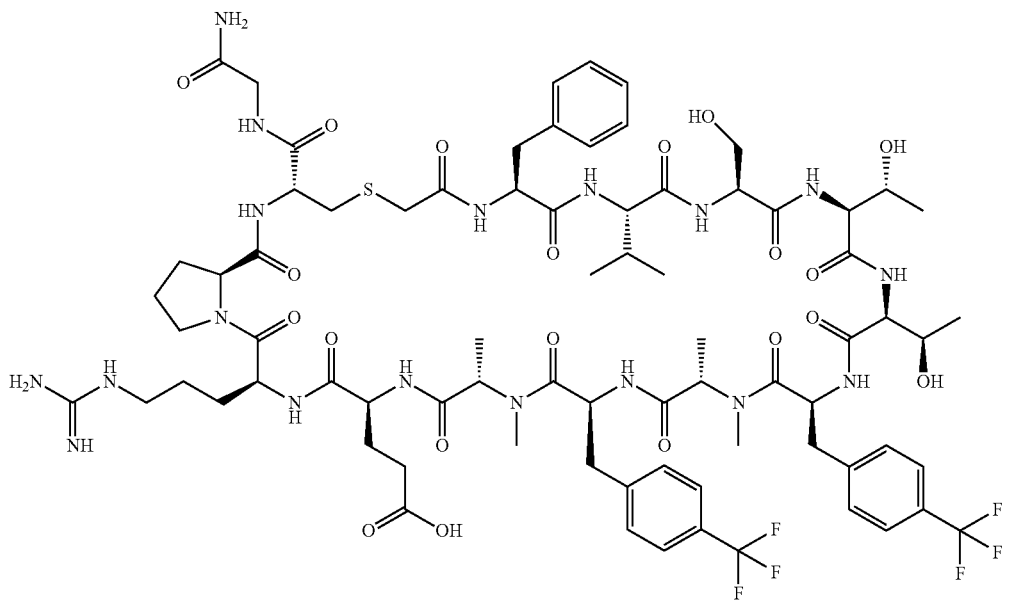 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CCCNC(=N)N)NC(=O)[C@H](CCC(=O)O)NC(=O)[C@H](C)N(C)C(=O)[C@H](Cc2ccc(C(F)(F)F)cc2)NC(=O)[C@H](C)N(C)C(=O)[C@H](Cc2ccc(C(F)(F)F)cc2)NC(=O)[C@H]([C@@H](C)O)NC(=O)[C@H]([C@@H](C)O)NC(=O)[C@H](CO)NC1=O] |

TABLE 4-continued
| Ex. No. | Structure |
|---|---|
| 1-16 | 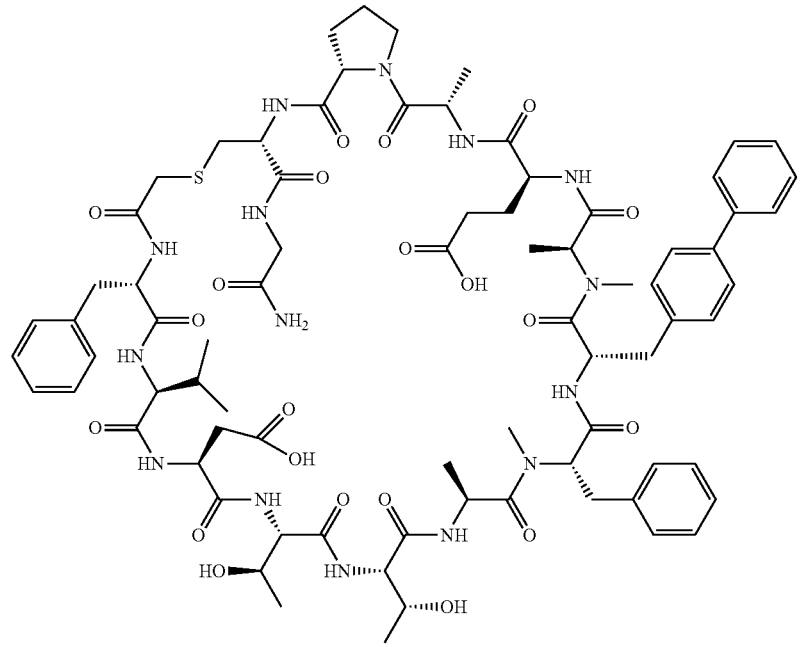 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](C)NC(=O)[C@H](CCC(=O)O)NC(=O)[C@H](C)N(C)C(=O)[C@H](Cc2ccc(-c3ccccc3)cc2)NC(=O)[C@H](Cc2ccccc2)N(C)C(=O)[C@H](C)NC(=O)[C@H]([C@@H](C)O)NC(=O)[C@H]([C@@H](C)O)NC(=O)[C@H](CC(=O)O)NC1=O] |
| 1-17 | 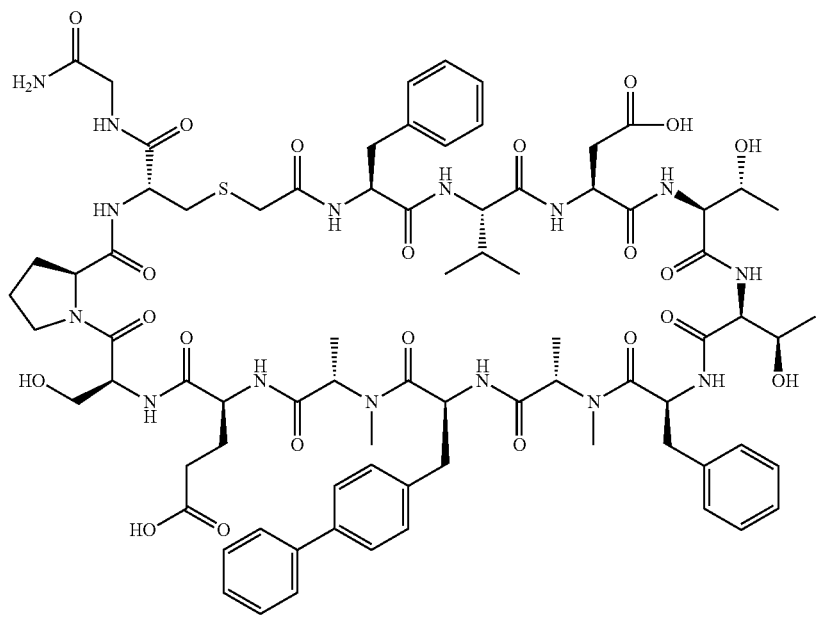 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CCC(=O)O)NC(=O)[C@H](C)N(C)C(=O)[C@H](Cc2ccc(-c3ccccc3)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](CC(=O)O)NC1=O] |

TABLE 4-continued
| Ex. No. | Structure |
|---|---|
| 1-18 | 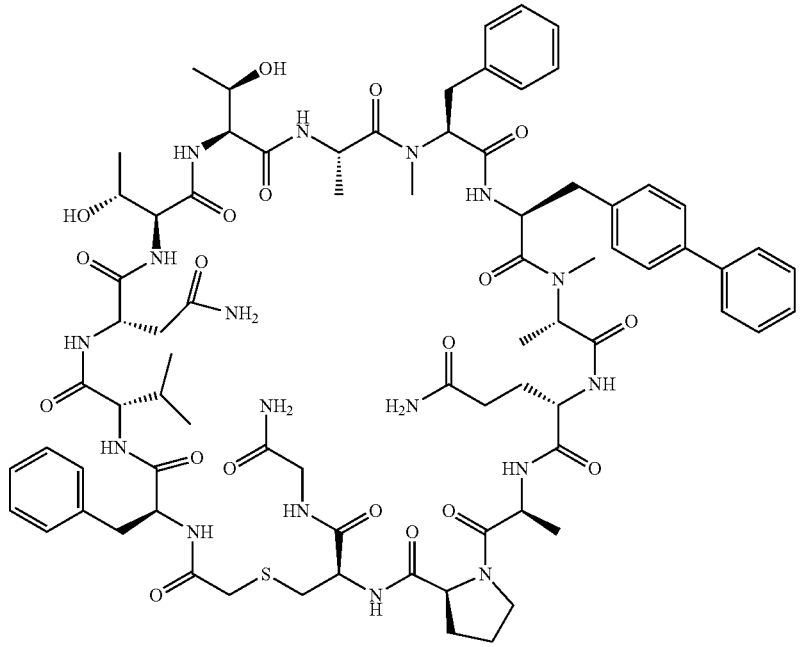 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](C)NC(=O)[C@H](CCC(N)=O)NC(=O)[C@H](C)N(C)C(=O)[C@H](Cc2ccc(-c3ccccc3)cc2)NC(=O)[C@H](Cc2ccccc2)N(C)C(=O)[C@H](C)NC(=O)[C@H]([C@@H](C)O)NC(=O)[C@H]([C@@H](C)O)NC(=O)[C@H](CC(N)=O)NC1=O] |
| 1-21 | 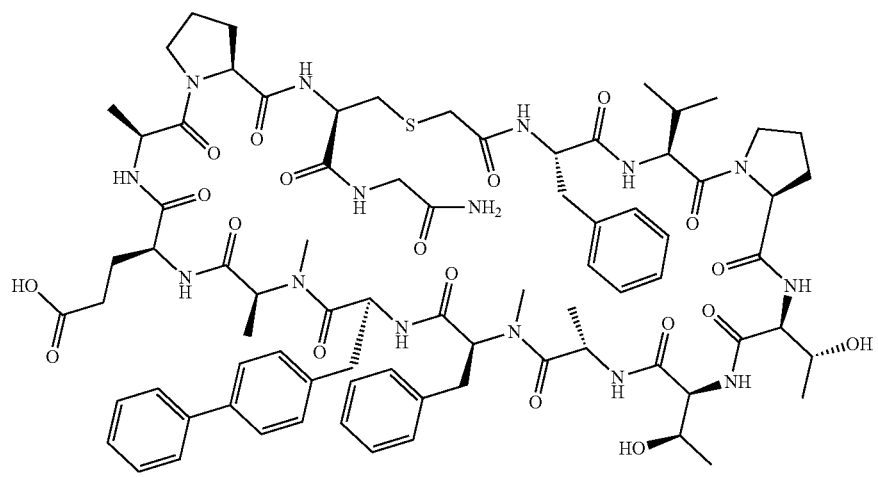 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](C)NC(=O)[C@H](CCC(=O)O)NC(=O)[C@H](C)N(C)C(=O)[C@H](Cc2ccc(-c3ccccc3)cc2)NC(=O)[C@H](Cc2ccccc2)N(C)C(=O)[C@H](C)NC(=O)[C@H]([C@@H](C)O)NC(=O)[C@H]([C@@H](C)O)NC(=O)[C@@H]2CCCN2C1=O] |

TABLE 4-continued
| Ex. No. | Structure |
|---|---|
| 1-22 | 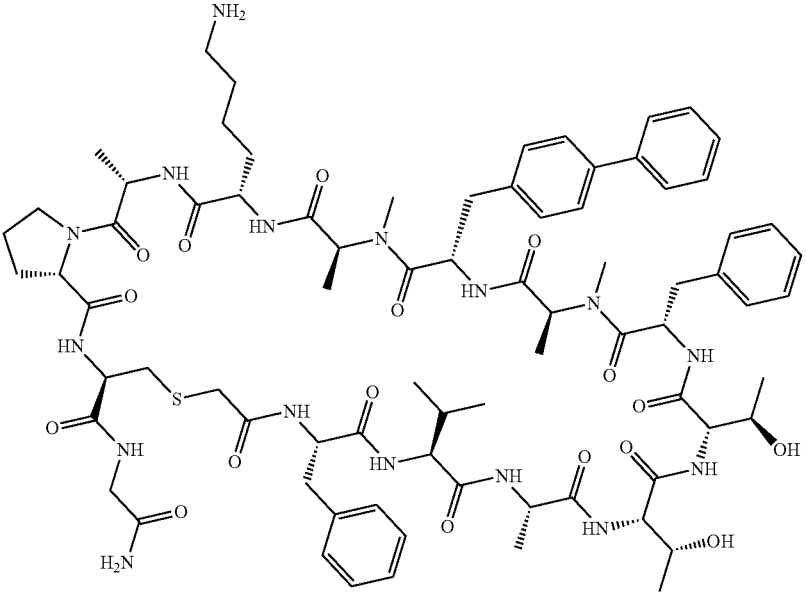 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](C)NC(=O)[C@H](CCCCN)NC(=O)[C@H](C)N(C)C(=O)[C@H](Cc2ccc(-c3ccccc3)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](C)NC1=O] |
| 1-23 | 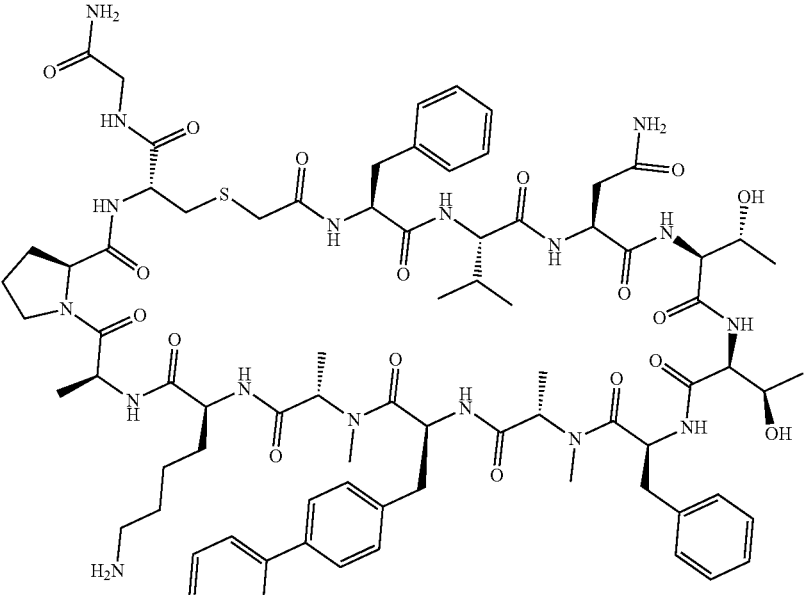 |

TABLE 4-continued
| Ex. No. | Structure |
|---|---|
| 1-27 | 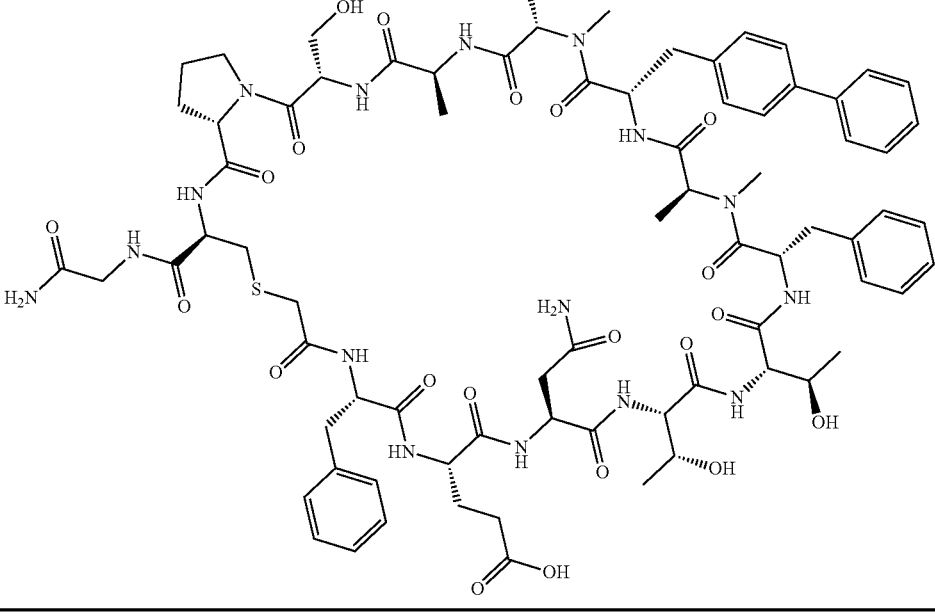 |
The following polypeptides in Table 5 were synthesized according the procedure described in Example 1 for polypeptide (1-1) using the Liberty® peptide synthesizer.
TABLE 5
| Ex. No. | Structure |
|---|---|
| 1-9 | 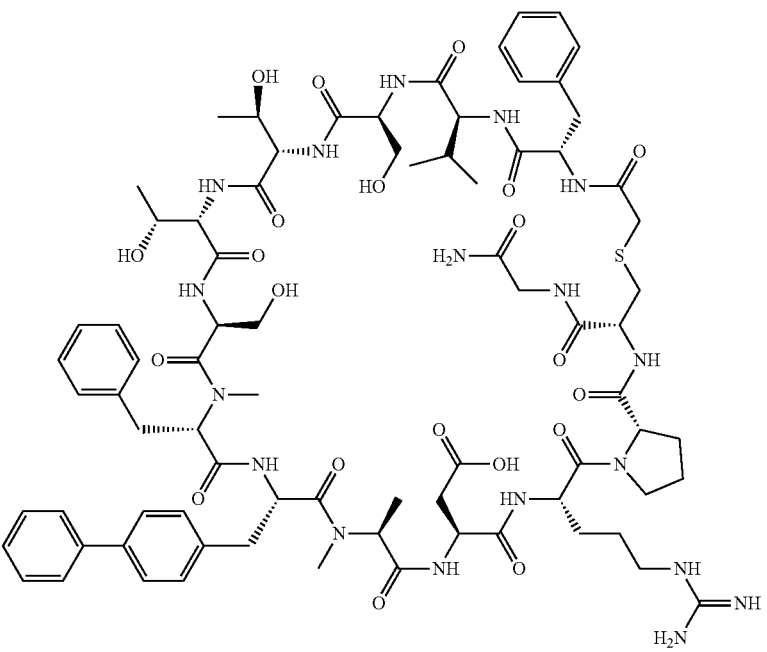 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CCCNC(=N)N)NC(=O)[C@H](CC(=O)O)NC(=O)[C@H](C)N(C)C(=O)[C@H](Cc2ccc(-c3ccccc3)cc2)NC(=O)[C@H](Cc2ccccc2)N(C)C(=O)[C@H](CO)NC(=O)[C@H]([C@@H](C)O)NC(=O)[C@H]([C@@H](C)O)NC(=O)[C@H](CO)NC1=O] |

TABLE 5-continued
| Ex. No. | Structure |
|---|---|
| 1-10 | 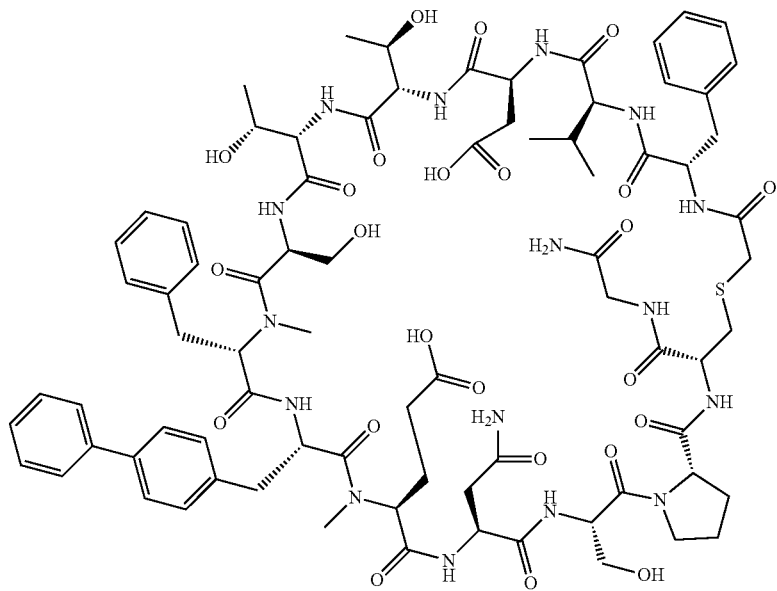 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CC(N)=O)NC(=O)[C@H](CCC(=O)O)N(C)C(=O)[C@H](Cc2ccc(-c3ccccc3)cc2)NC(=O)[C@H](Cc2ccccc2)N(C)C(=O)[C@H](CO)NC(=O)[C@H]([C@@H](C)O)NC(=O)[C@H]([C@@H](C)O)NC(=O)[C@H](CC(=O)O)NC1=O] |
| 1-12 | 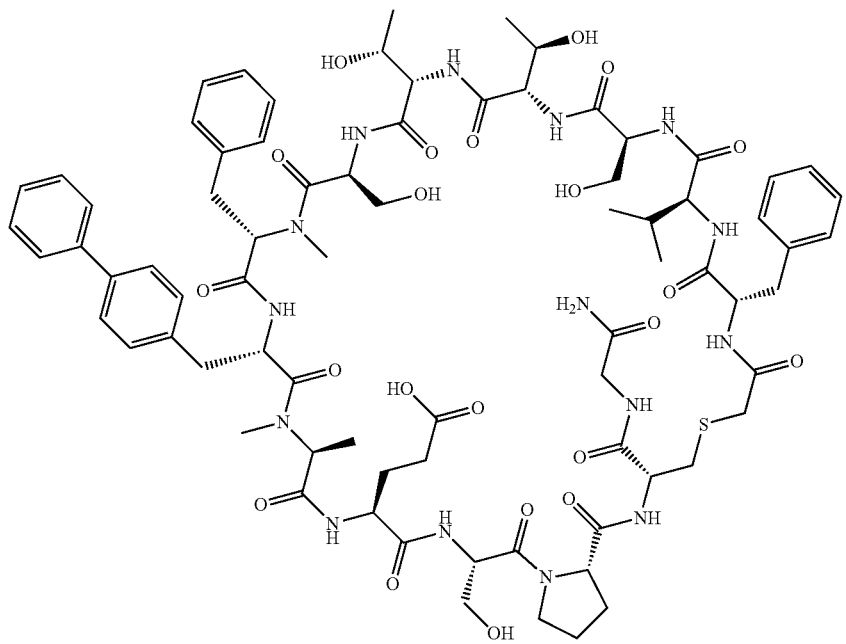 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CCC(=O)O)NC(=O)[C@H](C)N(C)C(=O)[C@H](Cc2ccc(-c3ccccc3)cc2)NC(=O)[C@H](Cc2ccccc2)N(C)C(=O)[C@H](CO)NC(=O)[C@H]([C@@H](C)O)NC(=O)[C@H]([C@@H](C)O)NC(=O)[C@H](CO)NC1=O] |

TABLE 5-continued
| Ex. No. | Structure |
|---|---|
| 1-13 | 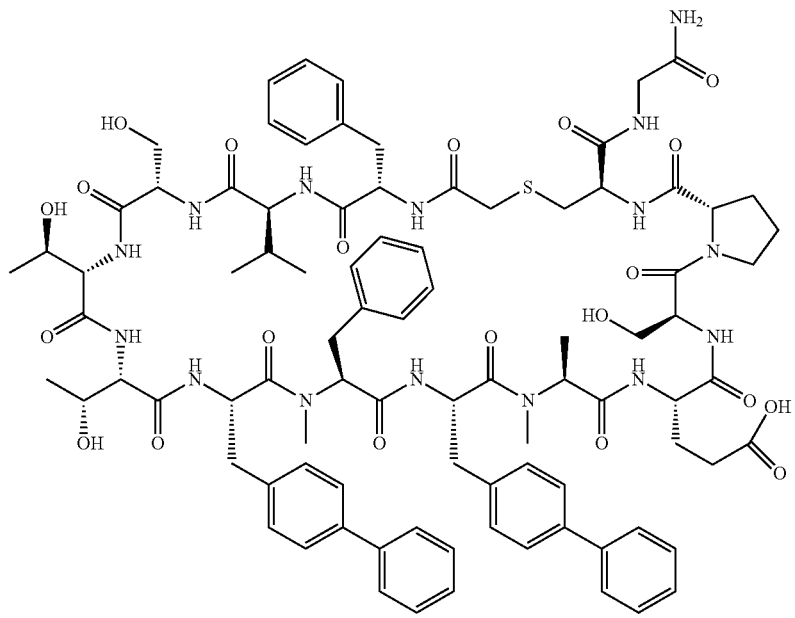 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@H](CCC(=O)O)NC(=O)[C@H](C)N(C)C(=O)[C@H](Cc2ccc(-c3ccccc3)cc2)NC(=O)[C@H](Cc2ccccc2)N(C)C(=O)[C@H](Cc2ccc(-c3ccccc3)cc2)NC(=O)[C@H]([C@@H](C)O)NC(=O)[C@H]([C@@H](C)O)NC(=O)[C@H](CO)NC1=O] |
| 1-14 | 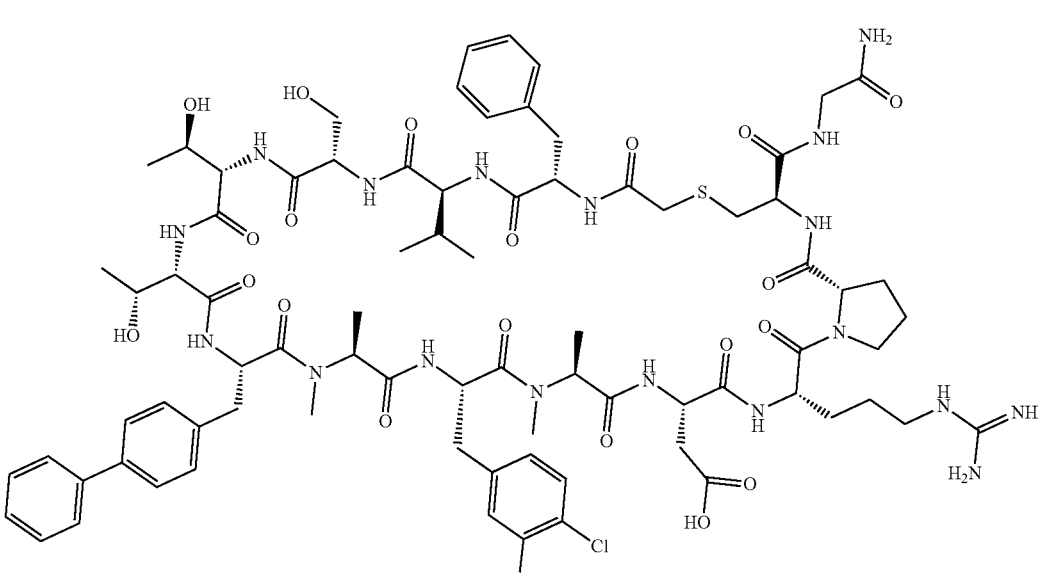 |

TABLE 5-continued
| Ex. No. | Structure |
|---|---|
| 1-15 | 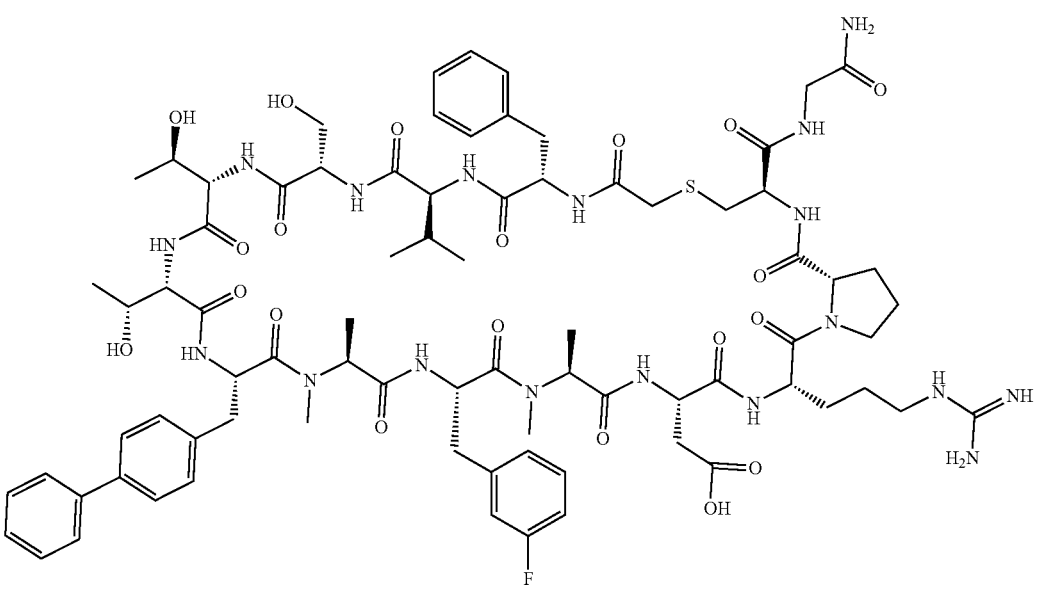 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CCCNC(=N)N)NC(=O)[C@H](CC(=O)O)NC(=O)[C@H](C)N(C)C(=O)[C@H](Cc2cccc(F)c2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@H](CO)NC1=O] |
| 1-19 | 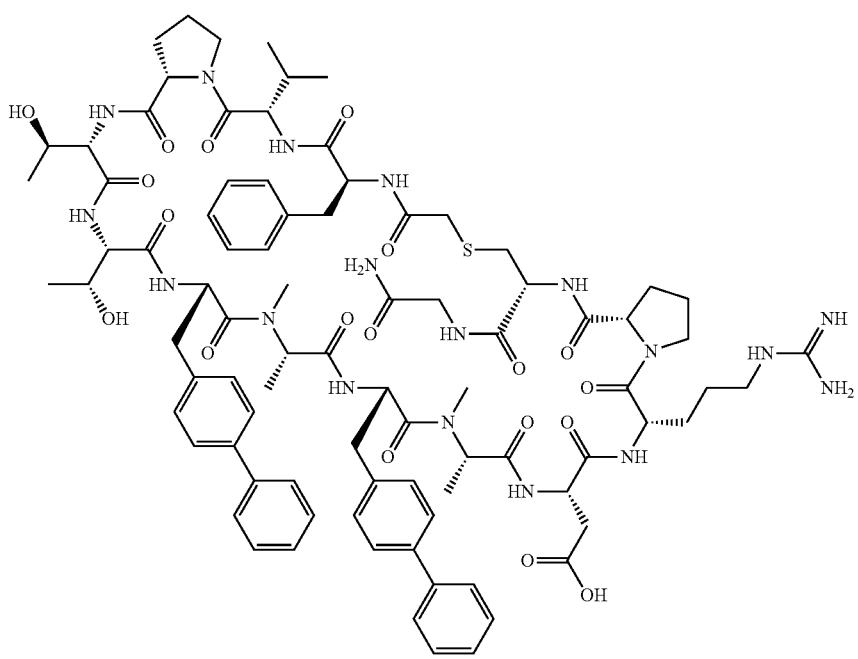 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CCCNC(=N)N)NC(=O)[C@H](CC(=O)O)NC(=O)[C@H](C)N(C)C(=O)[C@H](Cc2ccc(-c3ccccc3)cc2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@@H]2CCCN2C1=O] |

TABLE 5-continued
| Ex. No. | Structure |
|---|---|
| 1-20 | 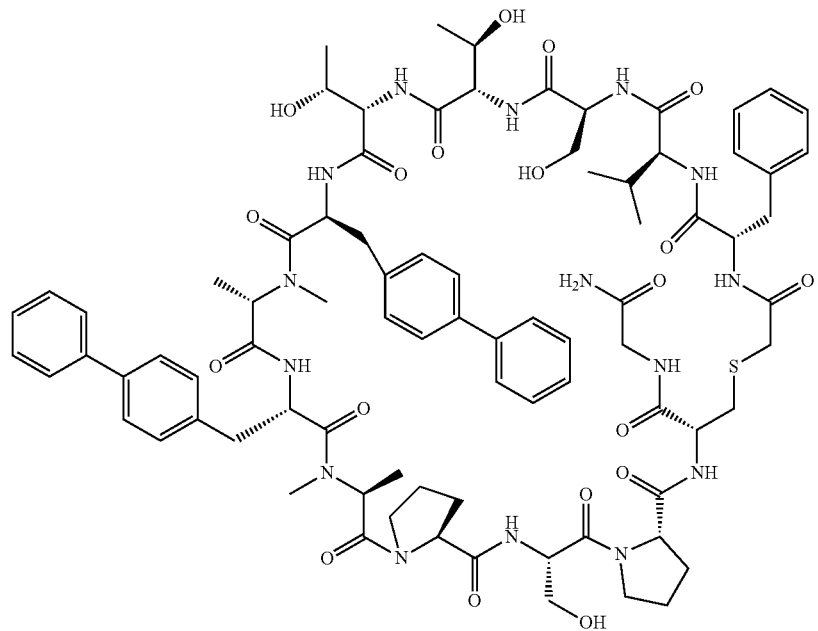 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](CO)NC(=O)[C@@H]2CCCN2C(=O)[C@H](C)N(C)C(=O)[C@H](Cc2ccc(-c3ccccc3)cc2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@H](CO)NC1=O] |
| 1-24 | 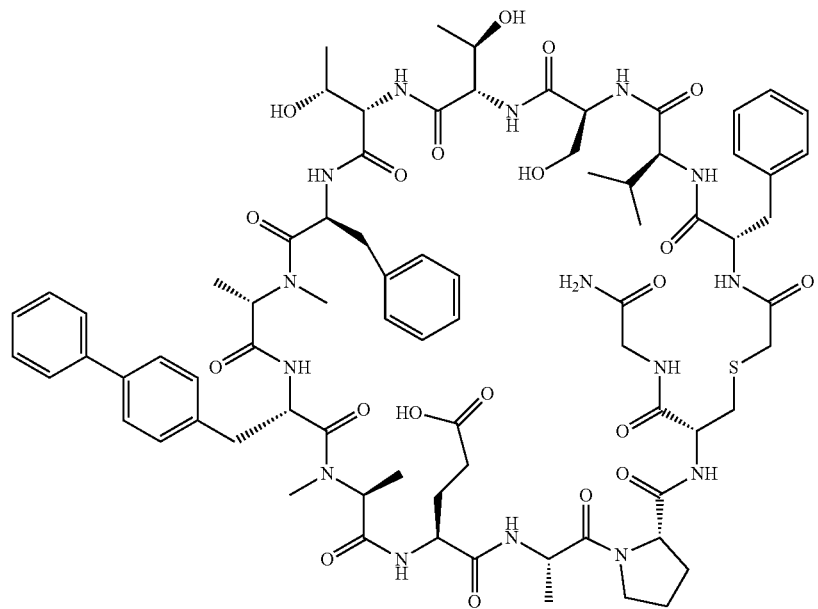 [SMILES: CC(C)[C@@H]1NC(=O)[C@H](Cc2ccccc2)NC(=O)CSC[C@@H](C(=O)NCC(N)=O)NC(=O)[C@@H]2CCCN2C(=O)[C@H](C)NC(=O)[C@H](CCC(=O)O)NC(=O)[C@H](C)N(C)C(=O)[C@H](Cc2ccc(-c3ccccc3)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](CO)NC1=O] |

| Ex. No. | Structure |
|---|---|
| 1-25 | (chemical structure) |
| 1-26 | (chemical structure) |

The analytical data for polypeptides of Examples 1-1 to Example 1-27 are summarized in Table 6 below and were generated using HRMS* or UPLC-MS** analytical methods described herein above.

TABLE 6

| Ex. No. | Calculated [M+H]+ | Measured [M+H]+ | Calculated [M+2H]$^{2+}$ | Measured [M+2H]$^{2+}$ | Retention time (min) | Conditions |
|---|---|---|---|---|---|---|
| 1-1 | 1693.7208* | 1693.7190* | 847.3643* | 847.3621* | 1.78 | BB-1 |
| 1-2 | — | — | 869.4** | 869.4** | 0.89 | B-1 |
| 1-3 | — | — | 818.4** | 818.4** | 1.18 | C-1 |
| 1-4 | — | — | 836.4** | 836.5** | 0.71 | B-1 |
| 1-5 | — | — | 825.9** | 826.1** | 0.84 | B-1 |
| 1-6 | 1642.7** | 1642.7** | 821.9** | 821.8** | 8.73 | D-1 |
| 1-7 | 1573.7** | 1573.8** | 787.4** | 787.3** | 7.88 | E-1 |

TABLE 6-continued
| Ex. No. | Calculated [M+H]+ | Measured [M+H]+ | Calculated [M+2H]2+ | Measured [M+2H]2+ | Retention time (min) | Conditions |
|---|---|---|---|---|---|---|
| 1-8 | 1668.7** | 1668.9** | 834.9** | 834.8** | 9.98 | E-1 |
| 1-9 | 1677.7735* | 1677.7680* | 839.3907* | 839.3875* | 1.96 | BB-1 |
| 1-10 | 1710.7514* | 1710.7490* | 855.8796* | 855.8774* | 2.22 | BB-1 |
| 1-11 | — | — | 868.4** | 868.8** | 0.96 | F-1 |
| 1-12 | 1622.7201* | 1622.7190* | 811.8640* | 811.8624* | 2.01 | BB-1 |
| 1-13 | 1758.7878* | 1780.7740* [M+Na]+ | 879.8978* | 879.8958* | 2.64 | BB-1 |
| 1-14 | 1729.7007* | 1729.6860* | 865.3543* | 865.3553* | 2.28 | BB-1 |
| 1-15 | 1679.7692* | 1679.7710* | 840.3885* | 840.3867* | 2.09 | BB-1 |
| 1-16 | 1618.7** | 1618.5** | 809.9** | 809.8** | 2.30 | E-1 |
| 1-17 | 1634.7** | 1634.6** | 817.9** | 817.8** | 2.05 | E-1 |
| 1-18 | 1616.8** | 1616.6** | 808.9** | 808.8** | 1.98 | E-1 |
| 1-19 | 1747.8306* | 1747.8312* | 874.4192* | 874.4199* | 1.10 | CC-1 |
| 1-20 | 1650.7666* | 1650.7680* | 825.8872* | 825.8860* | 2.59 | BB-1 |
| 1-21 | 1600.8** | 1600.6** | 800.9** | 800.8** | 2.30 | E-1 |
| 1-22 | 1573.8** | 1573.6** | 787.4** | 787.3** | 2.05 | E-1 |
| 1-23 | 1616.8** | 1616.6** | 808.9** | 808.7** | 1.98 | E-1 |
| 1-24 | 1590.7303* | 1590.7270* | 795.8691* | 795.8669* | 2.06 | BB-1 |
| 1-25 | 1682.7565* | 1682.7580* | 841.8822* | 841.8822* | 2.36 | BB-1 |
| 1-26 | 1702.6421* | 1724.6302* [M+Na]+ | 851.8250* | 851.8256* | 2.09 | BB-1 |
| 1-27 | 1605.7** | 1605.7** | — | — | 2.13 | G-1 |
Example 2: Synthesis of Ac*-F-V-P-T-T-F-(N-Me)A-(p-Cl)F-(N-Me)A-P-A-P-C*-NH₂ (2-1)
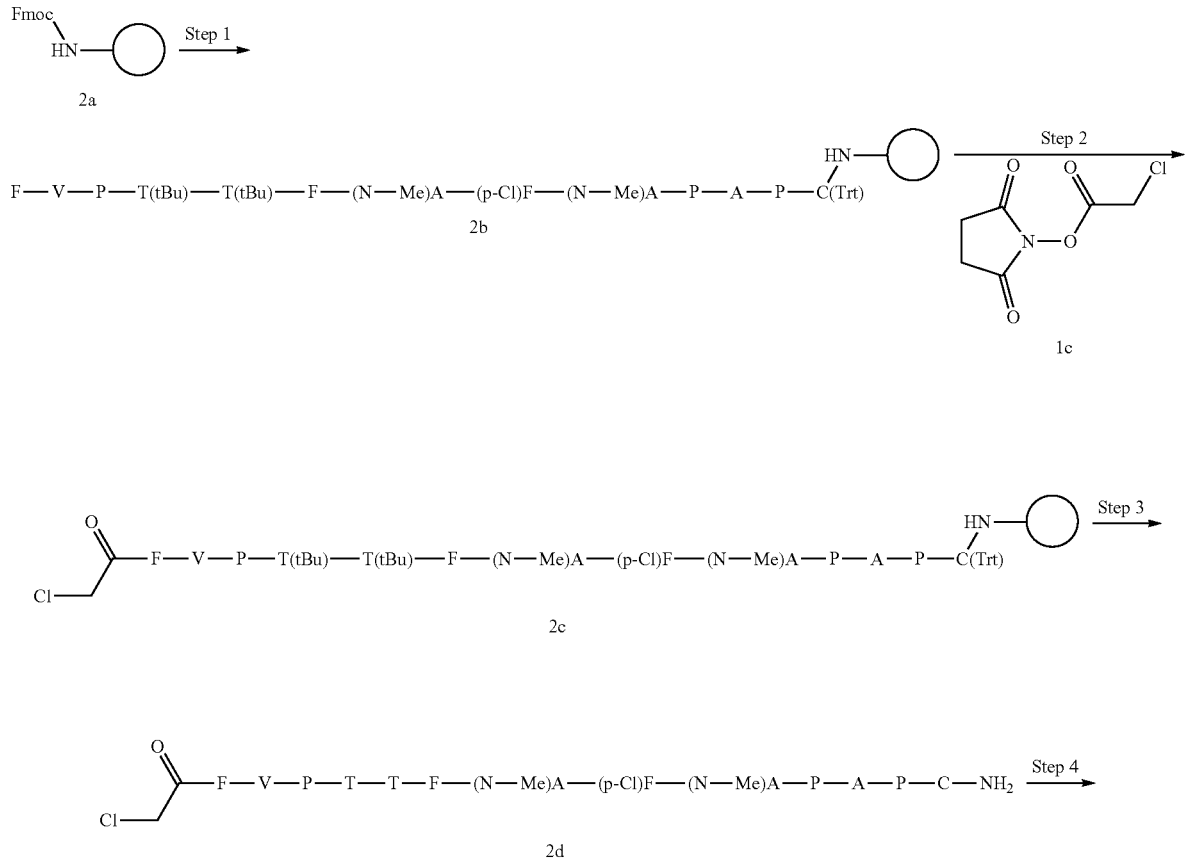

-continued

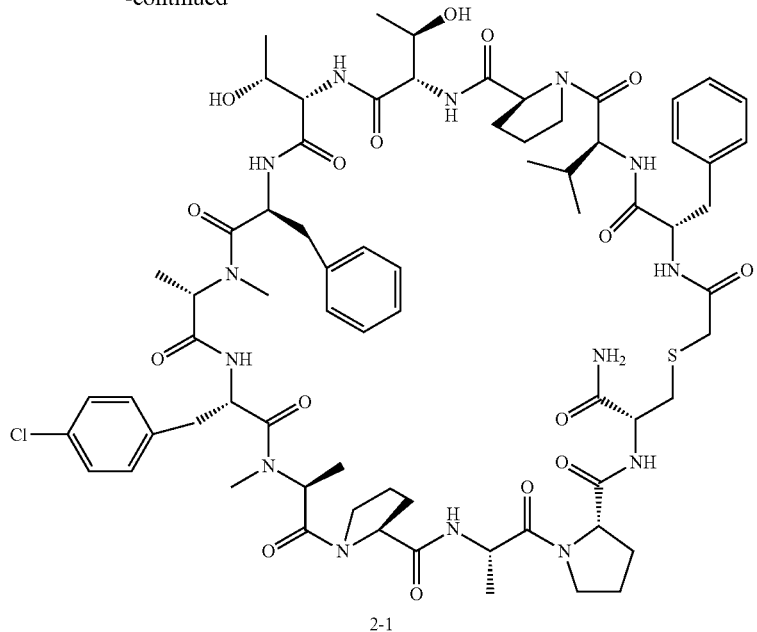

2-1

Step 1: F-V-P-T(tBu)-T(tBu)-F-(N-Me)A-(p-Cl)F-(N-Me)A-P-A-P-C-(Trt)NHresin (2b)

The peptide sequence 2b was synthesized on Fmoc-NH TentaGel™ RAM Resin (2a, 0.23 mmol/g loading, 0.1 mmol scale) on a Liberty® Peptide Synthesizer following general peptide Synthesis Cycle A-1 (Fmoc-amino acid (5 eq.; 0.2 M solution in DMF), HATU (5 eq.; 0.5 M solution in DMF) and DIPEA (5.5 eq.; 2 M solution in NMP)). The resin was then filtered and washed with DMF (2×) and DCM (3×) to provide the desired product 2b.

Step 2: ClCH$_2$C(O)-F-V-P-T(tBu)-T(tBu)-F-(N-Me)A-(p-Cl)F-(N-Me)A-P-A-P-C-(Trt)NH-resin (2c)

A solution of N-succinimidyl 2-chloroacetate (1c, 100 mg, 0.522 mmol) in NMP (6 mL) was added to the peptide resin 2b from Step 1 (0.1 mmol) and the resulting mixture was shaken at room temperature for 18 h. The resin was then drained, washed with DMF (3×) and DCM (3×), and dried to provide the desired product 2c.

Step 3: ClCH$_2$C(O)-F-V-P-T-T-F-(N-Me)A-(p-Cl)F-(N-Me)A-P-A-P-C-NH$_2$ (2d)

The resin product 2c from Step 2 was cleaved from the resin and simultaneously deprotected using Cleavage Method 1 described herein above to provide the crude peptide 2d (106 mg) as a white solid. ESI-MS m/z: 1503.7 [M−H]$^−$.

Step 4: (6S,8aS,14S,17S,20S,23S,26S,29S,31aS, 37S,40S,46R,48aS)-23,40-dibenzyl-17-(4-chlorobenzyl)-26,29-bis((R)-1-hydroxyethyl)-37-isopropyl-6,14,15,20,21-pentamethyl-5,8,13,16,19,22,25, 28,31,36,39,42,48-tridecaoxohexatetracontahydro-13H-tripyrrolo[1,2-e1:1',2'-j:1'',2''-k1][1]thia[4,7,10, 13,16,19,22,25,28,31,34,37,40]tridecaazacyclodotetracontine-46-carboxamide (2-1)

The crude peptide 2d (106 mg) from Step 3 was dissolved in DMSO (6 mL). TEA (50 µL, 0.359 mmol) was then added to get the mixture to a pH of 8-9. The resulting mixture was stirred at rt for 18 h and then concentrated down to a few mL of DMSO on a centrifugal evaporator.

The crude cyclic peptide was purified by preparative HPLC (Sunfire™ Prep O18 Column, 130 Å, 5 µm, 30×50 mm, 25-50% in 6 min, 75 mL/min, ACN in water with 0.1% TFA) and then lyophilized to provide the title polypeptide 2-1 (10 mg, 9%) as a white solid.

The following polypeptides in Table 7 were synthesized according the procedure described in Example 2 for polypeptide (2-1) using the Liberty® peptide synthesizer.

TABLE 7
| Ex. No. | Structure |
|---|---|
| 2-2 | 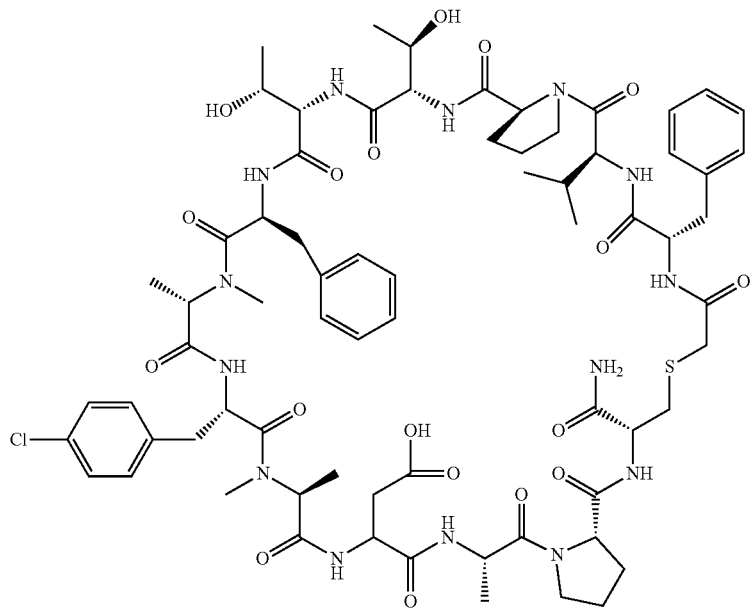 [SMILES: CC(C)[C@@H]1NC(=O)[C@H](Cc2ccccc2)NC(=O)CSC[C@@H](C(N)=O)NC(=O)[C@@H]2CCCN2C(=O)[C@H](C)NC(=O)C(CC(=O)O)NC(=O)[C@H](C)N(C)C(=O)[C@H](Cc2ccc(Cl)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@@H]2CCCN2C1=O] |
| 2-3 | 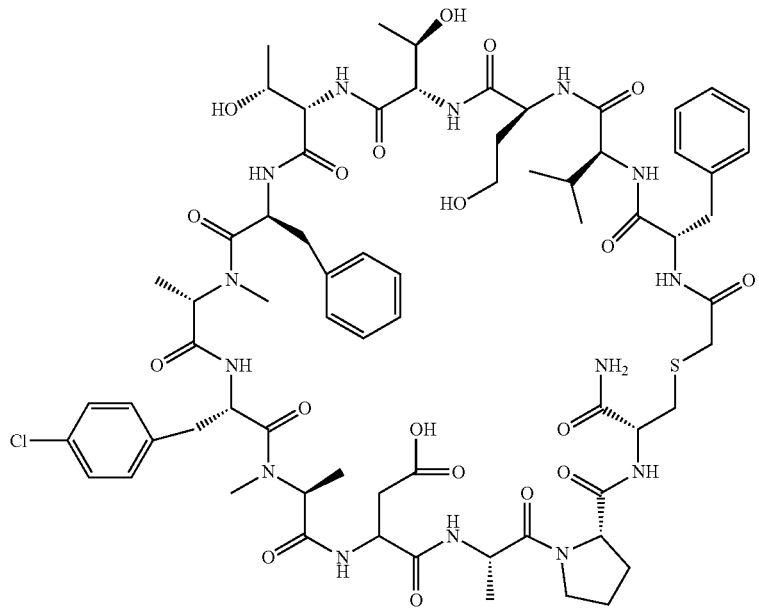 [SMILES: CC(C)[C@@H]1NC(=O)[C@H](Cc2ccccc2)NC(=O)CSC[C@@H](C(N)=O)NC(=O)[C@@H]2CCCN2C(=O)[C@H](C)NC(=O)C(CC(=O)O)NC(=O)[C@H](C)N(C)C(=O)[C@H](Cc2ccc(Cl)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](CCO)NC1=O] |

TABLE 7-continued
| Ex. No. | Structure |
|---|---|
| 2-4 | 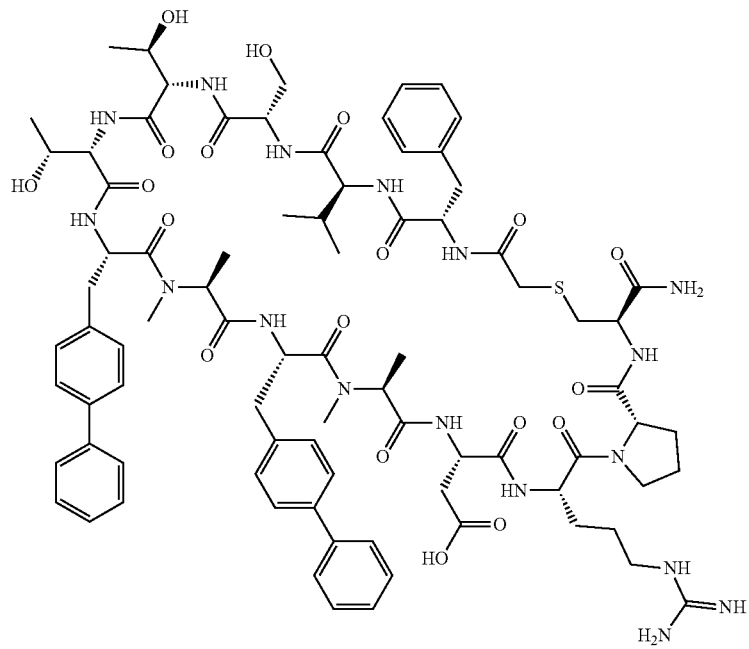 [SMILES: CC(C)[C@@H]1NC(=O)[C@H](Cc2ccccc2)NC(=O)CSC[C@@H](C(N)=O)NC(=O)[C@@H]2CCCN2C(=O)[C@H](CCCNC(=N)N)NC(=O)[C@H](CC(=O)O)NC(=O)[C@H](C)N(C)C(=O)[C@H](Cc2ccc(-c3ccccc3)cc2)NC(=O)[C@H](C)N(C)C(=O)[C@H](Cc2ccc(-c3ccccc3)cc2)NC(=O)[C@H]([C@@H](C)O)NC(=O)[C@H]([C@@H](C)O)NC(=O)[C@H](CO)NC1=O] |
| 2-5 | 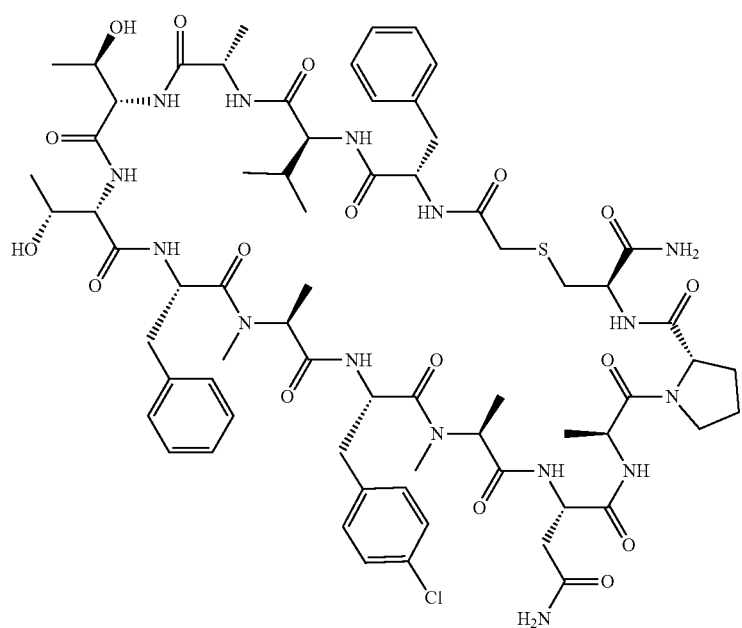 [SMILES: CC(C)[C@@H]1NC(=O)[C@H](Cc2ccccc2)NC(=O)CSC[C@@H](C(N)=O)NC(=O)[C@@H]2CCCN2C(=O)[C@H](C)NC(=O)[C@H](CC(N)=O)NC(=O)[C@H](C)N(C)C(=O)[C@H](Cc2ccc(Cl)cc2)NC(=O)[C@H](C)N(C)C(=O)[C@H](Cc2ccccc2)NC(=O)[C@H]([C@@H](C)O)NC(=O)[C@H]([C@@H](C)O)NC(=O)[C@H](C)NC1=O] |

TABLE 7-continued

| Ex. No. | Structure |
|---|---|
| 2-6 | (structure) |

The analytical data for polypeptides of Examples 2-1 to Example 2-6 are summarized in Table 8 below and were generated using the HRMS analytical methods described herein above.

TABLE 8

| Ex. No. | Calculated [M+H]$^+$ | Measured [M+H]$^+$ | Calculated [M+2H]$^{2+}$ | Measured [M+2H]$^{2+}$ | Retention time (min) | Conditions |
|---|---|---|---|---|---|---|
| 2-1 | 1469.6694 | 1469.6730 | 735.3386 | 735.3391 | 2.24 | BB-1 |
| 2-2 | 1487.6436 | 1487.6500 | 744.3257 | 744.3273 | 2.20 | BB-1 |
| 2-3 | 1491.6385 | 1491.6410 | 746.3232 | 746.3227 | 2.08 | BB-1 |
| 2-8 | | | 840.8981 | 840.8903 | 4.07 | AA-1 |
| 2-5 | 1460.6439 | 1460.6497 | 730.8259 | 730.8261 | 2.11 | BB-1 |
| 2-6 | 1453.6593 | 1453.6586 | 727.3336 | 727.3324 | 1.88 | BB-1 |

Example 3: Synthesis of Ac*-F-V-N-T-T-F-(N-Me)A-B-(N-Me)A-(N-Me)E-A-P-C*-NHEt (3-1)

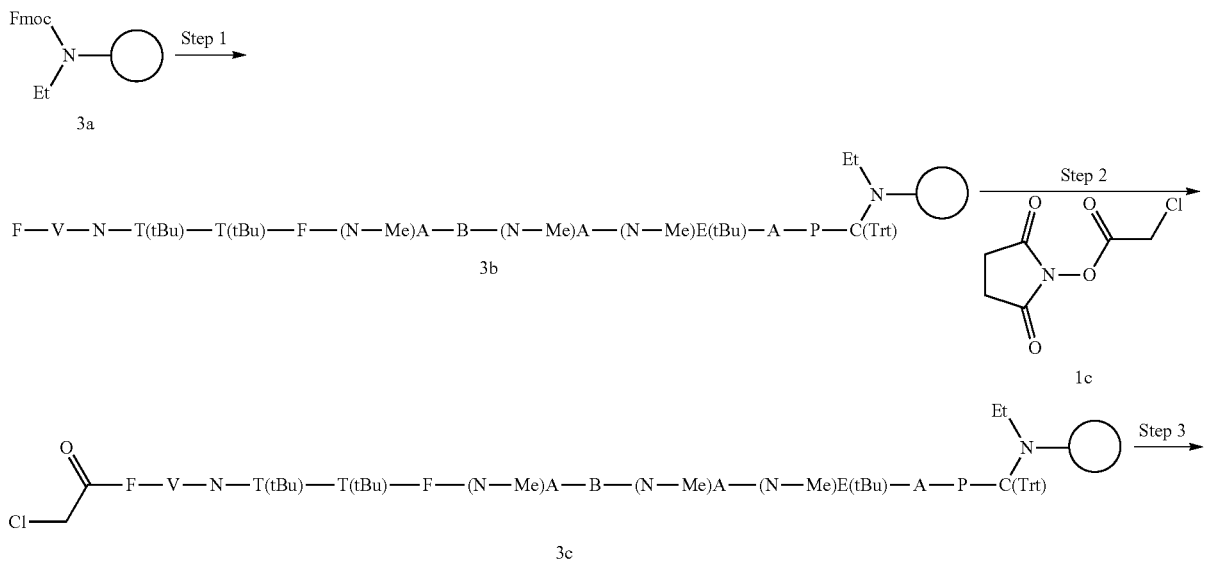

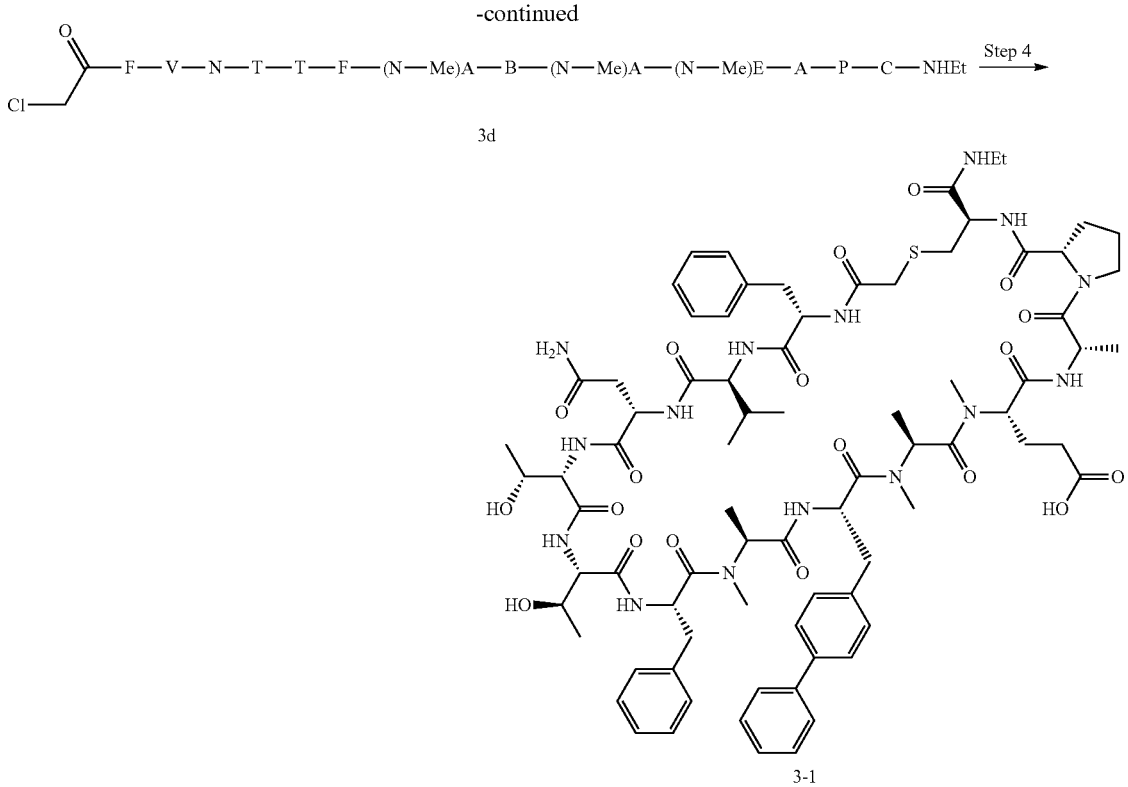

3d 3-1

Step 1: F-V-N-T(tBu)-T(tBu)-F-(N-Me)A-B-(N-Me)A-(N-Me)E(tBu)-A-P-C(Trt)N(Et)resin (3b)

The peptide sequence 3b was synthesized on {3-[(ethyl-Fmoc-amino)methyl]-indol-1-yl}-acetyl AM resin (3a, 0.93 mmol/g loading, 0.1 mmol scale) on a Prelude® peptide synthesizer following general peptide synthesis as described herein below. The resin was then filtered and washed with DMA to provide the desired product 3b.

| AA | Synthesis Cycle |
|---|---|
| Fmoc-C(Trt) | B-2 |
| Fmoc-(N-Me)AA | B-2 |
| Any Fmoc-AA coupled to N-methyl AA | B-2 |
| Other Fmoc-AA | B-1 |

Synthesis Cycle B-1: Fmoc-AA (3 eq, 0.2 M solution in NMP), HCTU (3 eq. 0.3 M solution in NMP), and DIPEA (3.3 eq, 0.66 M solution in NMP).

Synthesis Cycle B-2: Fmoc-AA (3 eq, 0.2 M solution in NMP), PyOxim (3 eq. 0.3 M solution in NMP), and DIPEA (6.3 eq, 0.66 M solution in NMP).

Step 2: ClCH$_2$C(O)-F-V-N-T(tBu)-T(tBu)-F-(N-Me)A-B-(N-Me)A-(N-Me)E(tBu)-A-P-C(Trt)N(Et)-resin (3c)

A solution of N-succinimidyl 2-chloroacetate (1c, 96 mg, 0.5 mmol) in NMP (3 mL) was added to the peptide resin 3b from Step 1 (0.1 mmol) and the resulting mixture was shaken at room temperature for 16 h. The resin was then drained, washed with DMF (3×) and DCM (4×), and dried to provide the desired product 3c.

Step 3: ClCH$_2$C(O)-F-V-N-T-T-F-(N-Me)A-B-(N-Me)A-(N-Me)E-A-P-C-N(H)Et (3d)

The peptide resin product 3c from Step 2 was cleaved from the resin and simultaneously deprotected using Cleavage Method 2 described herein above to provide the crude peptide 3d. The crude peptide was then purified by preparative HPLC (Atlantis® T3 OBD Prep Column, 100 Å, 5 μm, 30×150 mm, 5-35% in 2.5 min, 35-55% in 12 min ACN in water with 0.1% TFA). Fractions containing the product were lyophilized, affording the product 3d as white fluffy solid (36 mg, 22%). ESI-MS m/z: 1638.6 [M+H]$^+$.

Step 4: 3-((3R,9S,12S,15S,18S,21S,24S,27S,30S,33S,36S,39S,44aS)-30-([1,1'-biphenyl]-4-ylmethyl)-15-(2-amino-2-oxoethyl)-9,24-dibenzyl-3-(ethylcarbamoyl)-18,21-bis((R)-1-hydroxyethyl)-12-isopropyl-26,27,32,33,35,39-hexamethyl-1,7,10,13,16,19,22,25,28,31,34,37,40-tridecaoxodotetracontahydro-6H-pyrrolo[2,1-f][1]thia[4,7,10,13,16,19,22,25,28,31,34,37,40]tridecaazacyclodotetracontin-36-yl)propanoic acid (3-1)

The peptide 3d from Step 3 (36 mg, 0.022 mmol) was dissolved in DMA (22 mL) and DIPEA (220 μL, 1.26 mmol) was added. The resulting mixture was stirred at rt for 18 h and then concentrated in vacuo. The crude cyclic peptide was purified by preparative HPLC (SunFire™ C18 Prep Column, 100 Å, 5 μm, 30×100 mm, 30 mL/min, 20-60% in 30 min, ACN in water with 0.1% TFA) and the fractions containing the desired product were lyophilized to provide the title polypeptide 3-1 (27 mg, 76%) as a white solid.

The following polypeptides in Table 9 were synthesized according the procedure described in Example 3 for polypeptide (3-1).

TABLE 9
| Ex. No | Structure |
|---|---|
| 3-2 | 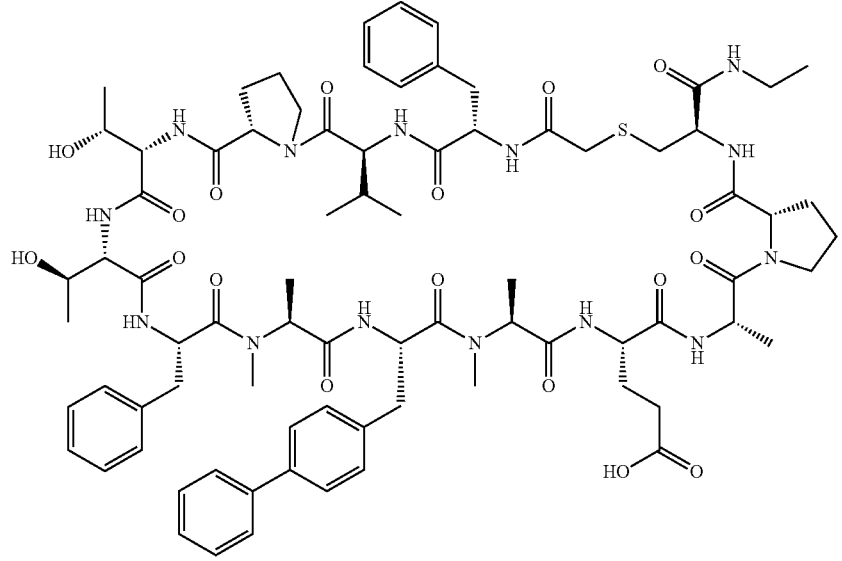 [SMILES: CCNC(=O)[C@@H]1CSCC(=O)N[C@@H](Cc2ccccc2)C(=O)N[C@@H](C(C)C)C(=O)N2CCC[C@H]2C(=O)N[C@@H]([C@@H](C)O)C(=O)N[C@@H]([C@@H](C)O)C(=O)N[C@@H](Cc2ccccc2)C(=O)N(C)[C@@H](C)C(=O)N[C@@H](Cc2ccc(-c3ccccc3)cc2)C(=O)N(C)[C@@H](C)C(=O)N[C@@H](CCC(=O)O)C(=O)N[C@@H](C)C(=O)N2CCC[C@H]2C(=O)N1] |
| 3-3 | 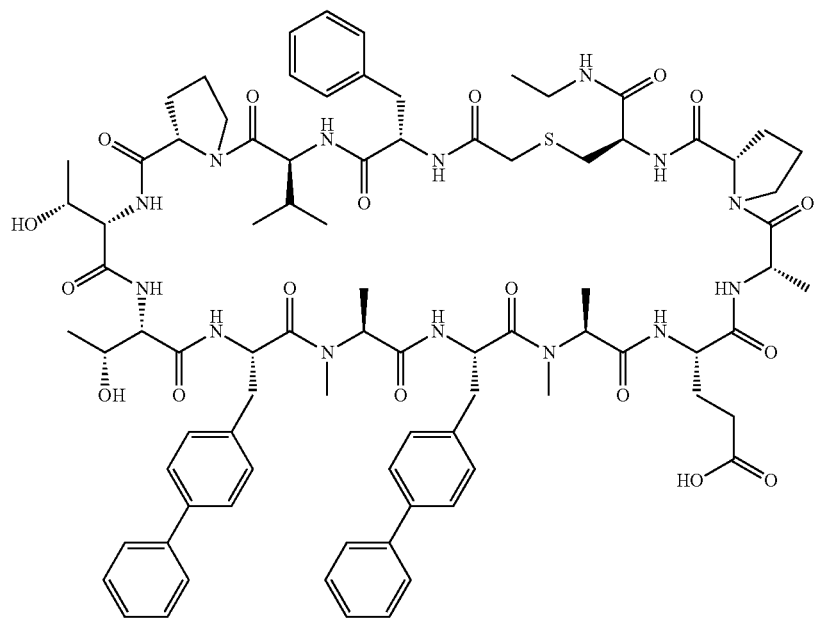 [SMILES: CCNC(=O)[C@@H]1CSCC(=O)N[C@@H](Cc2ccccc2)C(=O)N[C@@H](C(C)C)C(=O)N2CCC[C@H]2C(=O)N[C@@H]([C@@H](C)O)C(=O)N[C@@H]([C@@H](C)O)C(=O)N[C@@H](Cc2ccc(-c3ccccc3)cc2)C(=O)N(C)[C@@H](C)C(=O)N[C@@H](Cc2ccc(-c3ccccc3)cc2)C(=O)N(C)[C@@H](C)C(=O)N[C@@H](CCC(=O)O)C(=O)N[C@@H](C)C(=O)N2CCC[C@H]2C(=O)N1] |

TABLE 9-continued

| Ex. No | Structure |
|---|---|
| 3-4 | 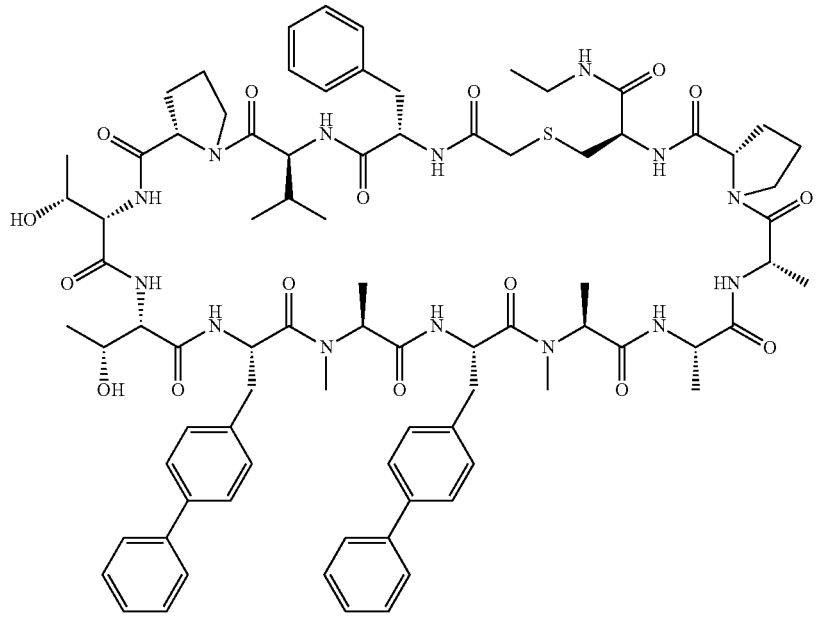 [SMILES: CCNC(=O)[C@@H]1CSCC(=O)N[C@@H](Cc2ccccc2)C(=O)N[C@@H](C(C)C)C(=O)N2CCC[C@H]2C(=O)N[C@@H]([C@@H](C)O)C(=O)N[C@@H]([C@@H](C)O)C(=O)N[C@@H](Cc2ccc(-c3ccccc3)cc2)C(=O)N(C)[C@@H](C)C(=O)N[C@@H](Cc2ccc(-c3ccccc3)cc2)C(=O)N(C)[C@@H](C)C(=O)N[C@@H](C)C(=O)N[C@@H](C)C(=O)N2CCC[C@H]2C(=O)N1] |

The analytical data for polypeptides of Examples 3-1 to Example 3-4 are summarized in Table 10 below and were generated using the UPLC-MS analytical methods described herein above.

TABLE 10

| Ex. No | Calculated $[M + H]^+$ | Measured $[M + H]^+$ | Calculated $[M + 2H]^{2+}$ | Measured $[M + 2H]^{2+}$ | Retention time (min) | Conditions |
|---|---|---|---|---|---|---|
| 3-1 | 1602.8 | 1602.6 | 801.9 | 802.2 | 2.34 | G-1 |
| 3-2 | 1571.8 | 1571.6 | 786.4 | 786.3 | 2.44 | A-1 |
| 3-3 | 1647.8 | 1647.8 | 824.4 | 824.4 | 2.56 | H-1 |
| 3-4 | 1589.8 | 1589.8 | 795.4 | 795.4 | 2.73 | A-1 |

Example 4: PCSK9 Ligand Binding Assay

The PCSK9 binding of the cyclic polypeptides of the disclosure were measured using a time resolved fluorescence resonance energy transfer (TR-FRET) assay. This time resolved fluorescence resonance energy transfer (TR-FRET) assay measures the ability of a cyclic polypeptide of the disclosure to interfere with the binding of human PCSK9 to human LDLR, providing measures of both potency ($IC_{50}$) and efficacy ($A_{max}$).

Materials
  Human PCSK9
  Human PCSK9 Alexa Fluor 647
  Human LDLR extracellular domain-Europium Kryptate
  Proxi plate-low volume assay plate (PerkinElmer #6008280)
  Greiner V-bottom (Greiner BioOne #781280)
  Assay Buffer
    20 mM HEPES, pH 7.5
    150 mM NaCl
    1 mM $CaCl_2$
    0.01% v/v Tween20
    0.01% w/v BSA A master compound plate was prepared in a Greiner V bottom plate by diluting cyclic polypeptides of the disclosure in dimethylsulfoxide to the correct concentration for the desired top concentration based on the desired final concentration: for a 30 uM final concentration the master plate concentration is 1.5 mM (68 uL DMSO+12 uL 10 mM of a cyclic polypeptide of the disclosure), for a 10 uM final concentration the master plate concentration is 0.5 mM (76 uL DMSO+4 uL 10 mM of a cyclic polypeptide of the disclosure), for a 3 uM final concentration the master plate concentration is 150 uM (69 uL DMSO+1 uL 10 mM a cyclic peptide of the disclosure). These solutions were pipetted into columns 1 and 11 of the compound plate. Threefold serial dilutions were generated in columns 2-10 and 12-20 of the compound plate by transferring 10 uL into 20 μL of DMSO. Columns 21 and 22 of the compound plate were negative controls containing DMSO alone.

An intermediate plate was generated in a Greiner V bottom plate by transferring 8 uL from each well of the master plate into a corresponding well containing 92 μL of assay buffer and mixing thoroughly.

A Proxi plate-low volume assay plate was used for the assay. To all wells of the plate was added 10 μL of 16 nM Human PCSK9 Alexa Fluor 647, followed by 5 uL from the intermediate plate. For the positive control wells in columns 23 and 24 of the plate, 5 μL of unlabeled human PCSK9 was added at 4 uM in assay buffer containing 8% DMSO. Following a 30 minute incubation, 5 μL of 4 nM Human LDLR extracellular domain-Europium Kryptate was added and the mixture was incubated for an additional 2 hours.

The TR-FRET signal was measured on an EnVision or PheraStar instrument with a 60 s delay, 330 nm excitation and 665 nm emission (FRET), and 330 nM excitation and 615 nm (Europium). The FRET ratio (FRET/Europium) was used for calculations.

Data Analysis

No inhibition (0%) was observed from the wells containing DMSO (Control) in columns 21 and 22 of the compound plate. Full inhibition (100%) was observed from the wells containing 1 uM human PCSK9 (Control) in columns 23 and 24 of the plate. Data is expressed as percent inhibition: (value-0%)/(100%-0%).

TABLE 11

PCSK9 activity of cyclic polypeptides of the disclosure in the PCSK9 Fret assay.

| Ex. No. | PCSK9 FRET assay IC$_{50}$ (μM) | Maximum % inhibition |
|---|---|---|
| 1-1 | 0.0026 | 65 |
| 1-2 | 0.0013 | 41 |
| 1-3 | 0.0021 | 55 |
| 1-4 | 0.004 | 60 |
| 1-5 | 0.035 | 95 |
| 1-6 | 0.012 | 97 |
| 1-7 | 0.41 | 60 |
| 1-8 | 0.0023 | 58 |
| 1-9 | 0.003 | 35 |
| 1-10 | 0.006 | 90 |
| 1-11 | 0.0036 | 55 |

TABLE 11-continued

PCSK9 activity of cyclic polypeptides of the disclosure in the PCSK9 Fret assay.

| Ex. No. | PCSK9 FRET assay IC$_{50}$ (μM) | Maximum % inhibition |
|---|---|---|
| 1-12 | 0.014 | 87 |
| 1-13 | 0.0078 | 86 |
| 1-14 | 0.0012 | 49 |
| 1-15 | 0.012 | 53 |
| 1-16 | 0.0074 | 91 |
| 1-17 | 0.017 | 91 |
| 1-18 | 0.011 | 53 |
| 1-19 | 0.0027 | 38 |
| 1-20 | 0.0081 | 35 |
| 1-21 | 0.0072 | 81 |
| 1-22 | 0.012 | 49 |
| 1-23 | 0.022 | 36 |
| 1-24 | 0.0068 | 70 |
| 1-25 | 0.0025 | 68 |
| 1-26 | 0.0024 | 84 |
| 1-27 | 0.41 | 55 |
| 2-1 | 0.0115 | 50 |
| 2-2 | 0.0004 | 72 |
| 2-3 | 0.00004 | 75 |
| 2-4 | 0.0018 | 28 |
| 2-5 | 0.0011 | 46 |
| 2-6 | 0.0054 | 83 |
| 3-1 | 0.085 | 61 |
| 3-2 | 0.0042 | 83 |
| 3-3 | 0.0022 | 87 |
| 3-4 | 0.0014 | 49 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A cyclic polypeptide selected from:

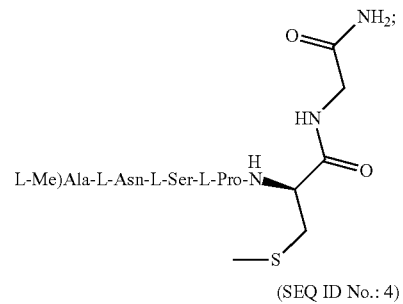

(SEQ ID No.: 6)
L-Phe-L-Val-L-Asp-L-Thr-L-Thr-L-Ser-L-(N-Me)-Phe-L-(4-CF)Phe-L-(N-
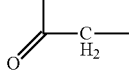
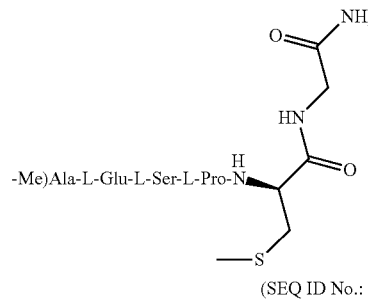
-Me)Ala-L-Glu-L-Ser-L-Pro-N (SEQ ID No.: 7)
L-Phe-L-Val-L-Asp-L-Thr-L-Thr-L-Ser-L-(N-Me)-Ala-L-Bip-L-(N-
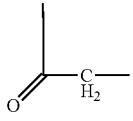
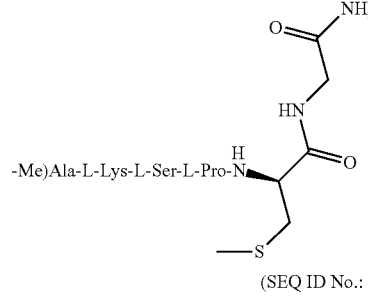
-Me)Ala-L-Lys-L-Ser-L-Pro-N (SEQ ID No.: 8)
L-Phe-L-Val-L-Ser-L-Thr-L-Thr-L-Bip-L-(N-Me)Ala-L-Bip-L-(N-
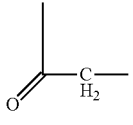
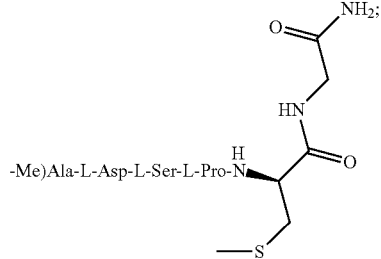
-Me)Ala-L-Asp-L-Ser-L-Pro-N (SEQ ID No.: 9)
L-Phe-L-Val-L-Ser-L-Thr-L-Thr-L-Ser-L-(N-Me)Phe-L-Bip-L-(N-
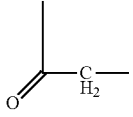

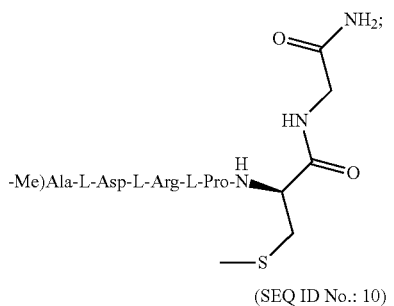
-Me)Ala-L-Asp-L-Arg-L-Pro-N (SEQ ID No.: 10)
L-Phe-L-Val-L-Asp-L-Thr-L-Thr-L-Bip-L-(N-Me)Ala-L-Bip-L-(N-
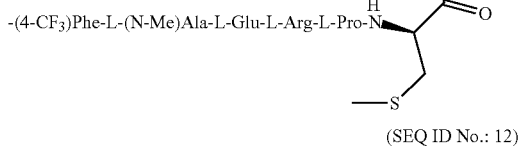
-Me)Ala-L-Glu-L-Ser-L-Pro-N (SEQ ID No.: 11)
L-Phe-L-Val-L-Ser-L-Thr-L-Thr-L-(4-CF₃)Phe-L-(N-Me)Ala-L-
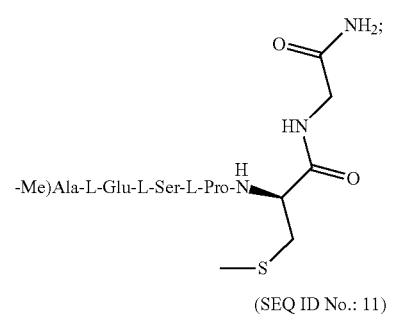
-(4-CF₃)Phe-L-(N-Me)Ala-L-Glu-L-Arg-L-Pro-N (SEQ ID No.: 12)
L-Phe-L-Val-L-Ser-L-Thr-L-Thr-L-Ser-L-(N-Me)Phe-L-Bip-L-(N-Me)Ala-
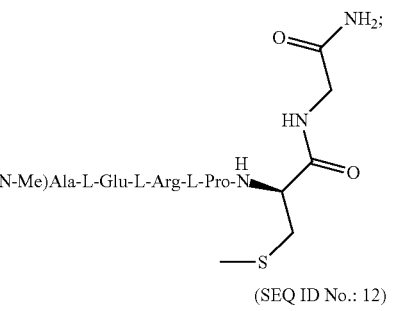
-L-Glu-L-Ser-L-Pro-N
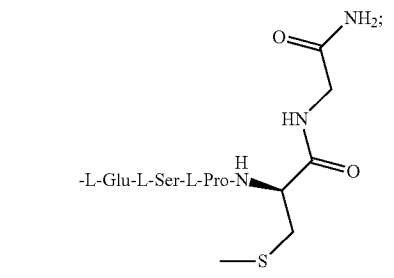

(SEQ ID No.: 13)

L-Phe-L-Val-L-Ser-L-Thr-L-Thr-L-Bip-L-(N-Me)Phe-L-Bip-L-(N-Me)Ala-

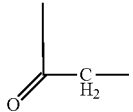

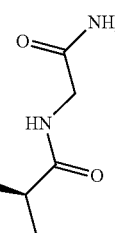

-L-Glu-L-Ser-L-Pro-N (SEQ ID No.: 14)

L-Phe-L-Val-L-Ser-L-Thr-L-Thr-L-Bip-L-(N-Me)Ala-L-(3,4-diCl)Phe-L-

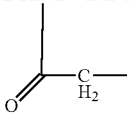

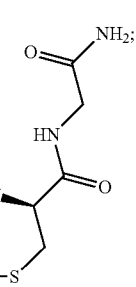

-(N-Me)Ala-L-Asp-L-Arg-L-Pro-N (SEQ ID No.: 15)

L-Phe-L-Val-L-Ser-L-Thr-L-Thr-Bip-L-(N-Me)Ala-L-(3-F)Phe-L-(N-

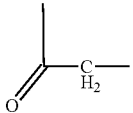

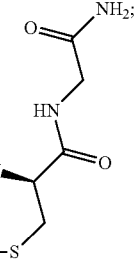

-Me)Ala-L-Asp-L-Arg-L-Pro-N (SEQ ID No.: 16)

L-Phe-L-Val-L-Asp-L-Thr-L-Thr-L-Ala-L-(N-Me)Phe-L-Bip-L-(N-Me)Ala-

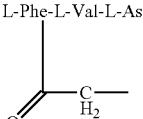

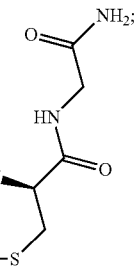

-L-Glu-L-Ala-L-Pro-N (SEQ ID No.: 17)

L-Phe-L-Val-L-Asp-L-Thr-L-Thr-L-Phe-L-(N-Me)Ala-L-Bip-L-(N-Me)Ala-

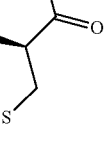

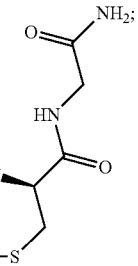

-L-Glu-L-Ser-L-Pro-N (SEQ ID No.: 18)

L-Phe-L-Val-L-Asn-L-Thr-L-Thr-L-Ala-L-(N-Me)Phe-L-Bip-L-(N-Me)Ala-

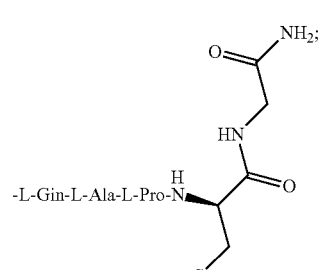

-L-Gln-L-Ala-L-Pro-N (SEQ ID No.: 19)

L-Phe-L-Val-L-Pro-L-Thr-L-Thr-L-Bip-L-(N-Me)Ala-L-Bip-L-(N-Me)Ala-

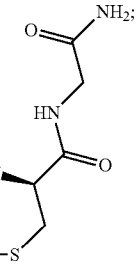

-L-Asp-L-Arg-L-Pro-N (SEQ ID No.: 20)
L-Phe-L-Val-L-Ser-L-Thr-L-Thr-L-Bip-L-(N-Me)Ala-L-Bip-L-(N-Me)Ala-

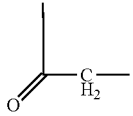

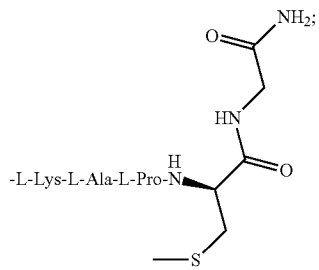

-L-Pro-L-Ser-L-Pro-N (SEQ ID No.: 21)
L-Phe-L-Val-L-Pro-L-Thr-L-Thr-L-Ala-L-(N-Me)Phe-L-Bip-L-(N-Me)Ala-

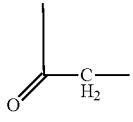

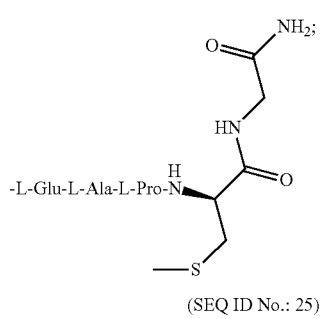

-L-Glu-L-Ala-L-Pro-N (SEQ ID No.: 22)
L-Phe-L-Val-L-Ala-L-Thr-L-Thr-L-Phe-L-(N-Me)Ala-L-Bip-L-(N-Me)Ala-

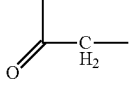

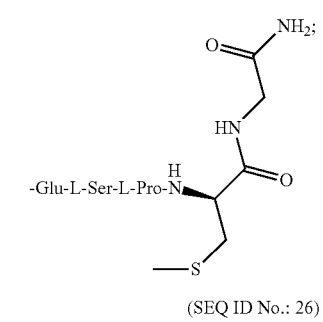

-L-Lys-L-Ala-L-Pro-N (SEQ ID No.: 23)
L-Phe-L-Val-L-Asn-L-Thr-L-Thr-L-Phe-L-(N-Me)Ala-L-Bip-L-(N-Me)Ala-

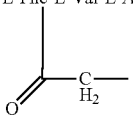

(SEQ ID No.: 24)
L-Phe-L-Val-L-Ser-L-Thr-L-Thr-L-Phe-L-(N-Me)Ala-L-Bip-L-(N-Me)Ala-

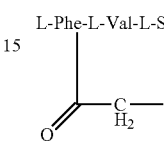

(SEQ ID No.: 25)
L-Phe-L-Val-L-Ser-L-Thr-L-Bip-L-(N-Me)Ala-L-Bip-L-(N-Me)Ala-L-

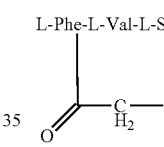

(SEQ ID No.: 26)
L-Phe-L-Val-L-Asp-L-Thr-L-Thr-L-Bip-L-(N-Me)Ala-L-(3,4-diCl)Phe-L-

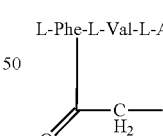

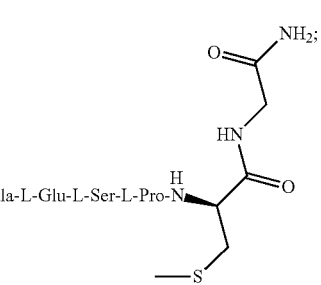

-(N-Me)Ala-L-Glu-L-Ser-L-Pro-N (SEQ ID No.: 27)

L-Phe-L-Glu-L-Asn-L-Thr-L-Thr-L-Phe-L-(N-Me)Ala-L-Bip-L-(N-Me)Ala-
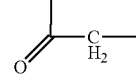

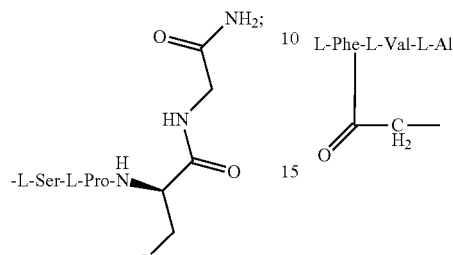

(SEQ ID No.: 28)

L-Phe-L-Val-L-Pro-L-Thr-L-Thr-L-Phe-L-(N-Me)Ala-L-(4-Cl)Phe-L-(N-
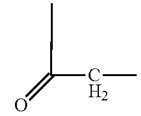

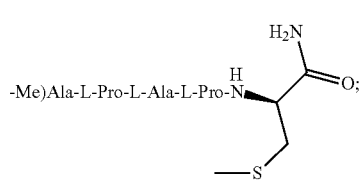

(SEQ ID No.: 29)

L-Phe-L-Val-L-Pro-L-Thr-L-Thr-L-Phe-L-(N-Me)Ala-L-(4-Cl)Phe-L-(N-
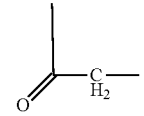

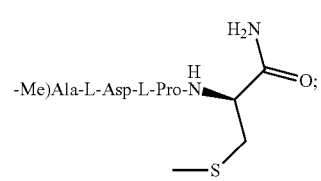

(SEQ ID No.: 30)

L-Phe-L-Val-L-Hse-L-Thr-L-Thr-L-Phe-L-(N-Me)Ala-L-(4-Cl)Phe-L-(N-
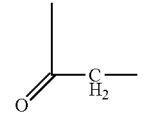

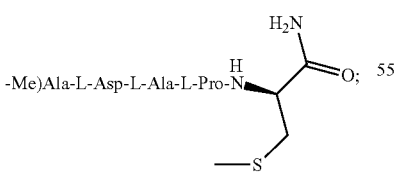

(SEQ ID No.: 31)

L-Phe-L-Val-L-Ser-L-Thr-L-Thr-L-Bip-L-(N-Me)Ala-L-Bip-L-(N-Me)Ala-
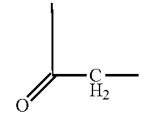

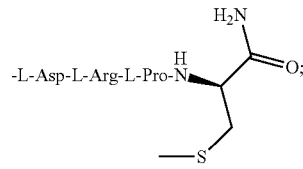

(SEQ ID No.: 32)

L-Phe-L-Val-L-Ala-L-Thr-L-Thr-L-Phe-L-(N-Me)Ala-L-(4-Cl)Phe-L-(N-

(SEQ ID No.: 33)

L-Phe-L-Val-L-Pro-L-Thr-L-Thr-L-Val-L-(N-Me)Ala-L-(4-Cl)Phe-L-(N-
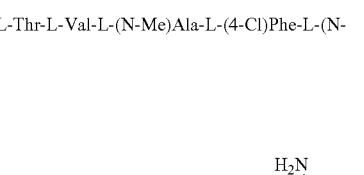

(SEQ ID No.: 34)

L-Phe-L-Val-L-Asn-L-Thr-L-Thr-Phe-L-(N-Me)Ala-L-Bip-L-(N-Me)Ala-
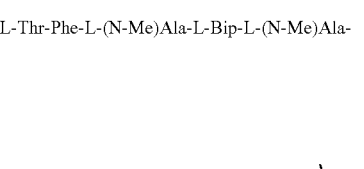

(SEQ ID No.: 35)

L-Phe-L-Val-L-Pro-L-Thr-L-Thr-L-Phe-L-(N-Me)Ala-L-Bip-L-(N-Me)Ala-
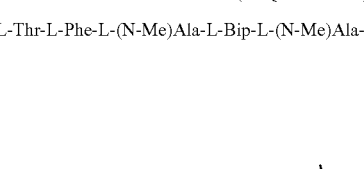

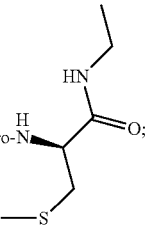

(SEQ ID No.: 36)
L-Phe-L-Val-L-Pro-L-Thr-L-Thr-L-Bip-L-(N-Me)Ala-L-Bip-L-(N-Me)Ala-
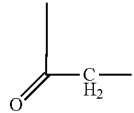
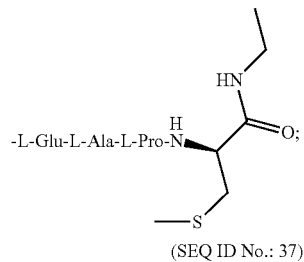
(SEQ ID No.: 37)
L-Phe-L-Val-L-Pro-L-Thr-L-Thr-L-Bip-L-(N-Me)Ala-L-Bip-L-(N-Me)Ala-
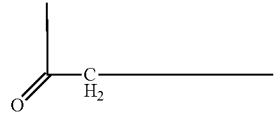
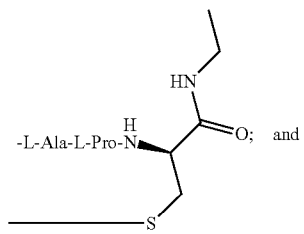
(SEQ ID No.: 38)
L-Phe-L-Val-L-Pro-L-Thr-L-Thr-L-Bip-L-(N-Me)Ala-L-Bip-L-(N-Me)Ala-
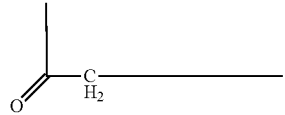
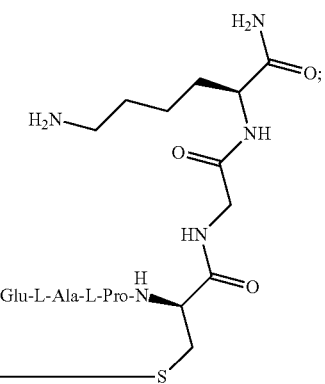
or a pharmaceutically acceptable salt, hydrate, solvate, stereoisomer, or tautomer thereof.
* * * * *

SEQUENCE LISTING

```
<160> NUMBER OF SEQ ID NOS: 67

<210> SEQ ID NO 1
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)E
<220> FEATURE:
<221> NAME/KEY: source
<223> OTHER INFORMATION: /note="See specification as filed for detailed
      description of substitutions and preferred embodiments"

<400> SEQUENCE: 1

Phe Val Asp Thr Thr Ser Xaa Xaa Xaa Asn Ser Pro Cys Gly
1               5                   10
```

```
<210> SEQ ID NO 2
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 2

Phe Val Ser Thr Thr Xaa Xaa Xaa Xaa Asp Arg Pro Cys Gly
1               5                   10

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 3

Phe Val Asp Thr Thr Ser Xaa Xaa Xaa Asn Ser Pro Cys Gly
1               5                   10

<210> SEQ ID NO 4
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
```

```
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 4

Phe Val Asp Ser Thr Tyr Xaa Xaa Xaa Asn His Pro Cys Gly
1               5                   10

<210> SEQ ID NO 5
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 5

Phe Val Asp Thr Thr Ser Xaa Xaa Xaa Glu Ser Pro Cys Gly
1               5                   10

<210> SEQ ID NO 6
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: (4-CF3)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 6

Phe Val Asp Thr Thr Ser Xaa Xaa Xaa Glu Ser Pro Cys Gly
```

<210> SEQ ID NO 7
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 7

Phe Val Asp Thr Thr Ser Xaa Xaa Xaa Lys Ser Pro Cys Gly
1               5                   10

<210> SEQ ID NO 8
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 8

Phe Val Ser Thr Thr Xaa Xaa Xaa Xaa Asp Ser Pro Cys Gly
1               5                   10

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES

```
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 9

Phe Val Ser Thr Thr Ser Xaa Xaa Xaa Asp Arg Pro Cys Gly
1               5                   10

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 10

Phe Val Asp Thr Thr Xaa Xaa Xaa Xaa Glu Ser Pro Cys Gly
1               5                   10

<210> SEQ ID NO 11
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (4-CF3)F
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (4-CF3)F
<220> FEATURE:
<221> NAME/KEY: MOD_RES
<222> LOCATION: (9)..(9)
```

```
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 11

Phe Val Ser Thr Thr Xaa Xaa Xaa Xaa Glu Arg Pro Cys Gly
1               5                   10

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 12

Phe Val Ser Thr Thr Ser Xaa Xaa Xaa Glu Ser Pro Cys Gly
1               5                   10

<210> SEQ ID NO 13
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 13

Phe Val Ser Thr Thr Xaa Xaa Xaa Xaa Glu Ser Pro Cys Gly
1               5                   10

<210> SEQ ID NO 14
```

```
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (3,4-diCl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 14

Phe Val Ser Thr Thr Xaa Xaa Xaa Xaa Asp Arg Pro Cys Gly
1               5                   10

<210> SEQ ID NO 15
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (3-F)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 15

Phe Val Ser Thr Thr Xaa Xaa Xaa Xaa Asp Arg Pro Cys Gly
1               5                   10

<210> SEQ ID NO 16
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (7)..(7)
<223> OTHER INFORMATION: (N-Me)F
<220> FEATURE:
<221> NAME/KEY: MOD_RES
<222> LOC

Phe Val Asn Thr Thr Ala Xaa Xaa Xaa Gln Ala Pro Cys Gly
1               5                   10

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 19

Phe Val Pro Thr Thr Xaa Xaa Xaa Xaa Asp Arg Pro Cys Gly
1               5                   10

<210> SEQ ID NO 20
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 20

Phe Val Ser Thr Thr Xaa Xaa Xaa Xaa Pro Ser Pro Cys Gly
1               5                   10

<210> SEQ ID NO 21
<211> LENGTH: 14
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 21

Phe Val Pro Thr Thr Ala Xaa Xaa Xaa Glu Ala Pro Cys Gly
1               5                   10

<210> SEQ ID NO 22
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 22

Phe Val Ala Thr Thr Phe Xaa Xaa Xaa Lys Ala Pro Cys Gly
1               5                   10

<210> SEQ ID NO 23
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
```

```
<223> OTHER INFORMATION: /note="See specification as filed for detailed
      description of substitutions and preferred embodiments"

<400> SEQUENCE: 23

Phe Val Asn Thr Thr Phe Xaa Xaa Xaa Lys Ala Pro Cys Gly
1               5                   10

<210> SEQ ID NO 24
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 24

Phe Val Ser Thr Thr Phe Xaa Xaa Xaa Glu Ala Pro Cys Gly
1               5                   10

<210> SEQ ID NO 25
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 25

Phe Val Ser Thr Thr Xaa Xaa Xaa Xaa Glu Ser Pro Cys Gly
1               5                   10

<210> SEQ ID NO 26
<211> LENGTH: 14
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (3,4-diCl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 26

Phe Val Asp Thr Thr Xaa Xaa Xaa Xaa Glu Ser Pro Cys Gly
1               5                   10

<210> SEQ ID NO 27
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 27

Phe Glu Asn Thr Thr Phe Xaa Xaa Xaa Ala Ser Pro Cys Gly
1               5                   10

<210> SEQ ID NO 28
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (4-Cl)F
<220> FEATURE:
```

```
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 28

Phe Val Pro Thr Thr Phe Xaa Xaa Xaa Pro Ala Pro Cys
1               5                   10

<210> SEQ ID NO 29
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (4-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 29

Phe Val Pro Thr Thr Phe Xaa Xaa Xaa Asp Ala Pro Cys
1               5                   10

<210> SEQ ID NO 30
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Hse
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (4-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 30

Phe Val Xaa Thr Thr Phe Xaa Xaa Xaa Asp Ala Pro Cys
1               5                   10
```

```
<210> SEQ ID NO 31
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 31

Phe Val Ser Thr Thr Xaa Xaa Xaa Xaa Asp Arg Pro Cys
1               5                   10

<210> SEQ ID NO 32
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (4-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 32

Phe Val Ala Thr Thr Phe Xaa Xaa Xaa Asn Ala Pro Cys
1               5                   10

<210> SEQ ID NO 33
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
```

```
<220> FEATURE:
<221> NAME/KEY: MOD_RES
<222> LOCATION: (8)..(8)
<223> OTHER INFORMATION: (4-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 33

Phe Val Pro Thr Thr Val Xaa Xaa Xaa Glu Ala Pro Cys
1               5                   10

<210> SEQ ID NO 34
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: MOD_RES
<222> LOCATION: (10)..(10)
<223> OTHER INFORMATION: (N-Me)E
<220> FEATURE:
<221> NAME/KEY: source
<223> OTHER INFORMATION: /note="See specification as filed for detailed
      description of substitutions and preferred embodiments"

<400> SEQUENCE: 34

Phe Val Asn Thr Thr Phe Xaa Xaa Xaa Xaa Ala Pro Cys
1               5                   10

<210> SEQ ID NO 35
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"
```

-continued

```
<400> SEQUENCE: 35

Phe Val Pro Thr Thr Phe Xaa Xaa Xaa Glu Ala Pro Cys
1               5                   10

<210> SEQ ID NO 36
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 36

Phe Val Pro Thr Thr Xaa Xaa Xaa Xaa Glu Ala Pro Cys
1               5                   10

<210> SEQ ID NO 37
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 37

Phe Val Pro Thr Thr Xaa Xaa Xaa Xaa Ala Ala Pro Cys
1               5                   10

<210> SEQ ID NO 38
<211> LENGTH: 15
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Bip
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 38

Phe Val Pro Thr Thr Xaa Xaa Xaa Xaa Glu Ala Pro Cys Gly Lys
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
```

```
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 39

Phe Val Ser Thr Thr Ser Xaa Xaa Xaa Asp Arg Pro Cys Gly Lys
1               5                   10                  15

<210> SEQ ID NO 40
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
```

```
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 40

Phe Val Ser Thr Thr Ser Xaa Xaa Xaa Asp Arg Pro Cys Gly
1               5                   10

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
```

-continued

```
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
```

```
<223> OTHER INFORMATION: /note="See specification as filed for detailed
      description of substitutions and preferred embodiments"

<400> SEQUENCE: 41

Phe Val Ser Thr Thr Ser Xaa Xaa Xaa Asp Arg Pro Cys Gly Lys
1               5                   10                  15

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
```

```
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 42

Phe Val Ser Thr Thr Ser Xaa Xaa Xaa Asp Arg Pro Cys Gly Lys
1               5                   10                  15

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
```

```
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 43

Phe Val Ser Thr Thr Ser Xaa Xaa Xaa Asp Arg Pro Cys Gly Lys
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
```

```
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: MOD_RES
<222> LOCATION: (13)..(13)
<223> OTHER INFORMATION: D-Cys
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 44

Phe Val Ser Thr Thr Ser Xaa Xaa Xaa Asp Arg Pro Xaa Gly Lys
1               5                   10                  15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
```

```
<221> NAME/KEY: source
<223> OTHER INFORMATION: /note="See specification as filed for detailed
      description of substitutions and preferred embodiments"

<400> SEQUENCE: 45

Phe Val Ser Thr Thr Ser Xaa Xaa Xaa Asp Arg Pro Cys Gly Lys
1               5                   10                  15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
```

```
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 46

Phe Val Ser Thr Thr Ser Xaa Xaa Xaa Asp Arg Pro Cys Gly Lys
1               5                   10                  15

<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: MOD_RES
```

```
<222> LOCATION: (13)..(13)
<223> OTHER INFORMATION: D-Cys
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 47

Phe Val Ser Thr Thr Ser Xaa Xaa Xaa Asp Arg Pro Xaa Gly Lys
1               5                   10                  15

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
```

```
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 48

Phe Val Ser Thr Thr Ser Xaa Xaa Xaa Asp Arg Pro Cys Gly Lys
1               5                   10                  15

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
```

```
                D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 49

Phe Val Ser Thr Thr Ser Xaa Xaa Xaa Asp Arg Pro Cys Gly Lys
1               5                  10                  15

<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
```

```
            "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
            or "D-Tyr" or "(4-CF3)Phe" or "D-(4-CF3)Phe" or "Ala"
            or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
            D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
            (3,4-diCl)Phe, D-(3,4-diCl)Phe, (3-F)Phe, D-(3-F)Phe, (4-Cl)Phe,
            or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
            D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
            or "D-Glu" or "Lys" or "D-Lys" or "Gln" or "D-Gln" or
            "Pro" or "D-Pro" or "Ala" or "D-Ala" or "(N-Me)Glu"
            or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
            or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
            'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
            have no preference with respect to those in the annotations
            for variant positions"
<220> FEATURE:
<221> NAME/KEY: source
<223> OTHER INFORMATION: /note="See specification as filed for detailed
            description of substitutions and preferred embodiments"

<400> SEQUENCE: 50

Phe Val Ser Thr Thr Ser Xaa Xaa Xaa Asp Arg Pro Cys Gly Lys
1               5                   10                  15
```

```
<210> SEQ ID NO 51
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: SITE
<222> LOCATION: (1)..(13)
<223> OTHER INFORMATION: /note="Variant residues given in the sequence
      have no preference with respect to those in the annotations
``` for variant positions"
<220> FEATURE:
<221> NAME/KEY: source
<223> OTHER INFORMATION: /note="See specification as filed for detailed
      description of substitutions and preferred embodiments"

<400> SEQUENCE: 51

Phe Val Ser Thr Thr Ser Xaa Xaa Xaa Asp Arg Pro Cys
1               5                   10

<210> SEQ ID NO 52
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)

```
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: SITE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 52

Phe Val Ser Thr Thr Ser Xaa Xaa Xaa Asp Arg Pro Cys Gly
1               5                   10

<210> SEQ ID NO 53
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
```

"Pro" or "D-Pro" or "Ala" or "D-Ala" or "(N-Me)Glu"
or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
have no preference with respect to those in the annotations
for variant positions"
<220> FEATURE:
<221> NAME/KEY: source
<223> OTHER INFORMATION: /note="See specification as filed for detailed
description of substitutions and preferred embodiments"

<400> SEQUENCE: 53

Phe Val Ser Thr Thr Ser Xaa Xaa Xaa Asp Arg Pro Cys Gly Lys
1               5                   10                  15

<210> SEQ ID NO 54
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: VARIANT
<222> LOCATION: (1)..(1)
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
or "D-Asn" or "Pro" or "D-Pro" or "Ala" or
"D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"

or "D-Tyr" or "(4-CF3)Phe" or "D-(4-CF3)Phe" or "Ala"
or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
(3,4-diCl)Phe, D-(3,4-diCl)Phe, (3-F)Phe, D-(3-F)Phe, (4-Cl)Phe,
or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
or "D-Glu" or "Lys" or "D-Lys" or "Gln" or "D-Gln" or
"Pro" or "D-Pro" or "Ala" or "D-Ala" or "(N-Me)Glu"
or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
have no preference with respect to those in the annotations
for variant positions"
<220> FEATURE:
<221> NAME/KEY: source
<223> OTHER INFORMATION: /note="See specification as filed for detailed
description of substitutions and preferred embodiments"

<400> SEQUENCE: 54

Phe Val Ser Thr Thr Ser Xaa Xaa Xaa Asp Arg Pro Cys Gly Lys
1               5                   10                  15

<210> SEQ ID NO 55
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: VARIANT
<222> LOCATION: (1)..(1)

```
<223> OTHER INFORMATION: /replace="D-Phe"
<220> FEATURE:
<221> NAME/KEY: VARIANT
<222> LOCATION: (2)..(2)
<223> OTHER INFORMATION: /replace="D-Val" or "Glu" or "D-Glu"
<220> FEATURE:
<221> NAME/KEY: VARIANT
<222> LOCATION: (3)..(3)
<223> OTHER INFORMATION: /replace="D-Ser" or "Asp" or "D-Asp" or "Asn"
      or "D-Asn" or "Pro" or "D-Pro" or "Ala" or
      "D-Ala" or "Hse" or "D-Hse"
<220> FEATURE:
<221> NAME/KEY: VARIANT
<222> LOCATION: (4)..(4)
<223> OTHER INFORMATION: /replace="D-Thr" or "Ser" or "D-Ser"
<220> FEATURE:
<221> NAME/KEY: VARIANT
<222> LOCATION: (5)..(5)
<223> OTHER INFORMATION: /replace="D-Thr"
<220> FEATURE:
<221> NAME/KEY: VARIANT
<222> LOCATION: (6)..(6)
<223> OTHER INFORMATION: /replace="Bip" or "D-Bip" or "D-Ser" or "Tyr"
      or "D-Tyr" or "(4-CF3)Phe" or "D-(4-CF3)Phe" or "Ala"
      or "D-Ala" or "Phe" or "D-Phe" or "Val" or "D-Val"
<220> FEATURE:
<221> NAME/KEY: MOD_RES
<222> LOCATION: (7)..(7)
<223> OTHER INFORMATION: (N-Me)Ala, D-(N-Me)Ala, (N-Me)Phe, or
      D-(N-Me)Phe
<220> FEATURE:
<221> NAME/KEY: MOD_RES
<222> LOCATION: (8)..(8)
<223> OTHER INFORMATION: Bip, D-Bip, (4-CF3)Phe, D-(4-CF3)Phe,
      (3,4-diCl)Phe, D-(3,4-diCl)Phe, (3-F)Phe, D-(3-F)Phe, (4-Cl)Phe,
      or D-(4-Cl)Phe
<220> FEATURE:
<221> NAME/KEY: MOD_RES
<222> LOCATION: (9)..(9)
<223> OTHER INFORMATION: (N-Me)Ala, D-(N-Me)Ala, (N-Me)Glu, or
      D-(N-Me)Glu
<220> FEATURE:
<221> NAME/KEY: VARIANT
<222> LOCATION: (10)..(10)
<223> OTHER INFORMATION: /replace="D-Asp" or "Asn" or "D-Asn" or "Glu"
      or "D-Glu" or "Lys" or "D-Lys" or "Gln" or "D-Gln" or
      "Pro" or "D-Pro" or "Ala" or "D-Ala" or "(N-Me)Glu"
      or "D-(N-Me)Glu"
<220> FEATURE:
<221> NAME/KEY: VARIANT
<222> LOCATION: (11)..(11)
<223> OTHER INFORMATION: /replace="D-Arg" or "Ser" or "D-Ser" or "His"
      or "D-His" or "Ala" or "D-Ala"
<220> FEATURE:
<221> NAME/KEY: VARIANT
<222> LOCATION: (12)..(12)
<223> OTHER INFORMATION: /replace="D-Pro"
<220> FEATURE:
<221> NAME/KEY: VARIANT
<222> LOCATION: (13)..(13)
<223> OTHER INFORMATION: /replace="D-Cys"
<220> FEATURE:
<221> NAME/KEY: VARIANT
<222> LOCATION: (14)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" " or "D-Lys"
<220> FEATURE:
<221> NAME/KEY: SITE
<222> LOCATION: (14)..(15)
<223> OTHER INFORMATION: /note="This region must embody either 'Gly',
      'Gly-Lys', 'Gly-D-Lys', or be absent in its entirety"
<220> FEATURE:
<221> NAME/KEY: SITE
<222> LOCATION: (1)..(15)
<223> OTHER INFORMATION: /note="Variant residues given in the sequence
      have no preference with respect to those in the annotations
```

```
      for variant positions"
<220> FEATURE:
<221> NAME/KEY: source
<223> OTHER INFORMATION: /note="See specification as filed for detailed
      description of substitutions and preferred embodiments"

<400> SEQUENCE: 55

Phe Val Ser Thr Thr Ser Xaa Xaa Xaa Asp Arg Pro Cys Gly Lys
1               5                   10                  15

<210> SEQ ID NO 56
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)E
<220> FEATURE:
<221> NAME/KEY: source
<223> OTHER INFORMATION: /note="See specification as filed for detailed
      description of substitutions and preferred embodiments"

<400> SEQUENCE: 56

Phe Val Asp Thr Thr Ser Xaa Xaa Xaa Asn Ser Pro Cys Gly
1               5                   10

<210> SEQ ID NO 57
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: D(tBu)
<220> FEATURE:
<221> NAME/KEY: MOD_RES
<222> LOCATION: (4)..(4)
<223> OTHER INFORMATION: T(tBu)
<220> FEATURE:
<221> NAME/KEY: MOD_RES
<222> LOCATION: (5)..(5)
<223> OTHER INFORMATION: T(tBu)
<220> FEATURE:
<221> NAME/KEY: MOD_RES
<222> LOCATION: (6)..(6)
<223> OTHER INFORMATION: S(tBu)
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)E(tBu)
```

```
<220> FEATURE:
<221> NAME/KEY: MOD_RES
<222> LOCATION: (11)..(11)
<223> OTHER INFORMATION: S(tBu)
<220> FEATURE:
<221> NAME/KEY: MOD_RES
<222> LOCATION: (13)..(13)
<223> OTHER INFORMATION: C(Trt)- NHresin
<220> FEATURE:
<221> NAME/KEY: source
<223> OTHER INFORMATION: /note="See specification as filed for detailed
      description of substitutions and preferred embodiments"

<400> SEQUENCE: 57

Phe Val Xaa Xaa Xaa Xaa Xaa Xaa Xaa Asn Xaa Pro Xaa Gly
1               5                   10

<210> SEQ ID NO 58
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: D(tBu)
<220> FEATURE:
<221> NAME/KEY: MOD_RES
<222> LOCATION: (4)..(4)
<223> OTHER INFORMATION: T(tBu)
<220> FEATURE:
<221> NAME/KEY: MOD_RES
<222> LOCATION: (5)..(5)
<223> OTHER INFORMATION: T(tBu)
<220> FEATURE:
<221> NAME/KEY: MOD_RES
<222> LOCATION: (6)..(6)
<223> OTHER INFORMATION: S(tBu)
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)E(tBu)
<220> FEATURE:
<221> NAME/KEY: MOD_RES
<222> LOCATION: (11)..(11)
<223> OTHER INFORMATION: S(tBu)
<220> FEATURE:
<221> NAME/KEY: MOD_RES
<222> LOCATION: (13)..(13)
<223> OTHER INFORMATION: C(Trt) resin
<220> FEATURE:
<221> NAME/KEY: source
<223> OTHER INFORMATION: /note="See specification as filed for detailed
      description of substitutions and preferred embodiments"

<400> SEQUENCE: 58

Phe Val Xaa Xaa Xaa Xaa Xaa Xaa Xaa Asn Xaa Pro Xaa Gly
1               5                   10

<210> SEQ ID NO 59
<211> LENGTH: 14
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)F
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)E
<220> FEATURE:
<221> NAME/KEY: source
<223> OTHER INFORMATION: /note="See specification as filed for detailed
      description of substitutions and preferred embodiments"

<400> SEQUENCE: 59

Phe Val Asp Thr Thr Ser Xaa Xaa Xaa Asn Ser Pro Cys Gly
1               5                   10

<210> SEQ ID NO 60
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (p-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 60

Phe Val Pro Thr Thr Phe Xaa Xaa Xaa Pro Ala Pro Cys
1               5                   10

<210> SEQ ID NO 61
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: T(tBu)
<220> FEATURE:
<221> NAME/KEY: MOD_RES
<222> LOCATION: (5)..(5)
<223> OTHER INFORMATION: T(tBu)
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
```

```
<222> LOCATION: (8)..(8)
<223> OTHER INFORMATION: (p-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: MOD_RES
<222> LOCATION: (13)..(13)
<223> OTHER INFORMATION: C-(Trt)NHresin
<220> FEATURE:
<221> NAME/KEY: source
<223> OTHER INFORMATION: /note="See specification as filed for detailed
      description of substitutions and preferred embodiments"

<400> SEQUENCE: 61

Phe Val Pro Xaa Xaa Phe Xaa Xaa Xaa Pro Ala Pro Xaa
1               5                   10

<210> SEQ ID NO 62
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: T(tBu)
<220> FEATURE:
<221> NAME/KEY: MOD_RES
<222> LOCATION: (5)..(5)
<223> OTHER INFORMATION: T(tBu)
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: (p-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: MOD_RES
<222> LOCATION: (13)..(13)
<223> OTHER INFORMATION: C-(Trt)NH-resin
<220> FEATURE:
<221> NAME/KEY: source
<223> OTHER INFORMATION: /note="See specification as filed for detailed
      description of substitutions and preferred embodiments"

<400> SEQUENCE: 62

Phe Val Pro Xaa Xaa Phe Xaa Xaa Xaa Pro Ala Pro Xaa
1               5                   10

<210> SEQ ID NO 63
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
```

```
<223> OTHER INFORMATION: (p-Cl)F
<220> FEATURE:
<221> NAME/KEY: MOD_RES
<222> LOCATION: (9)..(9)
<223> OTHER INFORMATION: (N-Me)A
<220> FEATURE:
<221> NAME/KEY: source
<223> OTHER INFORMATION: /note="See specification as filed for detailed
      description of substitutions and preferred embodiments"

<400> SEQUENCE: 63

Phe Val Pro Thr Thr Phe Xaa Xaa Xaa Pro Ala Pro Cys
1               5                   10

<210> SEQ ID NO 64
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: MOD_RES
<222> LOCATION: (10)..(10)
<223> OTHER INFORMATION: (N-Me)E
<220> FEATURE:
<221> NAME/KEY: source
<223> OTHER INFORMATION: /note="See specification as filed for detailed
      description of substitutions and preferred embodiments"

<400> SEQUENCE: 64

Phe Val Asn Thr Thr Phe Xaa Xaa Xaa Xaa Ala Pro Cys
1               5                   10

<210> SEQ ID NO 65
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: T(tBu)
<220> FEATURE:
<221> NAME/KEY: MOD_RES
<222> LOCATION: (5)..(5)
<223> OTHER INFORMATION: T(tBu)
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
```

```
<220> FEATURE:
<221> NAME/KEY: MOD_RES
<222> LOCATION: (10)..(10)
<223> OTHER INFORMATION: (N-Me)E(tBu)
<220> FEATURE:
<221> NAME/KEY: MOD_RES
<222> LOCATION: (13)..(13)
<223> OTHER INFORMATION: C(Trt)N(Et)resin
<220> FEATURE:
<221> NAME/KEY: source
<223> OTHER INFORMATION: /note="See specification as filed for detailed
      description of substitutions and preferred embodiments"

<400> SEQUENCE: 65

Phe Val Asn Xaa Xaa Phe Xaa Xaa Xaa Xaa Ala Pro Xaa
1               5                   10

<210> SEQ ID NO 66
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: T(tBu)
<220> FEATURE:
<221> NAME/KEY: MOD_RES
<222> LOCATION: (5)..(5)
<223> OTHER INFORMATION: T(tBu)
<220> FEATURE:
<221> NAME/KEY: MOD_RES
<222> LOCATION: (7)..(7)
<223> OTHER INFORMATION: (N-Me)A
<220> FEATURE:
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: MOD_RES
<222> LOCATION: (10)..(10)
<223> OTHER INFORMATION: (N-Me)E(tBu)
<220> FEATURE:
<221> NAME/KEY: MOD_RES
<222> LOCATION: (13)..(13)
<223> OTHER INFORMATION: C(Trt)N(Et)-resin
<220> FEATURE:
<221> NAME/KEY: source
<223> OTHER INFORMATION: /note="See specification as filed for detailed
      description of substitutions and preferred embodiments"

<400> SEQUENCE: 66

Phe Val Asn Xaa Xaa Phe Xaa Xaa Xaa Xaa Ala Pro Xaa
1               5                   10

<210> SEQ ID NO 67
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: (N-Me)A
<220> FEATURE:
```

```
<221> NAME/KEY: MOD_RES
<222> LOCATION: (8)..(8)
<223> OTHER INFORMATION: Bip
<220> FEATURE:
<221> NAME/KEY: MOD_RES
<222> LOCATION: (9)..(9)
<223> OTHER INFORMATION: (N-Me)A
<220> FEATURE:
<221> NAME/KEY: MOD_RES
<222> LOCATION: (10)..(10)
<223> OTHER INFORMATION: (N-Me)E
<220> FEATURE:
<221> NAME/KEY: source
<223> OTHER INFORMATION: /note="See specification as filed for detailed
      description of substitutions and preferred embodiments"

<400> SEQUENCE: 67

Phe Val Asn Thr Thr Phe Xaa Xaa Xaa Xaa Ala Pro Cys
1               5                   10
```